(12) United States Patent
Bowman et al.

(10) Patent No.: US 12,054,607 B2
(45) Date of Patent: Aug. 6, 2024

(54) TOUGH, HEALABLE COMPOSITES DISPLAYING STRESS RELAXATION AT THE RESIN-FILLER INTERFACE

(71) Applicant: THE REGENTS OF THE UNIVERSITY OF COLORADO, A BODY CORPORATE, Denver, CO (US)

(72) Inventors: Christopher N. Bowman, Boulder, CO (US); Nancy Sowan, Boulder, CO (US); Lewis M. Cox, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 936 days.

(21) Appl. No.: 16/982,393

(22) PCT Filed: Mar. 19, 2019

(86) PCT No.: PCT/US2019/023030
§ 371 (c)(1),
(2) Date: Sep. 18, 2020

(87) PCT Pub. No.: WO2019/183140
PCT Pub. Date: Sep. 26, 2019

(65) Prior Publication Data
US 2021/0002469 A1    Jan. 7, 2021

Related U.S. Application Data

(60) Provisional application No. 62/644,667, filed on Mar. 19, 2018.

(51) Int. Cl.
*C08L 33/14* (2006.01)
*A61K 6/887* (2020.01)
(Continued)

(52) U.S. Cl.
CPC .............. *C08L 33/14* (2013.01); *A61K 6/887* (2020.01); *C08G 75/02* (2013.01); *C08K 5/3445* (2013.01); *C08K 7/16* (2013.01); *B82Y 5/00* (2013.01)

(58) Field of Classification Search
None
See application file for complete search history.

(56) References Cited

U.S. PATENT DOCUMENTS

2008/0269460 A1 * 10/2008 Bowman .................. C08F 2/38
568/50
2011/0014096 A1    1/2011 Fukuoka et al.
(Continued)

FOREIGN PATENT DOCUMENTS

WO   WO-2015074080 A1 *  5/2015  ............. C08G 75/00
WO   WO-2015143258 A1 *  9/2015  ............ A61K 6/0017
WO   WO-2016130573 A2 *  8/2016  ............. A61K 38/08

OTHER PUBLICATIONS

"International Search Report and Written Opinion dated Jul. 1, 2019 for PCT International Application No. PCT/US2019/023030".
(Continued)

*Primary Examiner* — Nicole M. Buie-Hatcher
(74) *Attorney, Agent, or Firm* — Saul Ewing LLP; Kathryn Doyle; Domingos Silva

(57) ABSTRACT

The present invention relates in part to compositions displaying stress relaxation at the polymer-filler interface. The adaptive interface (AI) formed by coupling moieties capable of dynamic covalent chemistry (DCC) within the polymer-filler interface promotes stress relaxation and yields tough, and healable composites.

18 Claims, 21 Drawing Sheets

(51) Int. Cl.
  *B82Y 5/00* (2011.01)
  *C08G 75/02* (2016.01)
  *C08K 5/3445* (2006.01)
  *C08K 7/16* (2006.01)

(56) References Cited

U.S. PATENT DOCUMENTS

| | | | | |
|---|---|---|---|---|
| 2013/0277890 A1* | 10/2013 | Bowman | ............... | A61L 27/50 525/445 |
| 2015/0031782 A1* | 1/2015 | Bowman | ............ | C08F 222/102 522/182 |
| 2015/0250687 A1* | 9/2015 | Bowman | ............ | C08G 18/3876 522/63 |
| 2017/0007505 A1* | 1/2017 | Moszner | ............... | C07D 251/34 |

OTHER PUBLICATIONS

Anbarasan, et al., "Effect of Multiwall Carbon Nanotube and Au Nanoparticle on the Structure-Property Relationship of Poly(N-isopropyl) acrylamide)", J Appl Polym Sci, vol. 124, 2011, pp. 3996-4006.

Capaldi, et al., "Molecular Response of a Glassy Polymer to Active Deformation", 45, 2004, 1391-1399.

Chatani, et al., "The Power of Light in Polymer Science: Photochemical Processes to Manipulate Polymer Formation, Structure, and Properties", Polym. Chem., 5(7), 2014.

Evans, et al., "Free-Radical Ring-Opening Polymerization of Cyclic Allylic Sulfides. 2. Effect of Substituents on Seven-and Eight-Membered Ring Low Shrink Monomers", Macromolecules, 33(18), 2000, 6722-6731.

Gonalves, et al., "BisGMA/TEGDMA Ratio and Filler Content Effects on Shrinkage Stress", Dent. Mater., 27(6), 2011, 520-526.

Guild, et al., "Particle Cavitation in Rubber Toughened Epoxies: The Role of Particle Size", J. Mater. Sci., 45(14), 2010, 3882-3894.

Hsieh, et al., "The Mechanisms and Mechanics of the Toughening of Epoxy Polymers Modi Fi Ed with Silica Nanoparticles", Polymer (Guildf), 51(26), 2010, 6284-6294.

Hsieh, et al., "The Toughness of Epoxy Polymers and Fibre Composites Modified with Rubber Microparticles and Silica Nanoparticles", J. Mater. Sci., 45(5), 2010, 1193-1210.

Huang, et al., "The Toughness of Epoxy Polymers Containing Microvoids 1330 Polymer", vol. 33, No. 6 (Toughness of Epoxy Polymers: Y. Huang and A. J. Kinloch. Technology 1991, No. Aug. 1991-1993), 1992.

Kinloch, et al., "The Toughening of Cyanate-Ester Polymers. Part I Physical Modification Using Particles, Fibres and Woven-Mats", J. Mater. Sci., 37(3), 2002, 433-460.

Kloxin, et al., "Stress Relaxation via Addition-Fragmentation Chain Transfer in a Thiol-Ene Photopolymerization", Macromolecules, 42(7), 2009, 2551-2556.

Maria, et al., "Stress relaxation behavior of organically modified montmorillonite filled natural rubbert/nitrile rubber nanocomposites", Applied Clay Science, vol. 87, Jan. 1, 2014, pp. 120-128.

Michler, et al., "The Physics and Micro-Mechanics of Nano-Voids and Nano-Particles in Polymer Combinations", Polym. (United Kingdom), 54(13), 2013, 3131-3144.

Odell, et al., "Flow-Induced Scission of Isolated Macromolecules", J. Chem. Phys., 88(6), 1988, 4022-4028.

Ou, et al., "A New Conception on the Toughness of Nylon 6/silica Nanocomposite Prepared via in Situ Polymerization", vol. 36, 1998.

Queiroz, et al., "Evaluation of Linear Polymerization Shrinkage , Flexural Strength and Modulus of Elasticity of Dental Composites", 13, 2010, 51-55.

Ritchie, R. O., "The Conflicts between Strength and Toughness", Nat. Mater., 10(11), 2011, 817-822.

Schneider, et al., "Shrinkage Stresses Generated during Resin-Composite Applications", Journal of Dental Biomechanics, vol. 2010, Art. ID 131630, 2010.

Shah, et al., "Role of Filler and Functional Group Conversion in the Evolution of Properties in Polymeric Dental Restoratives", Dent. Mater., 30(5), May 2014, 586-593.

Song, et al., "Reduced Shrinkage Stress via Photo-Initiated copper(I)-Catalyzed Cycloaddition Polymerizations of Azide-Alkyne Resins", Dental Materials. Elsevier Inc., 32(11), Nov. 2016, 1332-1342.

Tsai, et al., "Investigating Mechanical Behaviors of Silica Nanoparticle Reinforced Composites", J. Compos. Mater., 44(4), 2010, 505-524.

Young, et al., "The Deformation of Hybrid-Particulate Composites", J. Mater. Sci., 21(2), 1986, 380-388.

Zhang, et al., "Fracture Behaviours of in Situ Silica Nanoparticle-Filled Epoxy at Different Temperatures.", Polymer (Guildf)., 49(17), 2008, 3816-3825.

Hopkinson , et al., "An overview of N-heterocyclic carbenes", Nature, vol. 510, Jun. 16, 2014, 485-496.

* cited by examiner 25 wt% Control SNP (PI)

25 wt% AFT SNP (AI)

TOUGH, HEALABLE COMPOSITES DISPLAYING STRESS RELAXATION AT THE RESIN-FILLER INTERFACE

CROSS-REFERENCE TO RELATED APPLICATIONS

The present application is a 35 U.S.C. § 371 national stage application from, and claims priority to, International Application No. PCT/US2019/023030, which claims priority under 35 U.S.C. § 119(e) to U.S. Provisional Application No. 62/644,667, filed Mar. 19, 2018, all of which are hereby incorporated by reference herein in their entireties.

STATEMENT REGARDING FEDERALLY SPONSORED RESEARCH OR DEVELOPMENT

This invention was made with government support under grant number DE023777 awarded by the National Institutes of Health, and grant number DMR1310528 awarded by the National Science Foundation. The government has certain rights in the invention.

BACKGROUND OF THE INVENTION

For decades, nanoparticles have been introduced as fillers into polymerizable resins to form composites with desired physical and mechanical properties. Clay reinforced resins emerged in the early 1900's, but interest within the scientific community surged in 1993 when Toyota researchers reported incredible increases in yield and tensile strengths exhibited by nylon 6 when combined with montmorillonite. Since that time, enormous effort has been invested into enhancing the performance of polymer-nanoparticle composites. Because of the enormous surface area they occupied, particle-polymer interfaces play significant role in numerous physical and chemical phenomena responsible for achieving desired properties for various applications.

However, it is also known that the nanoparticles, with their significantly higher modulus and generally lower thermal expansion, act as stress concentrators, and this behavior leads to particle-matrix (polymer) debonding and void formation, all of which significantly influences the failure of composite materials. Generally, the mechanical properties of particulate-filled polymer nanocomposites are affected by particle size, particle content, and particle-matrix interfacial adhesion, which is the most important factor for effective stress transfer between the particles and the matrix. Since the adhesive strength at the filler interface determines the stress transfer between the components, several techniques have been developed to improve the interactions between the fillers and the surrounding polymer, such as bonding the filler to the resin using self-assembled monolayers (SAMs) and surface modification of nanoparticles. However, these techniques improve the efficiency of stress transfer at the interface, but do not eliminate the issue of stress concentration or enable stress relaxation.

There remains a need in the art for developing novel composites that eliminate the issue of stress concentration and/or enable stress relaxation at the particle-polymer interface. Enabling stress reduction at the interface would dramatically impact the broad field of polymer composites. Numerous applications such as coatings, structural materials, dental materials, and others would benefit from enhanced mechanical performance associated with low polymerization stress, resistance to crack propagation and extremely high toughness that would result from a reduction in interfacial stress. The present invention meets this need.

BRIEF SUMMARY OF THE INVENTION

In one aspect, the invention provides a functionalized nanoparticle (NP). In another aspect, the invention provides a composition comprising a polymer and filler, wherein the filler comprises at least one nanoparticle of the invention functionalized with at least one chemical moiety capable of engaging in dynamic covalent chemistry (DCC) with the polymer at the polymer-filler interface. In yet another aspect, the invention provides a dental restorative material comprising at least one composition of the invention. In yet another aspect, the invention provides a method of forming a composition of the invention.

In certain embodiments, the filler comprises at least one selected from the group consisting of silica, carbon, metal oxide, clay, fiber, glass, ceramic, and polymeric filler.

In certain embodiments, the polymer further comprises at least one multifunctional monomer capable of engaging in DCC with at least one other monomer in the polymer to form a covalent adaptive network (CAN).

In certain embodiments, the DCC comprises at least one selected from the group consisting of reversible addition-fragmentation chain transfer (RAFT) mechanism, thiol-thioester exchange (TTE), Diels-Alder reaction, transesterification, transamination, and disulfide exchange.

In certain embodiments, the DCC at the polymer-filler interface is orthogonal to the DCC within the polymer.

In certain embodiments, the (NP) functionalized with a linker comprising at least one of the following groups: (a) at least one allylic terminal thiol (—SH) group; or (b) at least one multifunctional thioester of formula (I),

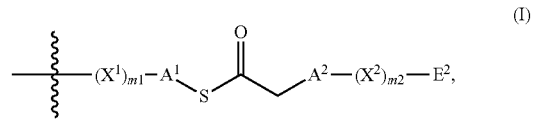

wherein in (I):
A$^1$ and A$^2$ are each independently selected from the group consisting of optionally substituted C$_1$-C$_{15}$ alkylene, optionally substituted C$_2$-C$_{15}$ alkenylene, optionally substituted C$_2$-C$_{15}$ alkynylene, optionally substituted C$_2$-C$_{15}$ heteroalkylene, optionally substituted C$_2$-C$_{15}$ heteroalkenylene and optionally substituted C$_2$-C$_{15}$ heteroalkynylene;
E$^2$ is selected from the group consisting of:

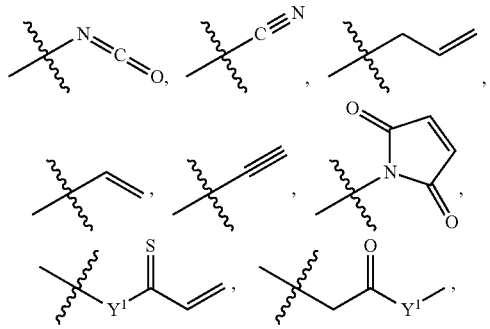

-continued

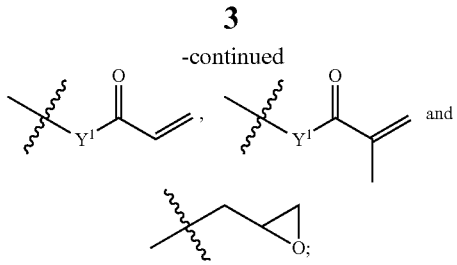

each instance of $Y^1$ is independently selected from the group consisting of O and $NR^1$; and each instance of $R^1$ being independently selected from the group consisting of H and $C_1$-$C_6$ alkyl;
m1 is 0 or 1;
m2 is 0 or 1;
$X^1$ is

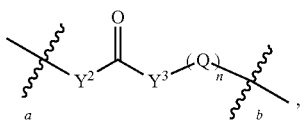

wherein:
bond a is to $A^1$,
Q is $CH_2$ or

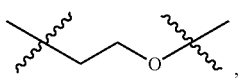

and
n is 0, 1, 2, 3, 4, 5 or 6;

$X^2$ is

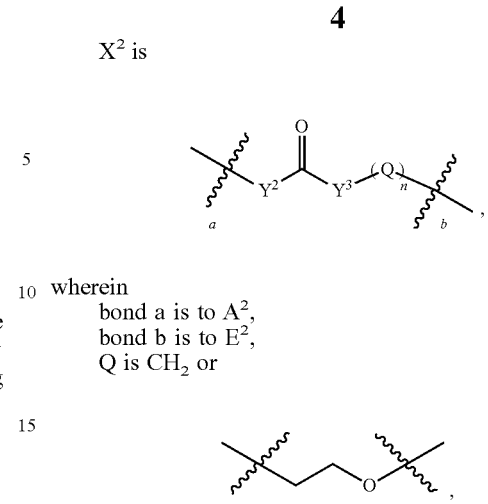

wherein
bond a is to $A^2$,
bond b is to $E^2$,
Q is $CH_2$ or and
n is 0, 1, 2, 3, 4, 5 or 6;
each instance of $Y^2$ and $Y^3$ is independently selected from the group consisting of $CR^1$, O and $NR^1$; and
each instance of $R^1$ is independently selected from the group consisting of H and $C_1$-$C_6$ alkyl.

In certain embodiments, the group (b) comprises a linker of formula (Ia):

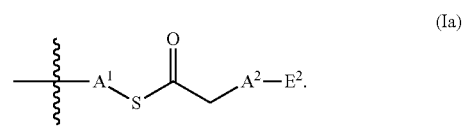

(Ia)

In certain embodiments, the group (b) comprises a linker selected from the group consisting of:

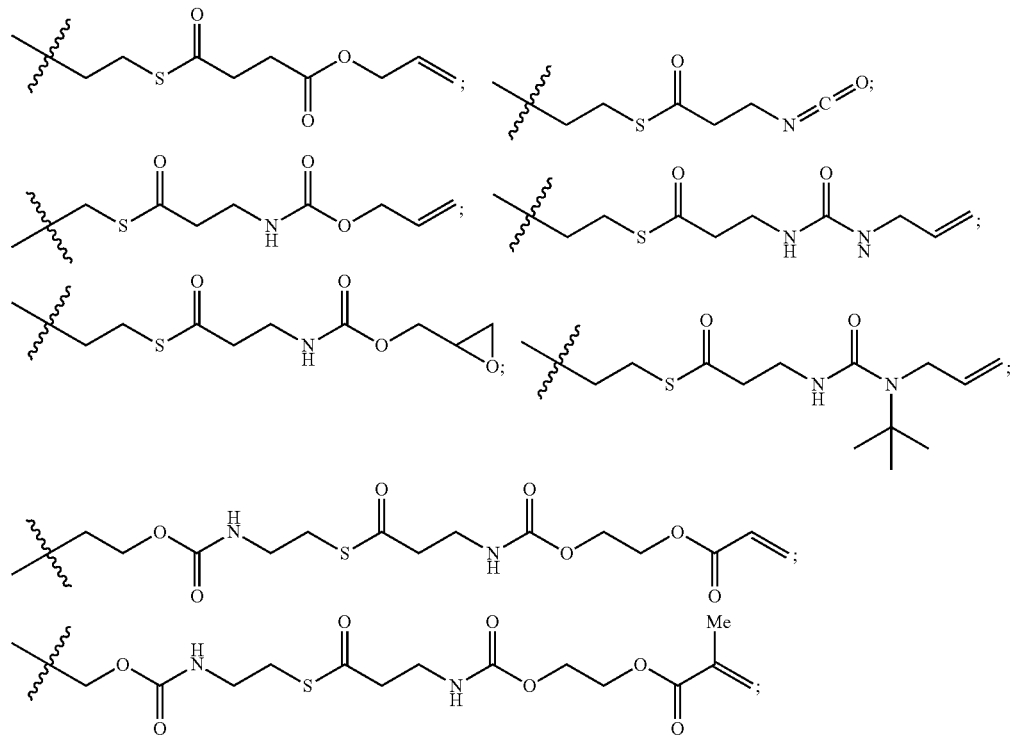

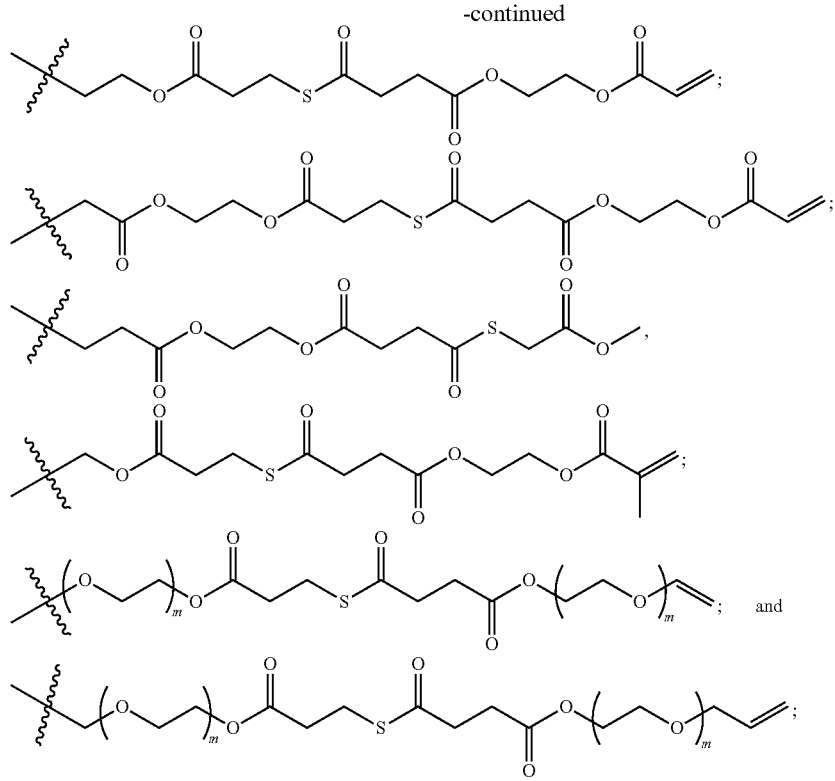

wherein each occurrence of m is independently selected from the group consisting of 0, 1, 2, 3, 4, 5, and 6.

In certain embodiments, the group (a) comprises —SCH$_2$C(=CH$_2$)CH$_2$SH.

In certain embodiments, the composition of the invention displaying stress relaxation at polymer-filler interface comprises a polymer and a filler comprising the at least one nanoparticle (NP) of the invention.

In certain embodiments, the linker is linked to the nanoparticle through a silane group.

In certain embodiments, the composition comprises at least one multifunctional thiol monomer.

In certain embodiments, wherein the at least one multifunctional thiol monomer is selected from the group consisting of

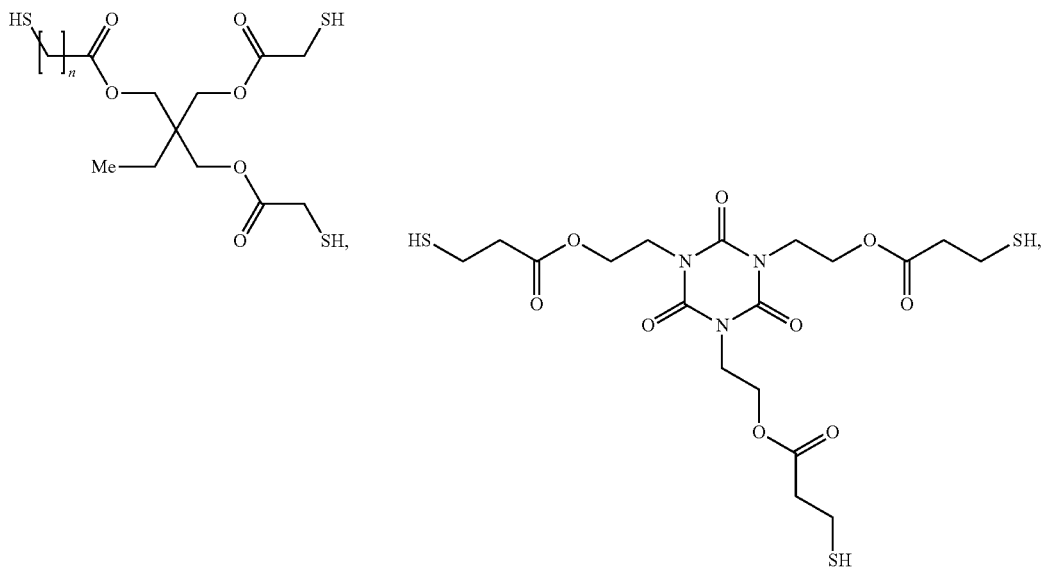

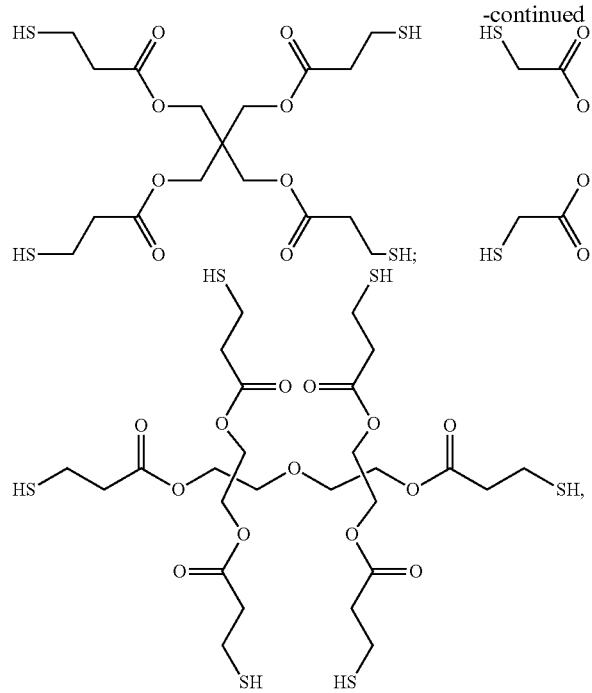
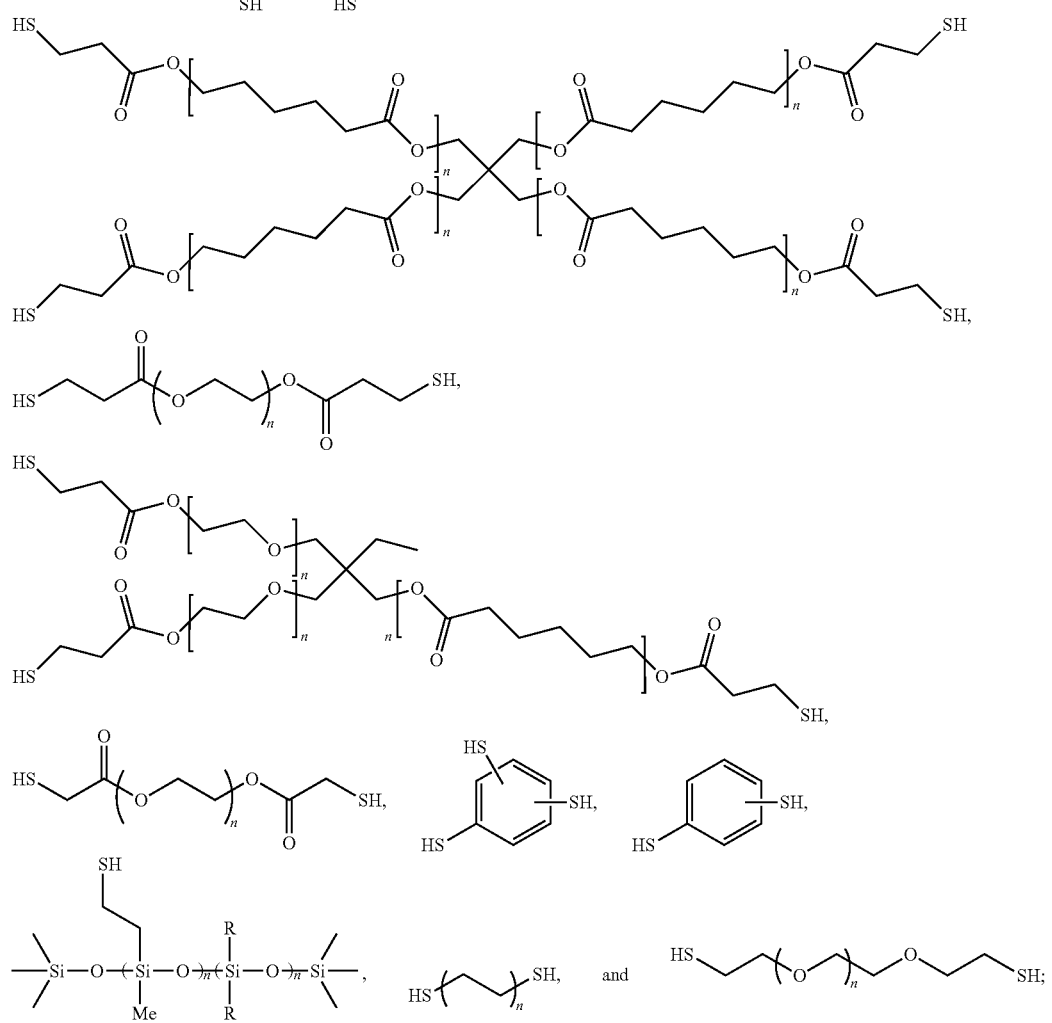

wherein each instance of n is independently an integer from 0 to 500.

In certain embodiments, the at least one multifunctional thiol monomer is selected from the group consisting of: pentaerythritol tetramercaptopropionate (PETMP), ethylene glycol bis(3-mercaptopropionate) (EGBMP); trimethylolpropane tris(3-mercaptopropionate)(TMPMP), 2,4,6-trioxo-1,3,5-triazina-triy (triethyl-tris (3-mercapto propionate); 1,2-ethanedithiol, 1,3-propanedithiol, 1,4-butanedithiol; 1,5-pentanedithiol; 1,6-hexanedithiol, 1,8-octanedithiol, 1,9-nonanedithiol, 1,11-undecanedithiol; 1,16-hexadecanedithiol, 2,5-dimercaptomethyl-1,4-dithiane, pentaerythritol tetramercaptoacetate; trimethylolpropane trimercaptoacetate; glycol dimercaptoacetate, 2,3-dimercapto-1-propanol; DL-dithiothreitol; 2-mercaptoethylsulfide, 2,3-(dimercaptoethylthio)-1-mercaptopropane, 1,2,3-trimercaptopropane, toluenedithiol; benzenedithiol, biphenyldithiol, benzenedimethanethiol; xylylenedithiol, 4,4'-dimercaptostilbene, glycol dimercaptopropionate, and any combinations thereof.

In certain embodiments, the polymer comprises a thiol-ene polymer.

In certain embodiments, the thiol-ene polymer comprises an ene monomer selected from a group consisting of ethylene glycoldi(meth)acrylate, ethoxylated bisphenol-A dimethacrylate (EBPADMA), tetraethyleneglycoldi(meth)acrylate (TEGDMA), poly(ethylene glycol) dimethacrylates, the condensation product of bisphenol A and glycidyl methacrylate, 2,2'-bis-[4-(3-methacryloxy-2-hydroxy propoxy)-phenyl]propane (BisGMA), hexanediol di(meth)acrylate, tripropylene glycol di(meth)acrylate, butanediol di(meth)acrylate, neopentyl glycol di(meth) acrylate, diethylene glycol di(meth)acrylate, triethylene glycol di(meth) acrylate, dipropylene glycol di(meth)acrylate, trimethylolpropane triacrylate (TMPTA), di(trimethylolpropane) tetraacrylate (DTPTA), divinyl sulfone (DVS), propargyl acrylate, 6-azidohexyl acrylate, [2-(acryloyloxy)ethyl]trimethylammonium chloride, acrylic acid, 2-(4-benzoyl-3-hydroxyphenoxy)ethyl acrylate, 3-sulfopropyl acrylate potassium salt, 2-hydroxyethyl acrylate and 2-(dimethylamino)ethyl acrylate. 1,1'-(Methylenedi-4,1-phenylene)bismaleimide, 1,4-di (maleimido)butane, N,N'-phenylenedimaleimide, N,N'-methylenebisacrylamide, and any combinations thereof.

In certain embodiments, the thiol-ene polymer comprises an ene monomer selected from a group consisting of triallyl-1,3,5-triazine-2,4,6-trione (TATATO), triethyleneglycol divinyl ether (TEGDVE), trimethylolpropane diallyl ether, dodecyl vinyl ether (DDVE), 1,6-heptadiyne, 1,7-octadiyne, bis-2,2-[4-(2-[norborn-2-ene-5-carboxylate]ethoxy) phenyl] propane (BPAEDN), 1,6-hexanediol di-(endo,exo-norborn-2-ene-5-carboxylate) (HDDN), trimethylolpropane tri-(norborn-2-ene-5-carboxylate) (TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), di(trimethylolpropane) tetra-(norborn-2-ene-5-carboxylate) (DTMPTN), and any combinations thereof.

In certain embodiments, the thiol-ene polymer further comprises 2-methylene-propane-1,3-di (thioethyl vinyl ether).

In certain embodiments, the linker comprise group (b) and the polymer comprises at least one free thiol from the at least one multifunctional thiol monomer.

In certain embodiments, the composition further comprises at least one polymerization initiator selected from the group consisting of a photoinitiator, a thermal initiator, and a redox initiator.

In certain embodiments, the at least one photoinitiator is activated upon exposure to light in at least one range selected from the group consisting of IR, visible, and UV.

In certain embodiments, the at least one photoinitiator is selected from the group consisting of: acetophenone, benzophenone, 2-phenylacetophenone, 2,2-dimethoxy-2-phenylacetophenone, Bis(2,4,6-trimethylbenzoyl)-phenylphosphineoxide, 2-Hydroxy-4'-(2-hydroxyethoxy)-2-methylpropiophenone, 2-methyl-(4-methylthienyl)-2-morpholinyl-1-propan-1-one, Diphenyl(2,4,6-trimethylbenzoyl)phosphine oxide, Ethyl (2,4,6-trimethylbenzoyl) phenyl phosphinate, lithium phenyl-2,4,6-trimethylbenzoylphosphinate.

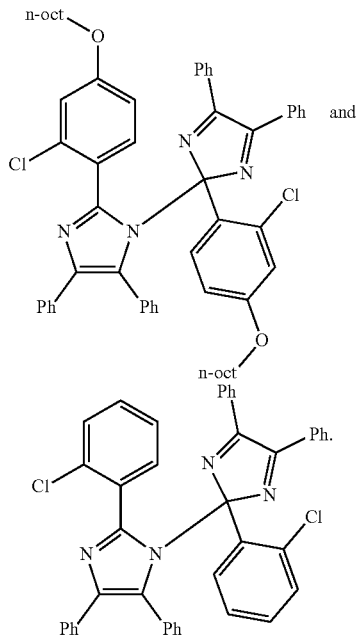

In certain embodiments, the at least one thermal initiator is reactive upon exposure to temperatures of about 30° C. to about 200° C.

In certain embodiments, the at least one thermal initiator is a compound selected from the group consisting of tert-Amyl peroxybenzoate, 4,4-Azobis(4-cyanovaleric acid), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis (tert-butylperoxy)-2,5-dimethylhexane, 2,5-Bis(tert-butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, cumene hydroperoxide, cyclohexanone peroxide, dicumyl peroxide, lauroyl peroxide, 2,4-pentanedione peroxide, peracetic acid, and potassium persulfate.

In certain embodiments, the at least one redox initiator is selected from the group consisting of: sodium iodide/hydrogen peroxide, potassium iodide/hydrogen peroxide, benzoyl peroxide/dimethyaniline, benzoyl peroxide/N,N-dimethyl p-toluidine, benzoyl peroxide/4-N,N-dimethylaminophenethyl alcohol, benzoyl peroxide/ethyl 4-dimethylamino benzoate, glucose oxidase/oxygen/iron(II) sulfate; and copper (II) sulfate/sodium ascorbate.

In certain embodiments, the composition further comprises a catalyst selected from the group consisting of a nucleophile and a base.

In certain embodiments, the nucleophile is selected from the group consisting of quinuclidine, 1,4-diazabicyclo[2.2.2]octane (DABCO), 4-Dimethylaminopyridine (DMAP), IMes, IPr, Ender's carbene, $PPh_3P(nBu)_3$, $P(tBu)_3$, $PCy_3$, and $PMe_3$.

In certain embodiments, the base is capable of deprotonating at least about 10% of the thiol groups in the composition.

In certain embodiments, the base is selected from the group consisting of an alkylthiolate salt, tetramethylguanidine (TMG), 1,8-Diazabicyclo[5,4,0]undec-7-ene (DBU), N,N-Diisopropylethylamine (DIPEA or Hunig's base), 4-tert-butyl pyridine, triethylamine (TEA), and N,N,N',N'',N''-pentamethyldiethylenetriamine (PMDETA).

In certain embodiments, the base is selected from the group consisting of a photo-activatable base and a thermal-activatable base.

In certain embodiments, the photo-activatable base is a compound selected from the group consisting of:

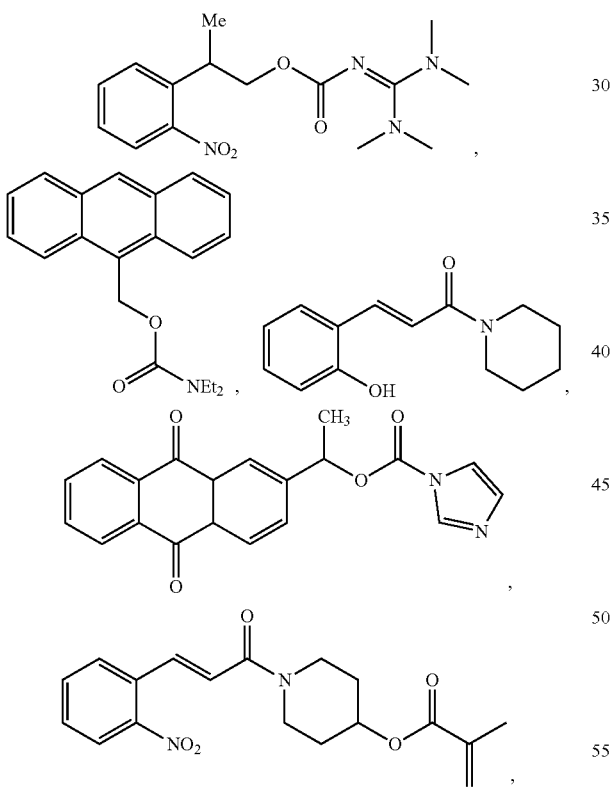

1,2-Diisopropyl-3-[Bis (dimethylamino) methylene]guanidium 2-(3-benzoylphenyl)propionate, 1,2-Dicyclohexyl-4,4,5,5-tetramethyl biguanidium n-butyltriphenylborate, and (Z)-{[Bis(dimethylamino) methylidene]amino}-N-cyclohexyl(cyclohexylamino)methaniminium tetrakis(3-fluorophenyl)borate.

In certain embodiments, the thermal-activatable base is selected from the group consisting of:

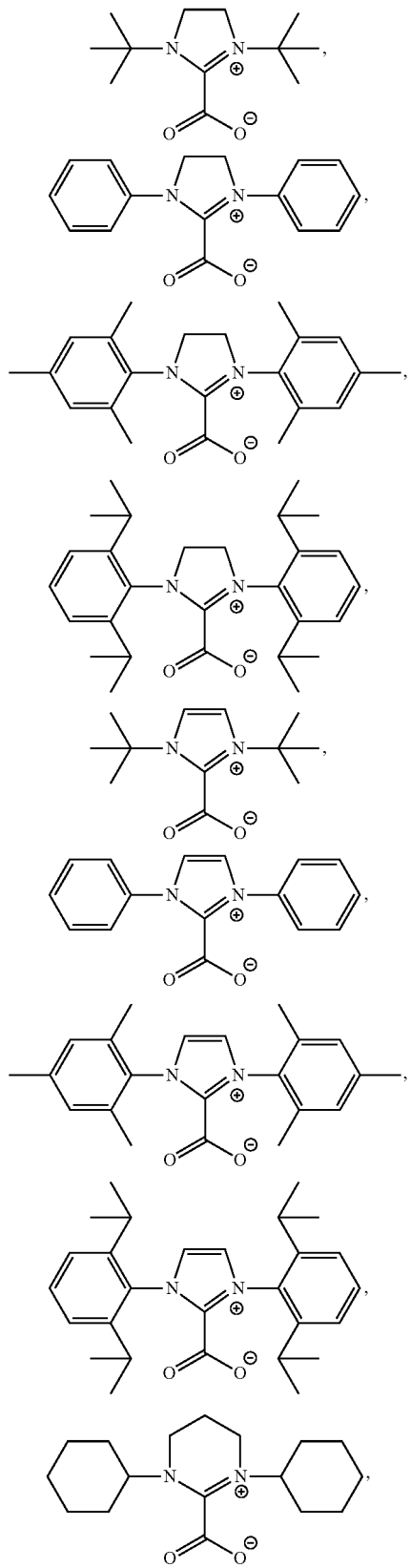

-continued

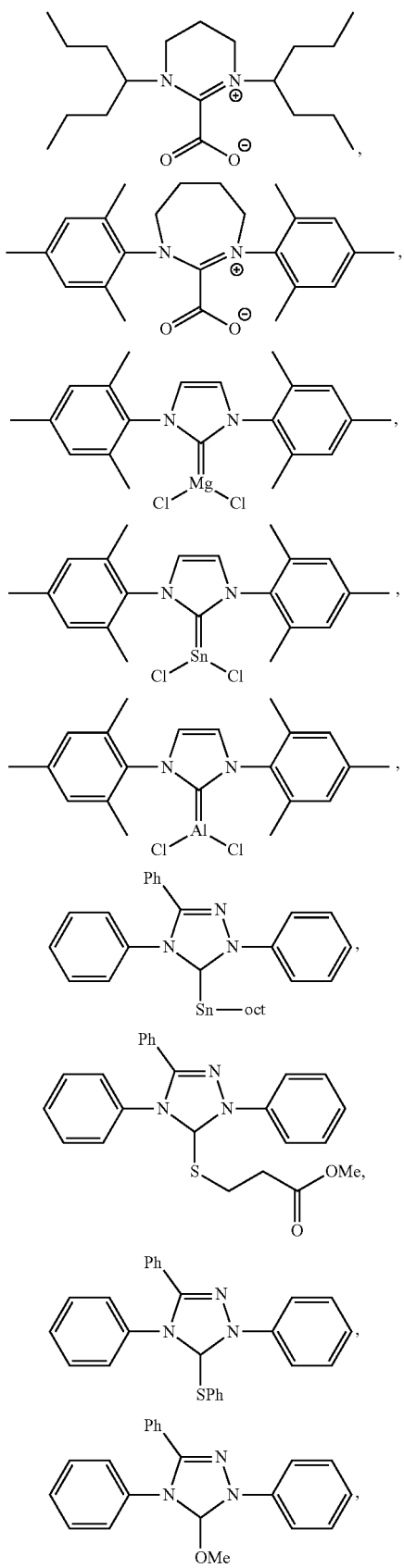

-continued

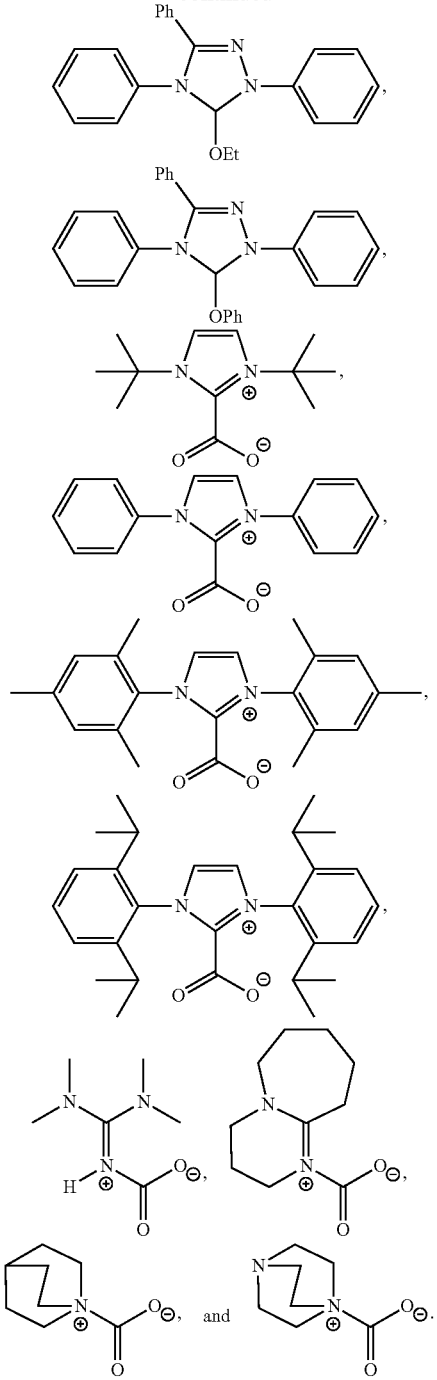

In certain embodiments, the composite comprises about 5% to about 50% of the at least one the NP by weight.

In certain embodiments, the fracture toughness of the composite increases with increasing weight fraction of the at least one NP.

In certain embodiments, the tensile strength of the composite increases with increasing weight fraction of the at least one NP.

In certain embodiments, the method of forming composition of the invention comprises combining the at least one nanoparticle (NP) of the invention with the at least one multifunctional thiol monomer of the invention, the at least one ene monomer of the invention and the at least one polymerization initiator to form an uncured polymer-filler composite. The method further comprises activating the at least one polymerization initiator, thus at least partially curing the polymer-filler composite.

In certain embodiments, the method further comprises postcuring the polymer-filler composite. In certain embodiments, the postcuring is performed at the temperature of about 50° C. to about 150° C. In certain embodiments, the postcuring lasts from about 2 hours to about 40 hours.

BRIEF DESCRIPTION OF THE FIGURES

For the purpose of illustrating the invention, depicted in the drawings are certain embodiments of the invention. However, the invention is not limited to the precise arrangements and instrumentalities of the embodiments depicted in the drawings.

DETAILED DESCRIPTION OF THE INVENTION

Figure 1:
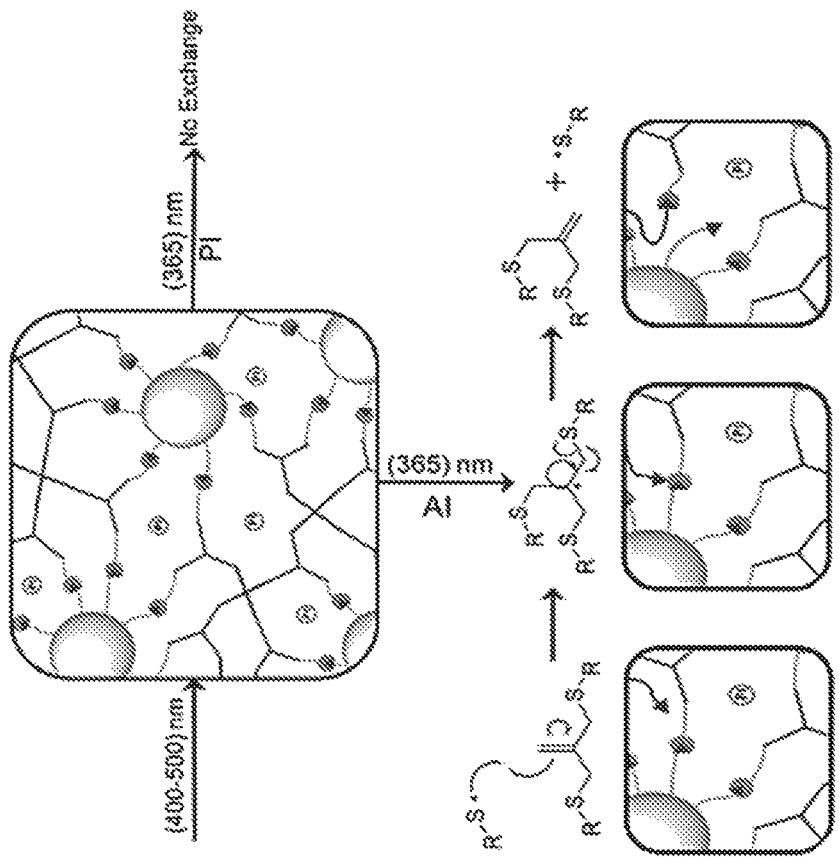
FIG. 1 shows monomers and fillers used in the formulation of the composites to examine the influence of dynamic bond exchange at the SNP-polymer interface. Resins were formulated such that there was a stoichiometric balance of PETMP and TATATO (1:1 SH:ene). By weight, 25% of the composite was comprised of SNPs, either AFT-functionalized to generate the AI or the corresponding negative control to generate the PI. Polymerization was initiated with 1 wt % of I819 (bis(2,4,6-trimethylbenzoyl)-phenylphosphineoxide) visible light photoinitiator, and 2 wt % of I651 (2,2-Dimethoxy-1,2-diphenylethan-1-one). Samples were photocured with 400-500 nm visible light at 50 mW/cm$^2$ for 20 min and then post-cured in an oven at 100° C. for 24 h.
Figure 1:
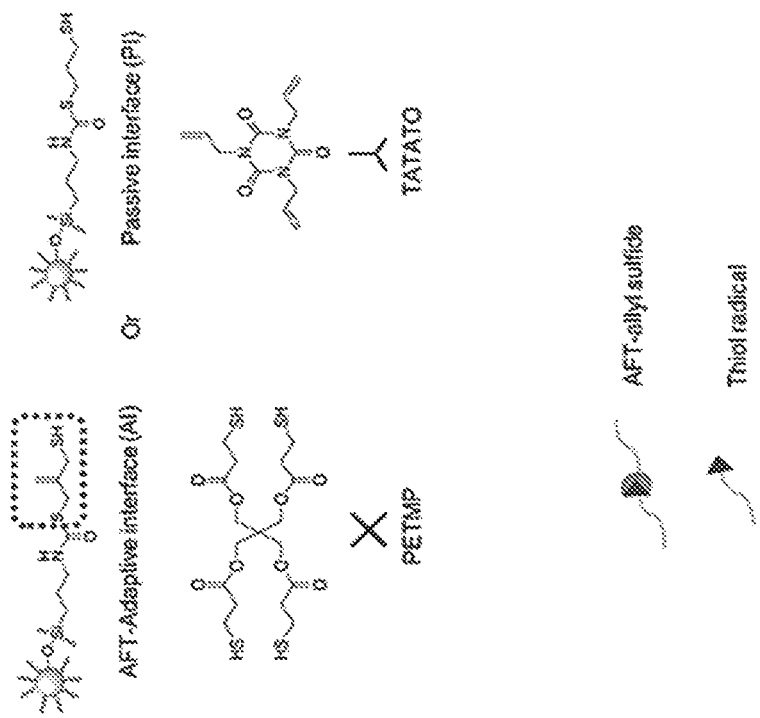

The present invention relates to the discovery of novel polymer-filler compositions displaying stress relaxation at the polymer-filler interface. The teachings in International Application Publication No. WO2018/039331 A1, U.S. Patent Application Publication Nos. US2013/0244179 and US2015/0031782 A1, and U.S. Pat. Nos. 7,943,680 and 8,404,758 are incorporated by reference herein in their entireties.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in polymer chemistry and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "alkene monomer" or "alkene-based substrate" refers to a small molecule or a polymeric molecule comprising at least one reactive alkenyl group. An "alkenyl group" is an unsaturated, linear or branched or cyclic hydrocarbon group consisting at least one carbon-carbon double bond. In certain embodiments, the ene-based substrate comprises at least one alkenyl group (C=C).

As used herein, "covalent adaptable networks" (CANs) are polymeric networks, wherein the polymers can undergo covalent bond reshuffling reactions. Covalent adaptable networks (CANs) thus are cross-linked polymers, capable of relaxing internal stress via bond rearrangement within the networks in response to the application of a triggering stimulus such as light or heat. CANs represent an effective strategy to create polymeric materials that retain certain useful properties of crosslinked networks, yet offer a route towards recycling and remolding through covalent bond reshuffling reactions. In CANs with exchangeable crosslinks, a chain end with an active site attacks a specific moiety on the backbone of the polymer. A short-lived intermediate is formed, which quickly breaks apart in one of several locations to regenerate the original functionalities. The products of this exchange are chemically identical to the original reactants, but directional stress within the network drives the equilibrium towards a particular bond configuration to dissipate chain energy, which leads to macroscopic stress relaxation behavior. Several chemistries have been previously explored for adaptable network polymers, including thermally activated reactions such as transesterification, transamination, and disulfide exchange, base-catalyzed such as thiol-thioester; as well as light-triggered bond rearrangement using a reversible addition-fragmentation chain transfer (RAFT) mechanism.

As used herein, the term "curable" as applied to a material refers to a material comprising at least one functional group that may undergo polymerization. The curable material may be non-polymerized (i.e., non-cured material), or may be submitted to polymerization conditions (such as chemical reagents or physical conditions) that induce polymerization of at least a fraction of the at least one polymerizable functional group (i.e., partially or fully cured material). In one embodiment, polymerization or crosslinking of the curable material results in about 100% consumption of the at least one functional group (i.e., fully cured). In another embodiment, polymerization or crosslinking of the curable material results in less than about 100% consumption of the at least one functional group (i.e., partially cured).

As used herein, "dynamic covalent chemistry" (DCC) refers to a chemistry that involves reversible exchange of bonds between the DCC capable moieties, wherein original bonds are cleaved as new bonds are formed.

As used herein, the term "ene monomer" refers to a monomer comprising at least one reactive alkene group, or a reactive alkene equivalent. Monomers having "-ene" or vinyl functional groups suitable for embodiments of the present invention include any monomer having one, or preferably more functional vinyl groups, i.e., reacting "C=C" or "C≡C" groups. The ene monomer can be selected from one or more compounds having vinyl functional groups. Vinyl functional groups can be selected from, for example, vinyl ether, vinyl ester, allyl ether, norbornene, diene, propenyl, alkene, alkyne, N-vinyl amide, unsaturated ester, N-substituted maleimides, and styrene moieties. Examples of suitable ene monomers include Triallyl-1,3,5-triazine-2,4,6-trione (TATATO); Triethyleneglycol divinyl ether (TEGDVE); Trimethylolpropane diallyl ether; 1,6-heptadiyne; 1,7-octadiyne; and Dodecyl vinyl ether (DDVE) and norbornene monomers.

As used herein, the term "filler" refers to any particle or fiber that is non-reactive/inert to resins, polymer, or to any other component of the composition. In certain embodiments, the filler can be functionalized/derivatized with at least one chemical moiety that can engage in dynamic covalent chemistry (DCC) with the resin or polymer, or the interface thereof.

The terms "mercapto" or "thiol" refer to an —SH substituent, or are used to designate a compound having an —SH substituent.

The term "monomer" refers to any discreet chemical compound of any molecular weight.

As used herein, the term "nanoparticle" is a particle or fiber with a dimensions ranging from about 1 nanometer to 100 nanometers. As used herein, term "nanoparticle" can also describe particle or fiber structures with dimensions ranging up to 1,000 nm. In certain embodiments, nanoparticles often possess physical properties distinct from the properties of the bulk material.

As used herein, the term "orthogonal," as applied to the conditions required to run at least two distinct chemical reactions, indicates that the conditions used to perform one of the chemical reactions do not significantly affect the ability to perform the subsequent other(s) chemical reaction(s). In a non-limiting example, reactions R1 and R2 may be performed in a system, wherein R1 is run first and R2 is run second; reactions R1 and R2 are performed under "orthogonal" conditions if reaction R1 may be performed in the system under conditions that do not affect the ability to subsequently perform reaction R2 in the system.

As used herein, the term "polymer" refers to a molecule composed of repeating structural units typically connected by covalent chemical bonds. The term "polymer" is also meant to include the terms copolymer and oligomers. In certain embodiments, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In certain embodiments, polymerization or crosslinking of at least one functional group results in about 100% consumption of the at least one functional group. In other embodiments, polymerization or crosslinking of at least one functional group results in less than about 100% consumption of the at least one functional group.

As used herein, the term "reaction condition" refers to a physical treatment, chemical reagent, or combination thereof, which is required or optionally required to promote a reaction. Non-limiting examples of reaction conditions are electromagnetic radiation (such as, but not limited to visible light), heat, a catalyst, a chemical reagent (such as, but not limited to, an acid, base, electrophile or nucleophile), and a buffer.

As used herein, the term "reactive" as applied to a specific group indicates that this group under appropriate conditions may take part in one or more reactions as defined in this application.

As used herein, the term "thiol-ene reaction" refers to an organic reaction between a thiol monomer and an ene/yne monomer. In certain embodiments, the ene monomer is an α,β-unsaturated ester, acid, sulfone, nitrile, ketone, amide, aldehyde, or nitro compound (Hoyle, et al., Angew. Chem. Intl Ed., 2010, 49(9):1540-1573); the thiol-ene reaction involving such reactants is known as "thiol-Michael reaction."

As used herein, the term "thiol-ene polymerization" refers to polymerization wherein at least one thiol-ene reaction takes place.

As used herein, the term "Type I photoinitiator" refers to a compound that undergoes a unimolecular bond cleavage upon irradiation to yield free radicals. Non-limiting examples of Type I photoinitiators are benzoin ethers, benzyl ketals, α-dialkoxy-acetophenones, α-hydroxy-alkylphenones, α-amino-alkylphenones and acyl-phosphine oxides.

As used herein, the term "Type II photoinitiator" refers to a combination of compounds that undergo a bimolecular reaction where the excited state of the photoinitiator interacts with a second molecule (often known as "co-initiator") to generate free radicals.

As used herein, the term "alkyl", by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "cycloalkyl", by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl", employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl", employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene. Heteroalkylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies.

As used herein, the term "substituted alkyl", "substituted cycloalkyl", "substituted alkenyl", "substituted alkynyl", "substituted alkylene", "substituted alkenylene" or "substituted alkynylene" means alkyl, cycloalkyl, alkenyl, alkynyl, alkylene, alkenylene, alkynylene as defined above, substituted by one, two or three substituents selected from the group consisting of $C_1$-$C_{10}$ alkyl, halogen, =O, —OH, alkoxy, tetrahydro-2-H-pyranyl, —$NH_2$, —N($CH_3$)$_2$, (1-methyl-imidazol-2-yl), pyridin-2-yl, pyridin-3-yl, pyridin-4-yl, —C(=O)OH, trifluoromethyl, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —N($CH_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of C$_{1-6}$alkyl, —OH, C$_{1-6}$alkoxy, halo, amino, acetamido and nitro. As used herein, where a substituent is an alkyl or alkoxy group, the carbon chain may be branched, straight or cyclic, with straight being preferred.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: CAN(s) =covalent adaptable network(s); AFT=addition fragmentation chain transfer; DCC=dynamic covalent chemistry; AI=adaptive interface; PI=passive interface; NP=nanoparticle; SNP=silica nanoparticle; FT-IR=Fourier transform infrared spectroscopy; TE=thioester; TTE=thiol-thioester; PETMP=pentaerythritol tetra(3-mercaptopropionate); TATATO=1,3,5-triallyl-1,3,5-triazine-2,4,6(1H,3H,5H)-trione; I819=(bis(2,4,6-trimethylbenzoyl)-phenylphosphineoxide); I651=2,2-dimethoxy-1,2-diphenylethan-1-one; AFT-DVE=2-methylene-propane-1,3-di(thioethyl vinyl ether); IR=infrared; MPa=megapascal; NMR=nuclear magnetic resonance spectroscopy; UV=ultraviolet.

Compounds and Compositions

In one aspect the invention provides a nanoparticle (NP) functionalized with at least one linker comprising at least one of the following groups: (a) at least one RAFT functionality such as allyl sulfide and/or trithiocarbonate group or (b) at least one multifunctional thioester of formula (I),

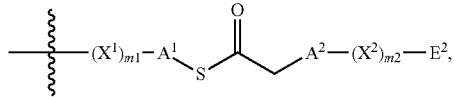
(I)

wherein in (I):
$A^1$ and $A^2$ are each independently selected from the group consisting of optionally substituted $C_1$-$C_{15}$ alkylene, optionally substituted $C_2$-$C_{15}$ alkenylene, optionally substituted $C_2$-$C_{15}$ alkynylene, optionally substituted $C_2$-$C_{15}$ heteroalkylene, optionally substituted $C_2$-$C_{15}$ heteroalkenylene and optionally substituted $C_2$-$C_{15}$ heteroalkynylene;
$E^2$ is selected from the group consisting of:

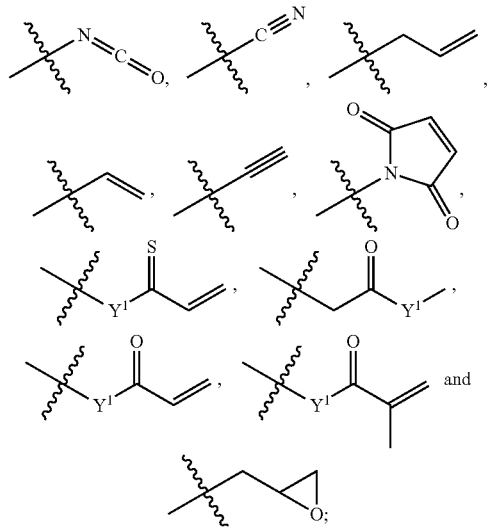

each instance of $Y^1$ is independently selected from the group consisting of O and $NR^1$; and each instance of $R^1$ being independently selected from the group consisting of H and $C_1$-$C_6$ alkyl;
m1 is 0 or 1;
m2 is 0 or 1;

$X^1$ is

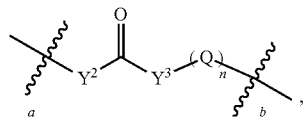

wherein:
bond a is to $A^1$,
Q is $CH_2$ or

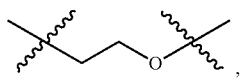 [SMILES: *CCO*]

and
n is 0, 1, 2, 3, 4, 5 or 6;
$X^2$ is

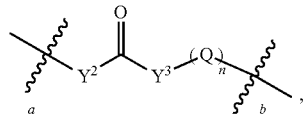

wherein:
bond a is to $A^2$,
bond b is to $E^2$,
Q is $CH_2$ or

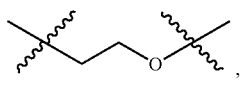 [SMILES: *CCO*]

and
n is 0, 1, 2, 3, 4, 5 or 6;
each instance of $Y^2$ and $Y^3$ is independently selected from the group consisting of $CR^1$, O and $NR^1$; and
each instance of $R^1$ is independently selected from the group consisting of H and $C_1$-$C_6$ alkyl.

In certain embodiments, the group (b) comprises a linker of formula (Ia):

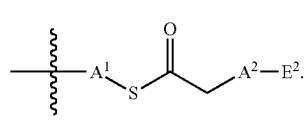
(Ia)

In certain embodiments, the group (b) comprises a linker selected from the group consisting of:

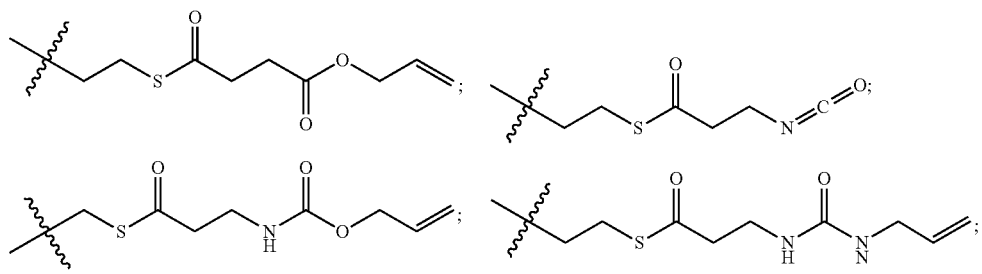

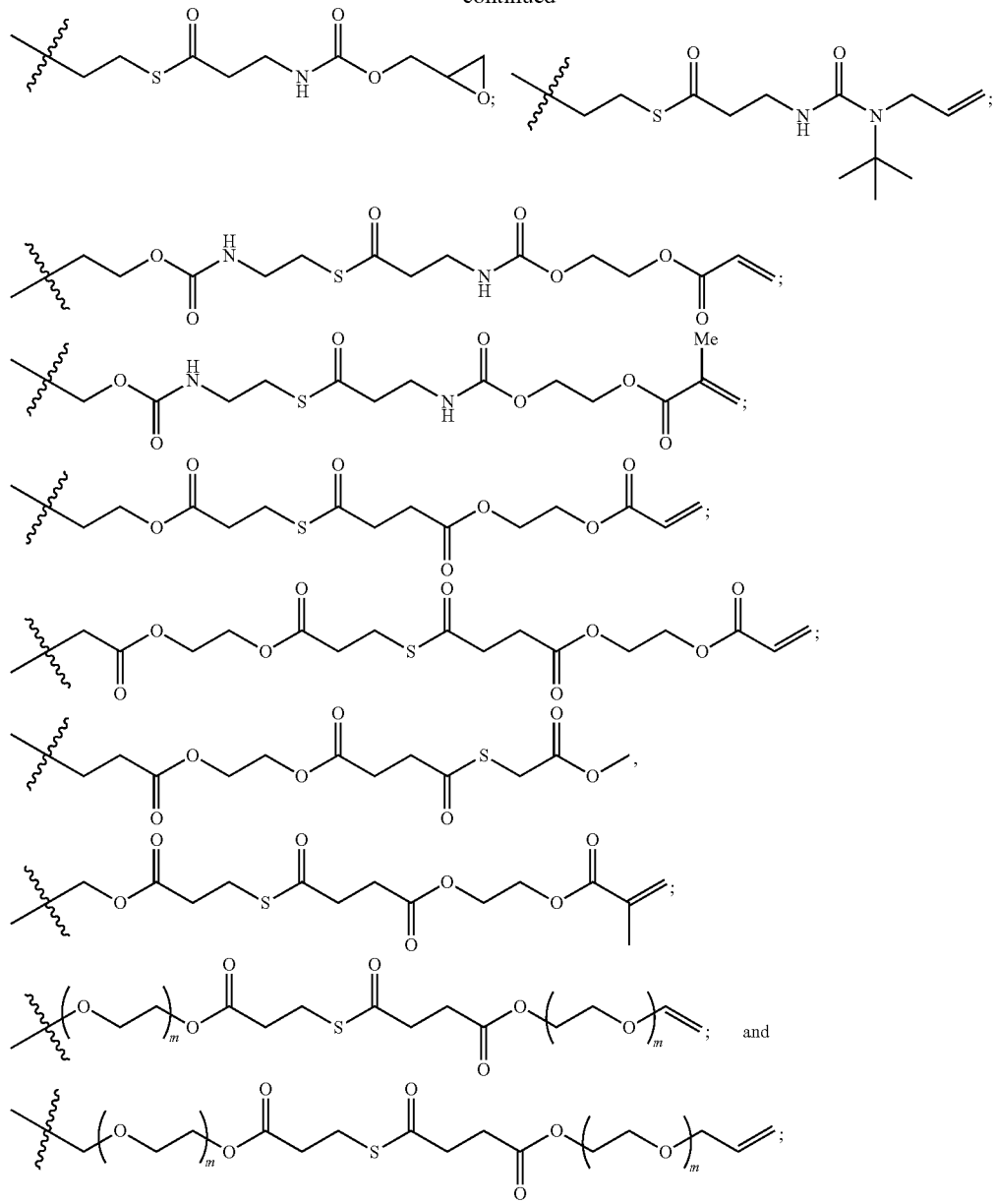

wherein each occurrence of m is independently selected from the group consisting of 0, 1, 2, 3, 4, 5, and 6.

In certain embodiments, group (a) comprises SCH$_2$C(=CH$_2$)CH$_2$SH.

In another aspect, the invention provides a composition displaying stress relaxation at polymer-filler interface. In certain embodiments, the composition comprises a polymer and a filler comprising at least one nanoparticle (NP) of the invention functionalized with at least one chemical moiety capable of engaging in dynamic covalent chemistry (DCC) with the polymer at the polymer-filler interface.

In certain embodiments, the composition further comprises one or more fillers. In other embodiments, the filler is used to modulate the viscosity, hydrophilicity and stiffness (rubbery modulus) of the unpolymerized or polymerized composition. Non-limiting examples of fillers include inorganic filler compounds such as barium, ytterbium, strontium, zirconia silicate, amorphous silica. The filler may be silanized and typically presented in the form of particles with a size ranging from 0.01 to 5.0 micrometers. In yet other embodiments, the filler is a hydrophobic fumed silica. In yet other embodiments, the hydrophobic fumed silica filler is composed of nanoparticles or nanoclusters.

A nanoparticle is defined as any particle less than 100 nanometers (nm) in diameter. A nanocluster is an agglomeration of nanoparticles. In one embodiment, utilization of nanoclusters in a nanosized filler can be exploited to increase the load and improve some mechanical properties. Examples of suitable filling materials include but are not limited to, barium glass, ytterbium nanoglasses and nanoclusters, fumed silica, silica, silicate glass, quartz, barium silicate, strontium silicate, barium borosilicate, strontium borosilicate, borosilicate, lithium silicate, lithium alumina silicate, amorphous silica, ammoniated or deammoniated calcium phosphate and alumina, zirconia, tin oxide, and titania. Some of the aforementioned inorganic filling materials and methods of preparation thereof are disclosed in U.S. Pat. Nos. 4,544,359 and 4,547,531; pertinent portions of each of which are incorporated herein by reference. In certain embodiments, the filler is a mixture of barium glass, ytterbium nanoglasses and nanoclusters, and fumed silica. In other embodiments, the filler is 85 wt % 0.5 micron barium glass, 10 wt % ytterbium 40 nm nanoglass and nanoclusters, 2.5 wt % Aerosil fumed silica, and 2.5 wt % Cabosil fumed silica. In yet other embodiments, the filler is a mixture of 90% 0.4 μm Schott glass and 10 wt % Aerosol OX-50. The above described filler materials may be combined with the resins of the disclosure to form a composite material (such as, but not limited to, dental composite material) with high strength along with other beneficial physical and chemical properties.

In certain embodiments, suitable fillers are those having a particle size in the range from about 0.01 to about 5.0 micrometers, mixed with a silicate colloid of about 0.001 to about 0.07 micrometers. The filler may be utilized in the filled resin compositions of the disclosure in the amount of from about 40 wt % to about 90 wt %; for example about 60 wt % to 85 wt %; for example about 70 wt % to about 80 wt % of the total weight of the composition. In one specific embodiment, 72.5 wt % filler is utilized in the filled resin composition. In another specific embodiment, 60 wt % filler is utilized in the filled resin composition.

In certain embodiments, the filler comprises at least one selected from the group consisting of silica, carbon, metal oxide, clay, fiber, glass, ceramic, and polymeric filler.

In certain embodiments, the composition comprising the nanoparticles of the invention displays superior mechanical properties compared to the composition containing control nanoparticles, which do not comprise thiol or thioester groups.

In certain embodiments, the monomers forming the polymer can interact with each other to form a polymer via any possible polymerization mechanism. In certain embodiments, the polymer comprises at least one monomer capable of engaging in DCC with the at least one functionalized nanoparticle of the invention.

In certain embodiments, the polymer further comprises at least one multifunctional monomer capable of engaging in DCC with at least one other monomer in the polymer to form a covalent adaptive network (CAN).

In certain embodiments, the DCC comprises at least one selected from the group consisting of reversible addition-fragmentation chain transfer (RAFT) mechanism, thiol-thioester exchange (TTE), Diels-Alder reaction, transesterification, transamination, and disulfide exchange.

In certain embodiments, the DCC at the polymer-filler interface is orthogonal to the DCC within the polymer. In certain embodiments, the DCC occurs at the polymer-particle interface. In certain other embodiments, the DCC occurs between the monomers within the polymer. In certain embodiments, the DCC within the polymer is activated during the curing process to reduce shrinkage stress. In certain embodiments, the DCC at the polymer-particle interface can be activated at later stage in the cured composite to reduce interfacial stress. This approach enables the stress relaxation in both locations within the composite resin matrix and at the polymer-particle interface with will provide long term stress relaxation.

In certain embodiments, the NP is functionalized with at least one linker that comprises a chemical moiety that reacts with at least one functional group of the polymer through DCC chemistry to form a covalent bond.

In certain embodiments, the CAN is formed through one or more processes selected from the group consisting of thiol-ene polymerization, thiol-alkyne polymerization, thiol-acrylate polymerization, thiol-methacrylate, acrylate polymerization, methacrylate polymerization, styrene polymerization, alcohol-isocyanate polymerization, thiol-isocyanate polymerization, thiol-epoxide polymerization, thiol-isothiocyanate polymerization, thiol-halide polymerization, thiol-malemide, thiol-activated ester polymerization, copper-catalyzed azide alkyne polymerization, strain-promoted azide alkyne polymerization, and epoxide-carboxylic acid polymerization.

In certain embodiments, the polymer comprises at least at least one thiol monomer or one multifunctional thiol monomer.

In certain embodiments, the at least one thiol monomer is selected from the group consisting of

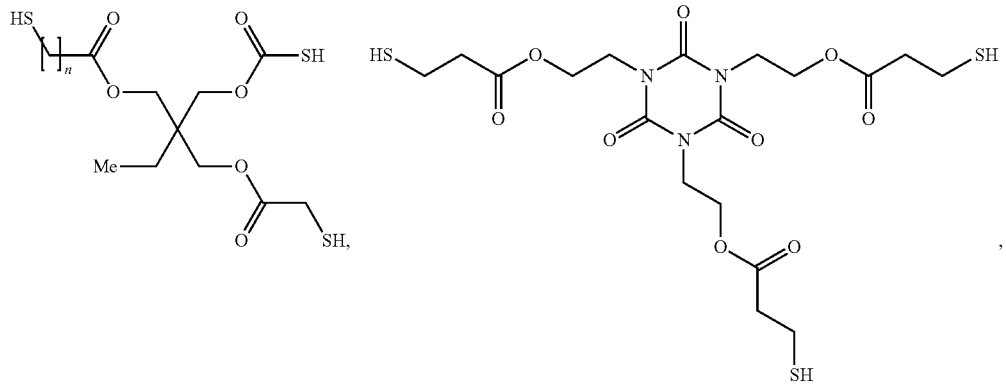

-continued

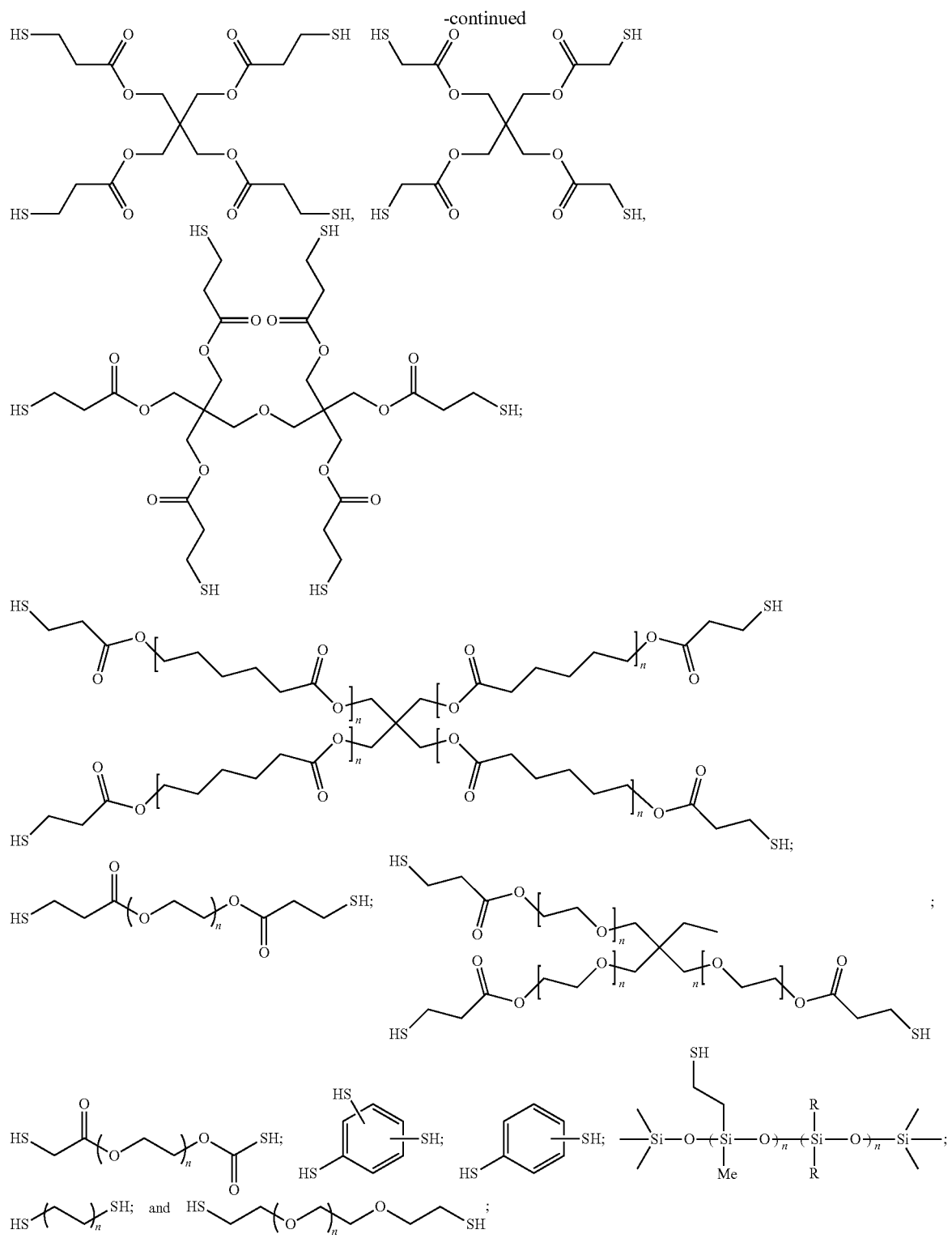

wherein each instance of n is independently an integer from 0 to 500.

In certain embodiments, the at least one multifunctional thiol monomer is selected from the group consisting of: pentaerythritol tetramercaptopropionate (PETMP), ethylene glycol bis(3-mercaptopropionate) (EGBMP), trimethylolpropane tris(3-mercaptopropionate)(TMPMP), 2,4,6-trioxo-1,3,5-triazina-triy (triethyl-tris (3-mercapto propionate); 1,2-ethanedithiol, 1,3-propanedithiol, 1,4-butanedithiol; 1,5-pentanedithiol; 1,6-hexanedithiol; 1,8-octanedithiol, 1,9-nonanedithiol, 1,11-undecanedithiol, 1,16-hexadecanedithiol; 2,5-dimercaptomethyl-1,4-dithiane; pentaerythritol tetramercaptoacetate; trimethylolpropane trimercaptoacetate, glycol dimercaptoacetate, 2,3-dimercapto-1-propanol, DL-dithiothreitol, 2-mercaptoethylsulfide, 2,3-(dimercaptoethylthio)-1-mercaptopropane; 1,2,3-trimercaptopropane, toluenedithiol, benzenedithiol, biphenyldithiol, benzenedimethanethiol, xylylenedithiol, 4,4'-dimercaptostilbene, and glycol dimercaptopropionate and any combinations thereof.

In certain embodiments, the polymer is selected from the group consisting of thiol-ene, epoxy-amine, polyurethane, thio-urethane, acrylate, methacrylate, and azide-alkyne.

In certain embodiments, the thiol-ene polymer comprises an ene monomer selected from a group consisting of ethylene glycoldi(meth)acrylate, ethoxylated bisphenol-A dimethacrylate (EBPADMA), tetraethyleneglycoldi(meth)acrylate (TEGDMA), poly(ethylene glycol) dimethacrylates, the condensation product of bisphenol A and glycidyl methacrylate, 2,2'-bis-[4-(3-methacryloxy-2-hydroxy propoxy)-phenyl]propane (BisGMA), hexanediol di(meth)acrylate, tripropylene glycol di(meth)acrylate, butanediol di(meth)acrylate, neopentyl glycol di(meth) acrylate, diethylene glycol di(meth)acrylate, triethylene glycol di(meth) acrylate, dipropylene glycol di(meth)acrylate, trimethylolpropane triacrylate (TMPTA), di(trimethylolpropane) tetraacrylate (DTPTA), divinyl sulfone (DVS), propargyl acrylate, 6-azidohexyl acrylate, [2-(acryloyloxy)ethyl]trimethylammonium chloride, acrylic acid, 2-(4-benzoyl-3-hydroxyphenoxy)ethyl acrylate, 3-sulfopropyl acrylate potassium salt, 2-hydroxyethyl acrylate and 2-(dimethylamino)ethyl acrylate.1,1'-(Methylenedi-4,1-phenylene)bismaleimide, 1,4-di(maleimido)butane, N,N'-phenylenedimaleimide, N,N'-methylenebisacrylamide, and any combinations thereof.

In certain embodiments, the thiol-ene polymer comprises an ene monomer selected from a group consisting of triallyl-1,3,5-triazine-2,4,6-trione (TATATO), triethyleneglycol divinyl ether (TEGDVE), trimethylolpropane diallyl ether, dodecyl vinyl ether (DDVE), 1,6-heptadiyne, 1,7-octadiyne, bis-2,2-[4-(2-[norborn-2-ene-5-carboxylate]ethoxy) phenyl] propane (BPAEDN), 1,6-hexanediol di-(endo,exo-norborn-2-ene-5-carboxylate) (HDDN), trimethylolpropane tri-(norborn-2-ene-5-carboxylate) (TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), di(trimethylolpropane) tetra-(norborn-2-ene-5-carboxylate) (DTMPTN), and any combinations thereof.

In certain embodiments, the thiol-ene polymer further comprises 2-methylene-propane-1,3-di (thioethyl vinyl ether).

In certain embodiments, the linker comprise group (a) and the polymer comprises at least one free sulfur radical from the at least one multifunctional thiol monomer. The resulting DCC at the polymer-filler interface is RAFT.

In certain embodiments, the linker comprise group (b) and the polymer comprises at least one free thiol from the at least one multifunctional thiol monomer. The resulting DCC at the polymer-filler interface is TTE.

In certain embodiments, the polymer comprise group (a) and the linker comprises at least one free sulfur radical from the at least one multifunctional thiol monomer. The resulting DCC at the polymer-filler interface is RAFT.

In certain embodiments, the polymer comprise group (b) and the linker comprises at least one free thiol from the at least one multifunctional thiol monomer. The resulting DCC at the polymer-filler interface is TTE.

In certain embodiments, the thiol-ene polymer comprises PETMP and 1,3,5-triallyl-1,3,5-triazine-2,4,6(1H,3H,5H)-trione (TATATO)alkene. In certain embodiments, the ratio of PETMP to TATATO is about 1:1.

In certain embodiments, the thiol-ene polymer further comprises 2-methylene-propane-1,3-di (thioethyl vinyl ether) AFT-DVE monomer to promote bond exchange to form a covalent adaptable network (CAN) polymer.

In certain embodiments, the composition further comprises at least one polymerization initiator selected from the group consisting of a photoinitiator, a thermal initiator, and a redox initiator.

In certain embodiments, the DCC functionalities are activated through at least one reaction selected from the group consisting of photoinitiation, thermal initiation, and redox initiation.

In certain embodiments, the at least one photoinitiator is activated upon exposure to light in at least one range selected from the group consisting of IR, visible, and UV.

In certain embodiments, the photoinitiator is selected from the group consisting of Type-1 and Type-2 photoinitiators. In certain embodiments, the photoinitiator is a compound belonging to a class selected from the group consisting of acyl phosphines, ketones, diimidazoles, acyl germaniums, thioketones, dithiocarbonates, trithiocarbonates, camphorquinones and camphoramines. In certain embodiments, the at least one photoinitiator is selected from the group consisting of: acetophenone, benzophenone, 2-phenylacetophenone, 2,2-dimethoxy-2-phenylacetophenone, Bis(2,4,6-trimethylbenzoyl)-phenylphosphineoxide, 2-Hydroxy-4-(2-hydroxyethoxy)-2-methylpropiophenone, 2-methyl-(4-methylthienyl)-2-morpholinyl-1-propan-1-one, Diphenyl(2,4,6-trimethylbenzoyl)phosphine oxide, Ethyl (2,4,6-trimethylbenzoyl) phenyl phosphinate, lithium phenyl-2,4,6-trimethylbenzoylphosphinate,

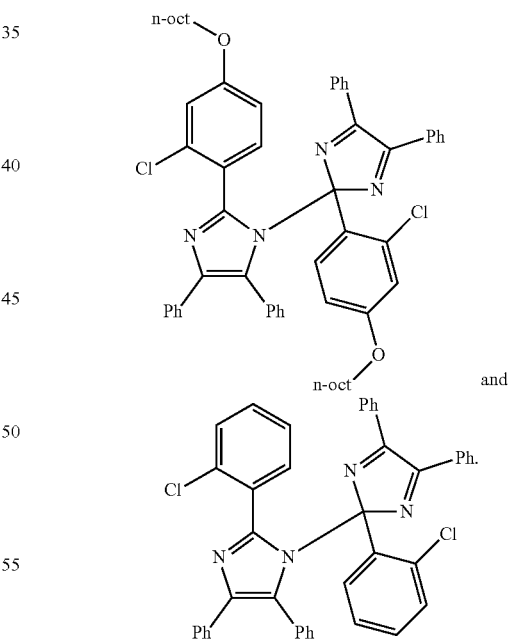

and

In certain embodiments, the at least one thermal initiator is reactive upon exposure to temperatures of about 30° C. to about 200° C.

In certain embodiments, the at least one thermal initiator is a compound selected from the group consisting of tert-Amyl peroxybenzoate, 4,4-Azobis(4-cyanovaleric acid), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis(tert-butylperoxy)-2,5-dimethylhexane, 2,5-Bis(tert-butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, cumene hydroperoxide, cyclohexanone peroxide, dicumyl peroxide, lauroyl peroxide, 2,4-pentanedione peroxide, peracetic acid, and potassium persulfate.

In certain embodiments, the at least one redox initiator is selected from the group consisting of: sodium iodide/hydrogen peroxide, potassium iodide/hydrogen peroxide, benzoyl peroxide/dimethyaniline, benzoyl peroxide/N,N-dimethyl p-toluidine, benzoyl peroxide/4-N,N-dimethylaminophenethyl alcohol, benzoyl peroxide/ethyl 4-dimethylamino benzoate, glucose oxidase/oxygen/iron(II) sulfate; and copper (II) sulfate/sodium ascorbate.

In certain embodiments, the composition further comprises a catalyst selected from the group consisting of a nucleophile and a base.

In certain embodiments, continuous re-shuffling of covalent bonds in the presence of a base catalyst and excess thiol can be achieved in case of TTE. In certain embodiments, the TTE remains active throughout the composite lifetime. In certain embodiments, the continuous TTE induces interfacial relaxation in opaque materials without concern for depleting a source of radicals. In certain embodiments, as a result of continuous TTE the composite displays improved fatigue performance and fracture toughness throughout the material's lifetime.

In certain embodiments, the nucleophile is selected from the group consisting of quinuclidine, 1,4-diazabicyclo[2.2.2]octane (DABCO), 4-Dimethylaminopyridine (DMAP), IMes, IPr, Ender's carbene, PPh3 P(nBu)3, P(tBu)3, PCy3, and PMe3.

In certain embodiments, the base is capable of deprotonating at least about 10% of the thiol groups in the composition.

In certain embodiments, the base is selected from the group consisting of an alkylthiolate salt, tetramethylguanidine (TMG), 1,8-Diazabicyclo[5,4,0]undec-7-ene (DBU), N,N-Diisopropylethylamine (DIPEA or Hunig's base), 4-tert-butyl pyridine, triethylamine (TEA), and and N,N,N',N'',N''-pentamethyldiethylenetriamine (PMDETA).

In certain embodiments, the base is selected from the group consisting of a photo-activatable base and a thermal-activatable base.

In certain embodiments, the photo-activatable base is a compound selected from the group consisting of:

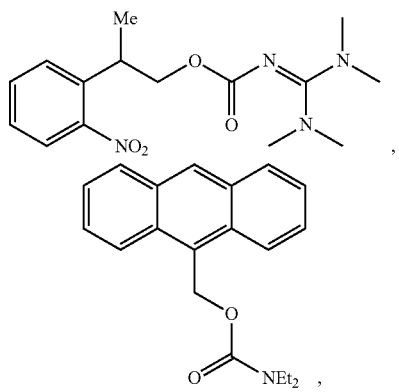

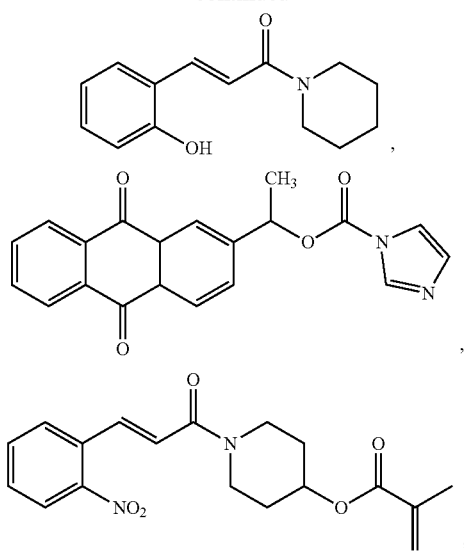

1,2-Diisopropyl-3-[Bis (dimethylamino) methylene]guanidium 2-(3-benzoylphenyl)propionate, 1,2-Dicyclohexyl-4,4,5,5-tetramethyl biguanidium n-butyltriphenylborate, and (Z)-{[Bis(dimethylamino) methylidene]amino}-N-cyclohexyl(cyclohexylamino)methaniminium tetrakis(3-fluorophenyl)borate.

In certain embodiments, the thermal-activatable base is selected from the group consisting of:

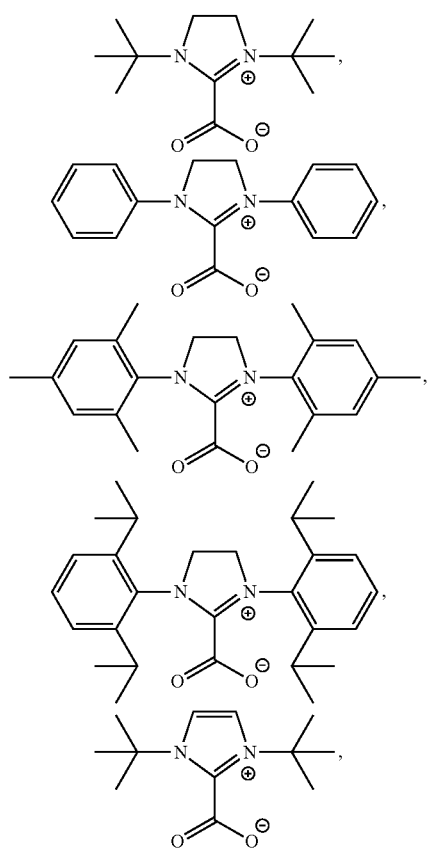

37
-continued
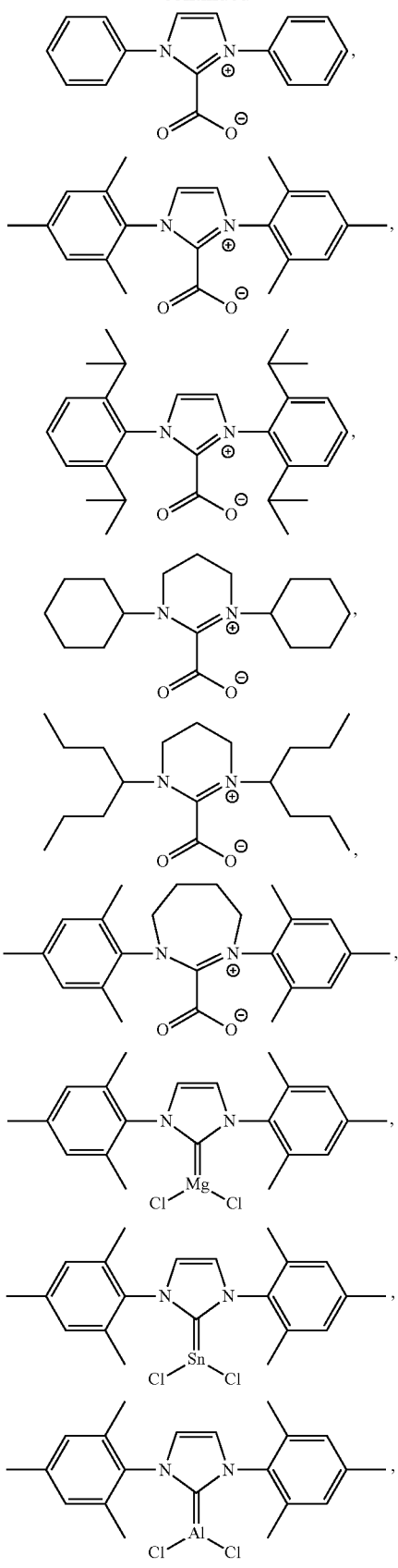
38
-continued
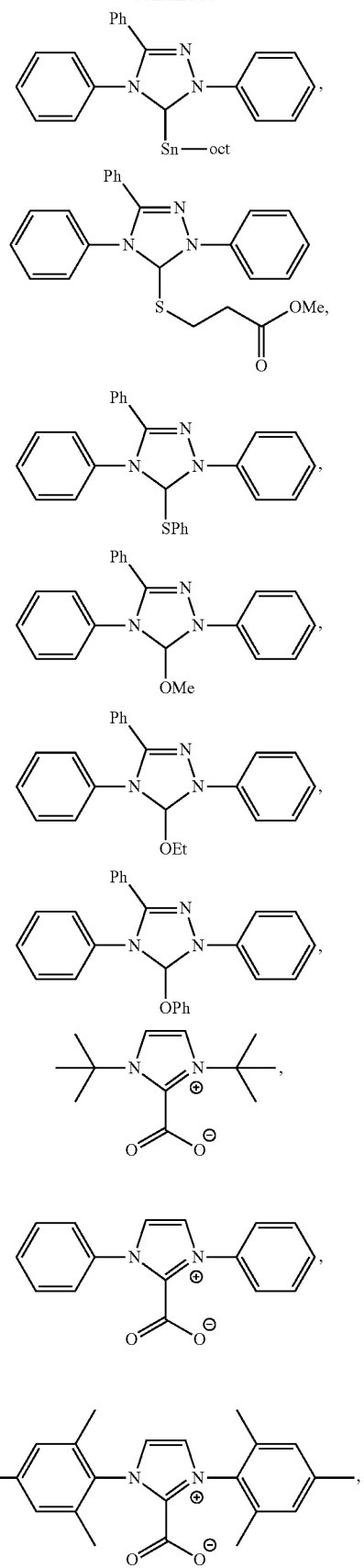

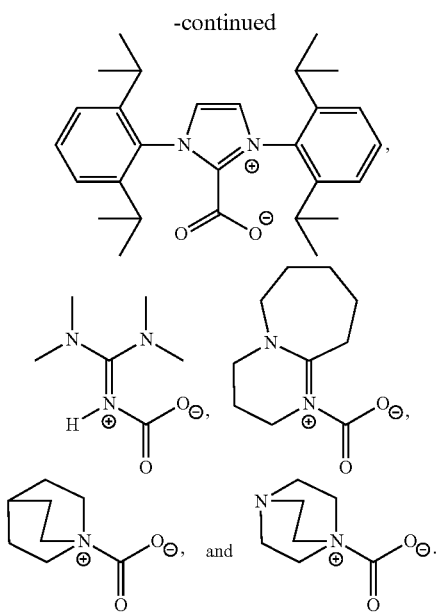

In certain embodiments, the composite comprises about 5% to about 50% of the at least one NP by weight.

In certain embodiments, the fracture toughness of the composite increases with increasing weight fraction of the at least one NP. In certain embodiments the toughness of the composite containing the at least one functionalized NP is greater than that of a composite that contains a least one non-functionalized NP.

In certain embodiments, the tensile strength of the composite increases with increasing weight fraction of the at least one NP. In certain embodiments the tensile strength of the composite containing the at least one functionalized NP is greater than that of a composite that contains a least one non-functionalized NP.

In yet another aspect, the invention provides a dental restorative material comprising the composition of the invention, wherein 15 wt % of a thioester filler is incorporated in composite comprising 70/30 BisGMA/TEGDMA, 15 wt % PETMP, 7.5 wt % DABCO, 1 wt % I819.

In certain embodiments, the thioester filler containing dental composite displays superior elastic modulus and flexural strength compared to the composite having control (non-thioester) filler.

In certain embodiments, the thioester filler containing dental composite displays shrinkage stress reduction via thioester-based CANs at the particle-polymer interface of dental composites.

Methods

In yet another aspect, the invention provides a method of forming the composition of the invention such that the composition displays stress relaxation at polymer-filler interface. In certain embodiments, the method comprises combining at least one nanoparticle (NP) with at least one multifunctional thiol monomer, at least one ene monomer, and at least one polymerization initiator to form an uncured polymer-filler composite. In other embodiments, the method further comprises activating the at least one polymerization initiator, thereby at least partially curing the polymer-filler composite.

In certain embodiments, the at least one nanoparticle is as described elsewhere herein.

In certain embodiments, the multifunctional thiol monomer is as described elsewhere herein.

In certain embodiments, the at least one ene monomer is as described elsewhere herein.

In certain embodiments, the alkene is as described elsewhere herein.

In certain embodiments, the polymerization initiator is as described elsewhere herein.

In certain embodiments, the method further comprises using a catalyst selected from the group consisting of a nucleophile and a base. In certain embodiments, the nucleophile or the base is as described elsewhere herein.

In certain embodiments the method further comprises postcuring the poymer-filler composite. In certain embodiments, the samples are post cured at a temperature in the range of about 50° C. to about 150° C. In certain embodiments, the post curing is lasts from about 2 hours to about 40 hours.

Kits

The invention includes a kit comprising a composition of the invention comprising at least one, or all of the following: (a) at least one nanoparticle of the invention; (b) at least one multifunctional thiol monomer; (c) at least alkene monomer.

In certain embodiments, the kit further comprises at least one base or a nucleophile, as described elsewhere herein. In certain embodiments, the base is a photo-activatable base or thermal-activatable base, as described elsewhere herein. In other embodiments, the kit further a polymerization initiator, selected from the group consisting of a photoinitiator, a thermal initiator and a redox initiator. In yet other embodiments, the kit further comprises a light source capable of producing light sufficient to activate at least one of the photoinitiator, the photo-activatable base and the photo-activatable acid. In other embodiments, the kit further comprises a heat source capable of producing heat sufficient to activate at least one of the thermal initiator, the thermal-activatable base and the thermal-activatable acid. The instructional material included in the kit comprises instructions for forming the composition of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application. The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Triallyl-1,3,5-triazine-2,4,6-(1H,3H,5H)-trione (TATATO), pentaerythritol tetrakis(3-mercaptopropionate (PETMP), 3-(triethoxysilyl)propyl isocyanate, 1,3-propanedithiol, 3-chloro-2-chloromethyl-1-propene, potassium ethyl xanthogenate, ethylene diamine, and propylamine were purchased from Sigma-Aldrich. Irgacure 819 (bis(2,4, 6-trimethylbenzoyl)-phenylphosphineoxide) and I651 (2,2-Dimethoxy-1,2-diphenylethan-1-one) both were obtained from BASF. Schott glass (mean particle size 40 nm) untreated were donated by Evonik Silicas, and used as the inorganic fillers. Prior to implementation and as described later, these fillers were subsequently functionalized with thiol group for inclusion and copolymerization in the composite. All chemicals were used as received.

Methods:

Synthesis of 2-Methylene-1,3-Propanedithiol:

Allyl dithiol was synthesized according to a previously reported method (Evans, et al., 2000, Macromolecules 33(18):6722-6731). In a 250 mL round-bottom flask equipped with a magnetic stir bar, 5.00 g (40.0 mmol, 1.00 equiv) of 3-chloro-2-chloromethyl-1-propene and 14.1 g (88.0 mmol, 2.20 equiv) of potassium ethyl xanthogenate were dissolved into 130 mL of absolute ethanol and stirred overnight at room temperature. After 16 h, the reaction mixture was concentrated in vacuo and dissolved in ethyl ether (200 mL). The organic phase was washed with water (3×100 mL) and saturated brine (1×100 mL). The combined organics were dried over $Na_2SO_4$, filtered, and concentrated in vacuo to yield a yellow liquid that was used without further purification in the next step.

Into a 50 mL three-necked round-bottomed flask, equipped with a magnetic stir bar, 5.00 g (16.9 mmol, 1.00 equiv) of the previously obtained yellow liquid was dripped slowly via an addition funnel into a stirring mixture of 8.40 mL of ethylene diamine, maintaining the temperature of the reaction mixture below 30° C. After addition of the reactant was completed (30 min), the reaction was stirred for 4 h at room temperature and slowly poured onto 200 g of ice mixed with 16 mL of sulfuric acid in an Erlenmeyer flask with vigorous stirring. The aqueous phase was extracted with ether (3×~150 mL) and the combined organics were washed with a 1 M aqueous solution of hydrochloric acid (1×~100 mL) followed by a saturated solution of brine (1×~100 mL). The organic phase was then dried over $Na_2SO_4$, filtered, and concentrated in vacuo to yield a pale yellow liquid. The obtained oil was purified with vacuum distillation to give 1.90 g (40% yield, over two steps) of a foul smelling, colorless liquid. $^1$H NMR (400 MHz, chloroform-d, δ): 5.02 (p, 2H), 3.38 (dt, 4H), 1.51 (d, 2H). $^{13}$C NMR (101 MHz, chloroform-d, δ): 147.39, 113.32, 28.15.

Synthesis of Allyl Sulfide (AFT) Based Silane:

A solution of 3-(triethoxysilyl)propyl isocyanate 5.00 g (20.2 mmol, 1.00 equiv) in 200 mL THF with 5 mol % triethylamine as a base catalyst (1.00 mmol, 0.10 g) was added in a round bottom flask and purged under nitrogen. The reaction mixture was allowed to stir for 5 min, followed by a dropwise addition of 2-methylene-1,3-propanedithiol 6.08 g (50.5 mmol, 2.50 equiv), then allowed the reaction mixture to stir at room temperature for 24 h. THF was evaporated and the obtained product was purified by column chromatography using a hexane/ethyl acetate mixture (8:2) as eluent and dried in vacuo as a colorless oil with 70% yield. $^1$H NMR (400 MHz, chloroform-d, δ): 0.64 (m, 2H), 1.25 (t, 9H), 1.49 (d, 1H), 1.66 (p, 2H), 3.23 (m, 2H), 3.31 (q, 2H), 3.36 (dt, 2H), 3.84 (q, 6H), 5.07 (p, 2H), 5.78 (s, 1H); $^{13}$C NMR (101 MHz, chloroform-d, δ): 7.73, 14.21, 18.30, 24.13, 31.24, 33.61, 43.40, 58.53, 60.38, 77.23, 117.64, 137.73, 164.24.

Synthesis of the Control Non-AFT Silane:

The synthesis of the control non-AFT silane is analogous to the procedure described above for the allyl sulfide (AFT) based silane, where the commercially available 1,3-propanedithiol replaces the 2-methylene-1,3-propanedithiol in the synthesis above. $^1$H NMR (400 MHz, chloroform-d, δ): 0.64 (m, 2H), 1.24 (t, 9H), 1.35 (t, 1H), 1.66 (p, 2H) 1.94 (m, 2H), 2.68 (q, 2H), 3.02 (t, 2H), 3.31 (q, 2H), 3.84 (q, 6H), 5.78 (s, 1H); $^{13}$C NMR (101 MHz, chloroform-d, δ): 7.73, 14.21, 18.30, 22.98, 23.08, 28.24, 34.53, 43.66, 58.53, 60.38, 77.23, 166.70.

Synthesis of the TE-SNPs

Figure 2A:
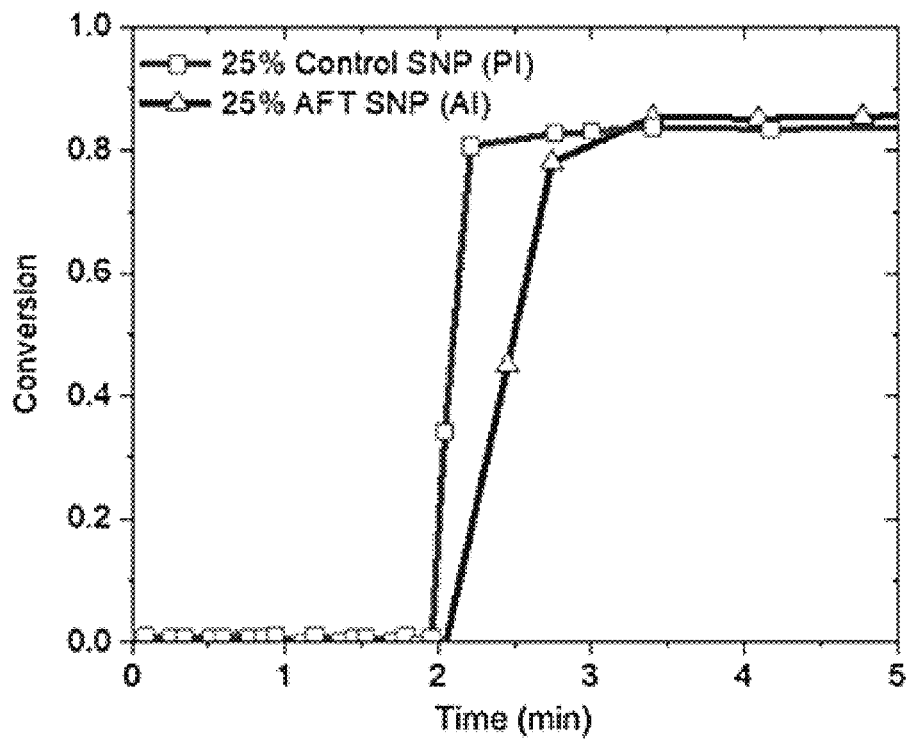
FIGS. 2A-2C are graphs showing polymerization kinetics, polymerization stress, and the final polymerization shrinkage stress for both PI (squares) and AI (triangles). Polymerization kinetics for both PI (squares) and AI (triangles) as measured by FT-NIR (FIG. 2A). In situ polymerization stress for a 1:1 PETMP/TATATO sample with 25 wt % of both control SNPs to generate PI (squares) and AFT SNPs to generate AI (triangles) (FIG. 2B). The final polymerization stress taken after 10 min reaction time for both PI (squares) and AI (triangles) composites as a function of SNPs weight fraction (FIG. 2C). All samples were placed between two quartz rods, previously treated with a thiol-functional silane and irradiated for 2 min at ambient temperature with 400-500 nm light at 50 mW/cm$^2$ following 2 min in the dark to establish a baseline measurement.

TE-SNPs were synthesized by functionalizing nanoparticles with 3-mercaptopropyl trimethoxysilane followed by subsequent thiol-Michael reaction of the thiolated particles with monoacrylate thioester (2.5 equiv) in the presence of triethylamine (5 equiv). Modified fillers were characterized by thermogravimetric analysis (TGA) and diffuse reflectance IR spectroscopy. Initial experiments employing thioester-functionalized SNP with 10 wt. % particles loading in photopolymerizable resins were performed using a formulation consisting of a triene monomer (TATATO) and a tetrathiol (PETMP) with 10% excess thiol (FIG. 2A).

Synthesis of 2-methylpropane-1,3-di(thioethyl vinyl ether) (MeDTVE) and 2-methylene-propane-1,3-di(thioethyl vinyl ether) (MDTVE) followed the procedure found in Kloxin, et al., 2009, Macromolecules 42(7):2551-2556.

Figure 11:
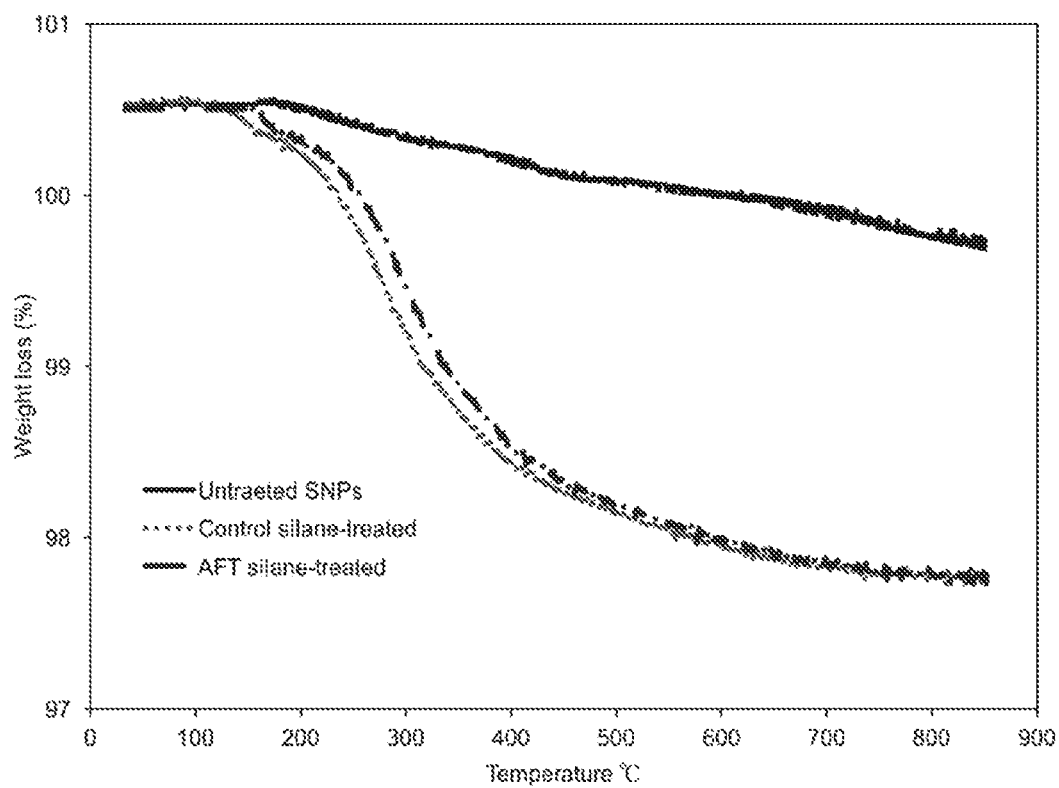
FIG. 11 is a graph showing thermogravimetric analysis on glass microparticles before and after silanization with AFT silane (AI) and control silane (PI). The 2 weight % difference between treated and untreated particles suggests successful silane grafting on the glass surface. Based on this result, calculation yields approximately $1.03 \times 10^{-6}$ mole of AFT silane per m$^2$ on the nanoparticle surface and $1.05 \times 10^{-6}$ mole of control silane per m$^2$ on the nanoparticle surface.
Figure 12:
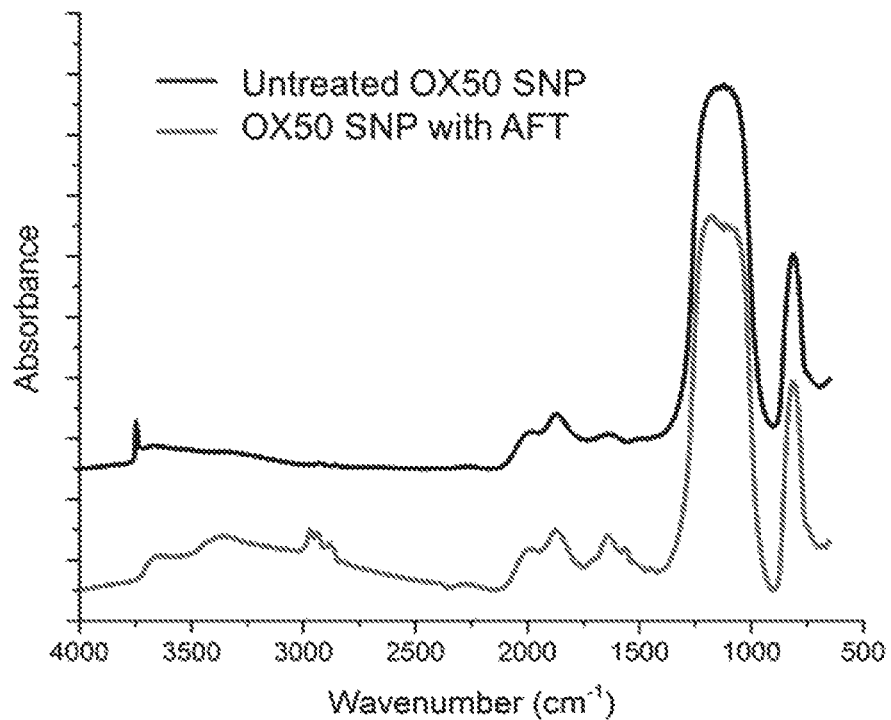
FIG. 12 is a graph showing diffuse reflectance infrared fourier transform spectroscopy (DRIFTS) analysis of untreated (top, line) and AFT functionalized (bottom, line) glass nanoparticles. Disappearance of silanol group is evident at 3745 cm$^{-1}$. Also, the IR signals of the organic layer grafted on the particle surface are apparent in the range 2800-3100 cm$^{-1}$.

Filler Functionalization:

4.00 g of silica particles (Schott, OX50, 40 nm) were first taken in a glass tube and heated at 165° C. under vacuum using a Buchi heater/condenser for 3 h. The dried nanoparticles were then transferred to a 250 mL bottom rounded flask containing 200 mL of anhydrous toluene supplemented with 2.00 g of either AFT based silane or control non-AFT silane pre-reacted for 10 minutes with 2.00 g of n-propylamine. The reaction mixture was then refluxed at 120° C. for 24 h. After sinalization of nanoparticle, the liquid suspension was centrifuged and the solid pellets collected thoroughly, and washed with toluene (3×≈25 mL) and methylene chloride (3×≈25 mL) in two separate washing/centrifugation cycles. Finally, the washed filler particles were dried under vacuum overnight at 70° C. The thiol and allyl functionalized fillers were analyzed by DRIFT FT-IR spectroscopy and thermogravimetry (TGA). The 0.5 wt % mass loss difference between silanized and unfunctionalized fillers suggests successful functional group grafting on the surface of glass particles in each case (FIG. 11). Also, the DRIFT FT-IR characterization provides evidence of silanol group disappearance around 3745 $cm^{-1}$, implying successful surface modification (FIG. 12).

Sample Preparation:

Stoichiometric mixtures of a PETMP, TATATO (1:1 molar ratio of thiol:ene), with 1 wt % of I819 as visible light photoinitiator, and 2 wt % of 165 as UV photoinitiator, and 5-50 wt % of SNPs, either the AFT-functionalized to generate the AI or the corresponding negative control to generate the PI were prepared. Silanized fillers and resins were blended in a speedmixer (DAC 150 FVZ, Flakteck) to ensure homogenous formulations. Samples were photocured with 400-500 nm visible light at 50 mW/$cm^2$ for 20 min and then post-cured in an oven at 100° C. for 24 h.

Fourier Transform Infrared Spectroscopy:

An FTIR spectrometer (Nicolet 6700) connected to a tensometer via fiber optic cables was used to monitor the real-time polymerization kinetics in concert with stress measurements. Samples were placed between two cylindrical quartz rods, and 50 mW/cm² light was irradiated from the bottom rod using a light guide connected to a mercury lamp (Acticure 4000, EXFO) with 400-500 nm bandgap filter. The overtone signal of double bonds was monitored at 6160 cm$^{-1}$ during the FT-IR measurements.

Polymerization Shrinkage Stress Measurement:

Shrinkage stress was measured via a tensometer using cantilever beam deflection theory (American Dental Association Health Foundation, ADAHF-PRC). A composite paste (1 mm in thickness, 6 mm in diameter) is placed between two cylindrical quartz rods, which were previously treated with a thiol silane. A 50 mW/cm² of light was irradiated for 2 min from the bottom rod using a light guide connected to a mercury lamp (Acticure 4000, EXFO) with a 400-500 nm bandgap filter. Polymerization-induced shrinkage of sample exerted a tensile force which caused the deflection of the aluminum beam. A LVDT (linear variable differential transformer) was used to convert the displacement to shrinkage stress based upon beam calibration constant and cross-sectional area of the sample. For the simultaneous measurement of conversion with shrinkage stress, data was collected continuously for 15 min.

Viscosity Measurement:

The resin viscosity was measured via a TA instruments ARES rheometer. Each resin was placed between two parallel quartz plates (8 mm in diameter, 0.4 mm in thickness), and the viscosity was monitored at a shear rate of 252 s$^{-1}$.

Scanning Electron Microscopy:

Scanning electron microscope (Zeiss, Supra 60) was used to investigate the microstructures and the fracture surfaces of composites. Samples were coated with a thin layer of gold to prevent charging before the observation by SEM.

Thermogravimetric Analysis:

Thermogravimetric analysis (TGA Pyris 1, PerkinElmer) was used to analyze the functionalized silica nanoparticles. Each sample was run in a nitrogen atmosphere (20 ml min$^{-1}$) from 50° C. to 850° C. at a heating rate of 10° C. min$^{-1}$.

Three-Point Bend Test:

Rectangular bars (2×4×20 mm) and a 3-mm long notch on one edge were used for three-point bend tests to measure fracture toughness. The three-point bend test was performed using a (MTS 858 Mini Bionix II) testing machines. Five specimens of each composition were tested to evaluate the mechanical tests with displacement rate of 1.0 mm/min. The fracture toughness was calculated using the following equation:

$$K1c = \frac{PmS}{WD^{\wedge}\left(\frac{2}{3}\right)} f\left(\frac{a}{w}\right)$$

where a is the crack length and f (a/w) is the polynomial geometrical correction factor given as:

$$f\left(\frac{a}{w}\right) = \frac{3\left(\frac{a}{w}\right)^{1/2}\left[1.99 - \left(\frac{a}{w}\right)\left(1 - \frac{a}{w}\right) \times \left(2.15 - \frac{3.93a}{W} + \frac{2.7a^2}{W^2}\right)\right]}{2\left(1 + \frac{2a}{W}\right)\left(1 - \frac{a}{W}\right)^{2/3}}$$

Example 1

Effect of Dynamic Bond Exchange at the Particle Interface on Bulk Shrinkage During Polymerization To form an AI composite and examine the influence of DCC at the particle matrix interface on composite behavior, silica nanoparticles (SNPs) were functionalized with an AFT-capable allyl sulfide containing triethoxysilane (as discussed elsewhere herein), enabling AFT-induced bond exchange upon light exposure in the presence of a suitable radical-generating photoinitiator as illustrated in FIG. 1. For use as a control, SNPs were functionalized with a similar silane also capable of bonding to the resin but not capable of subsequent AFT-mediated bond exchange (PI). In the following experiments, SNPs were dispersed into a resin comprised of a stoichiometric ratio of pentaerythritol tetra(3-mercaptopropionate) PETMP thiol and 1,3,5-triallyl-1,3,5-triazine-2,4,6(1H,3H,5H)-trione (TATATO) alkene that leads to the formation of a glassy polymer network as the resin phase of the composite. Loading of SNPs is varied to include 5 wt %, 15 wt %, 25 wt %, and 50 wt % of the total composite weight, recognizing that the importance and volume fraction of the interface rises along with the increase in filler loading.

Figure 2B:
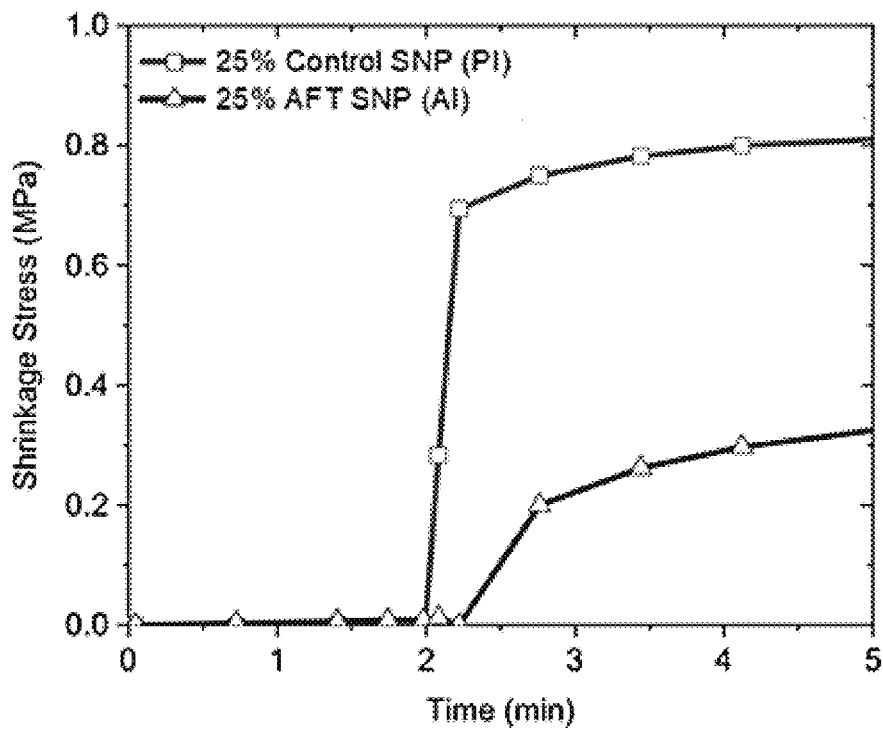
Figure 2C:
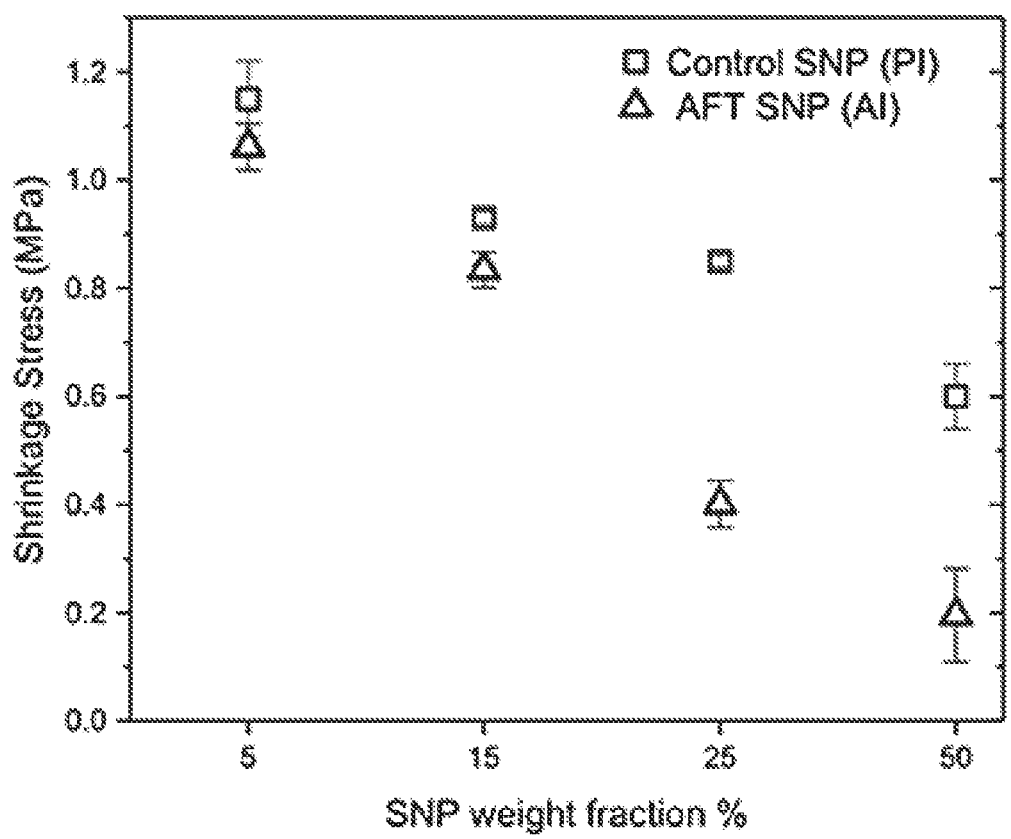

Internal stresses are well known to arise in composites, both within the bulk resin as well as at the particle interface during curing, leading to diminished composite performance and premature failure through initiation of microcracks and interfacial debonding. To investigate the effect of dynamic bond exchange at the particle interface on bulk shrinkage stress reduction, a tensometer connected to an FTIR spectrometer via fiber optic cables was used to monitor real-time functional group conversion and the corresponding stress generated due to polymerization shrinkage (FIG. 2). In the radical mediated thiol-ene polymerization, the AFT process occurred simultaneously with photopolymerization of the thiol-ene monomers to facilitate stress relaxation at the particle interface via bond reconfiguration. Due to the interfacial bond exchange, the AI system containing 25 wt % SNPs showed modestly slower photopolymerization reaction kinetics (FIG. 2A) because the allyl sulfide functionality and the vinyl ether compete in reactions for the thiyl radical. The residual stress was measured to be 0.9 MPa in the PI sample and 0.5 MPa in the AI system, indicating a significant 45% reduction in shrinkage stress after curing to equivalent conversions when AFT was present only at the particle interface (FIG. 2B). Varying the loading of SNPs to 5 wt %, 15 wt %, 25 wt %, and 50 wt % resulted in shrinkage stress decreasing monotonically with increased SNP loading for both AI and PI systems, as shown in FIG. 2C. The reduction in shrinkage stress with increasing particle loading is due to the reduction in overall reactive functional group density, which is responsible for the bulk volumetric shrinkage during polymerization. Both AI and PI systems exhibit fairly similar shrinkage stress at low loading where the contribution from the interface is the least; however, the disparity in shrinkage stress between the two systems becomes progressively more significant at higher loading, such as 25 wt % and 50 wt %, with dramatic reduction of shrinkage stress observed for the AI-based composite when compared to the PI composites. Both composite systems exhibit the same tensile modulus for any given SNP loading level (FIG. 8), which indicates effective covalent attachment between the resin and filler with either interfacial configuration.

Example 2

Dynamic Bond Exchange to Relieve Stress After Polymerization During Mechanical Loading of Composites Interfacial bond exchange is not limited to influencing the shrinkage stress development during curing, and it can be further employed to relieve stress after polymerization during mechanical loading of composites. Accordingly, post-polymerization stress relaxation experiments were conducted on the composites to assess the influence of AI in fully cured, glassy composites. A constant strain of 1% was applied to all composites, which were then exposed to 365 nm light at a 20 mW/cm$^2$ intensity for 10 min. The light source served to activate the bond exchange process at the particle interface in the presence of I651 as a latent UV-initiator.

Figure 3B:
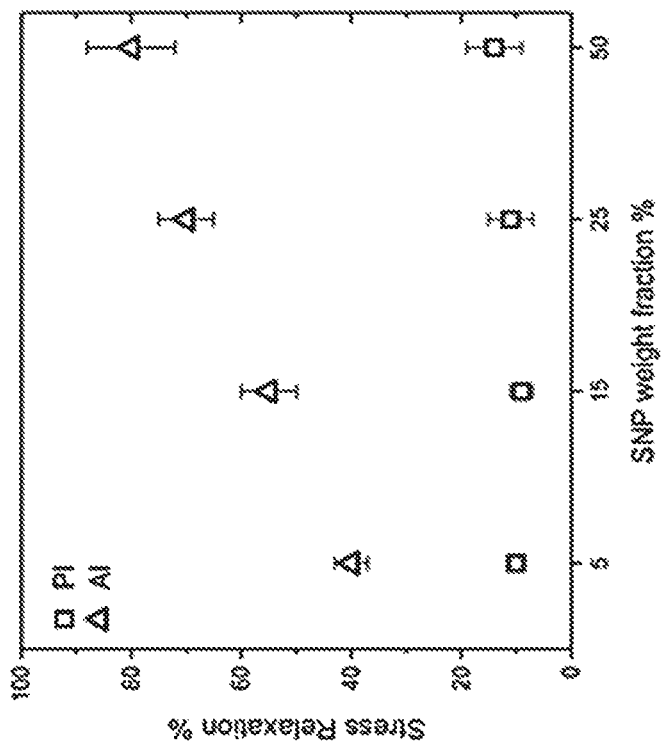
FIGS. 3A-3B are graphs showing stress relaxation. Photoinduced stress relaxation achieved on fully cured 0.25 mm thick sample, of a 1:1 PETMP/TATATO with 25 wt % of both control SNPs to generate PI (squares) and AFT SNPs to generate AI (triangles), at constant 1% strain (FIG. 3A). Final stress relaxation as a function of SNPs weight fraction is also shown (FIG. 3B). The specimens were irradiated at t=0 with 365 nm, 20 mW/cm$^2$ UV-light for 10 min.
Figure 3A:
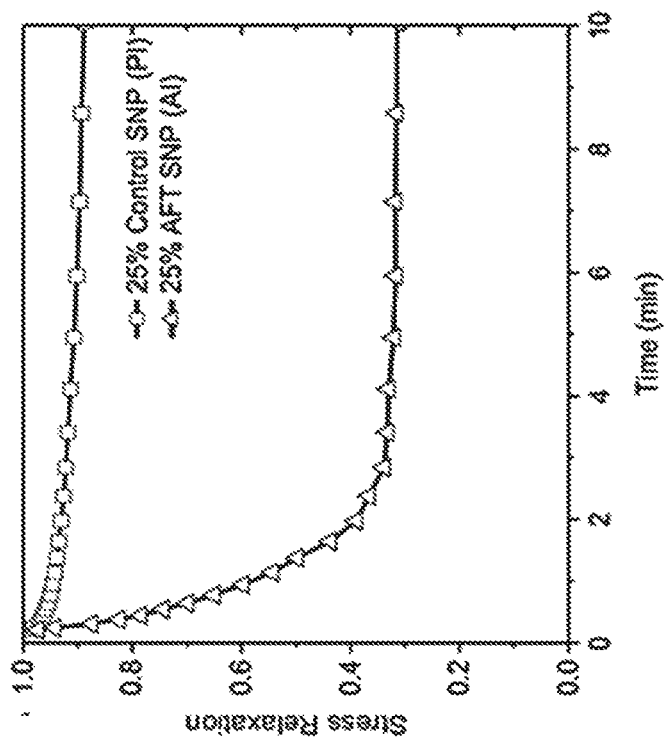

FIG. 3A shows that for a fixed SNP loading of 25 wt %, the AI composites relaxed 70% of the initial stress, while the PI composites relaxed only 11% of the initial stress. The relaxation exhibited by the PI composite is attributed to segmental motion along chains in the glassy state while the large degree of additional stress relaxation in the AI system is considered to be a result of interfacial bond exchange. At 50 wt % fillers, this represents a 66% increase in the stress relaxation of AI composites relative to the PI composites. Varying the SNP loading in the system results in minimal change in the stress relaxation behavior of the PI samples, but dramatically affects the AI behavior (FIG. 3B). Specifically, the AI composites relaxed 40% of the initial stress at 5 wt % SNP loading, 55% at 15 wt % SNP loading, 70% at 25 wt % and 80% of the initial stress at 50 wt % SNP loading. These observed trends of more stress relief at higher SNP loading in the AI composite are due to the increase of the interfacial surface area associated with increasing the SNP loading, which then increase the number of exchangeable bonds at the interface relative to the overall composite volume.

Example 3

Three-Point Bending Test

Figure 4A:
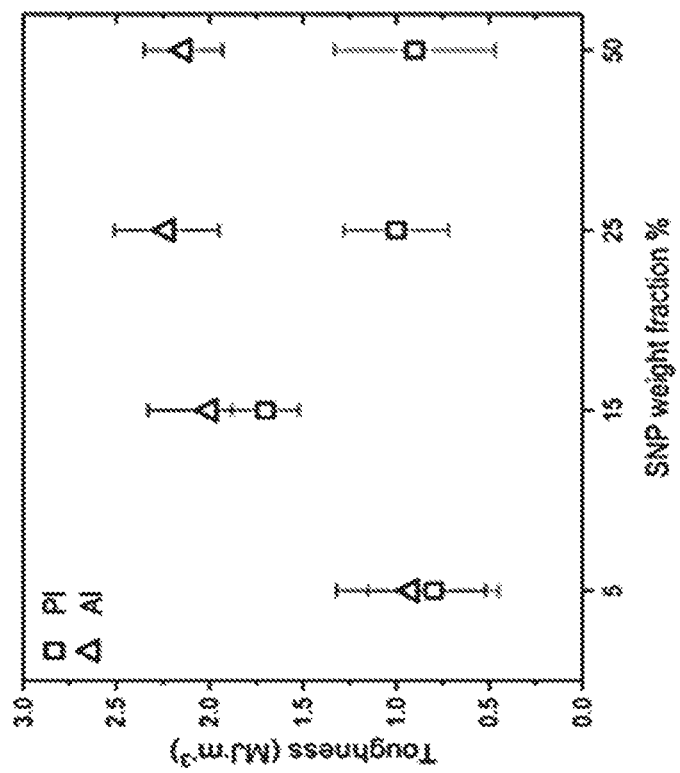
FIGS. 4A-4C are graphs illustrating the effect of nanoparticle weight fraction % on the mechanical properties of PI-based SNPs (squares) and AI-based SNPs (triangles). Tensile yield strength versus wt % SNP (MPa) (FIG. 4A), Toughness (MJ·m$^{-3}$) versus wt % SNP (FIG. 4B), Toughness (MJ·m$^{-3}$) versus tensile yield strength (MPa) (FIG. 4C) at 5, 15, 25 and 50 wt % SNP. Stoichiometric mixtures of PETMP and TATATO (1:1 SH:ene), with 1 mol % of I819 visible light photoinitiator per functionality, 2 mol % of I651, and 5-50 weight percentages of SNPs functionalized with either the AFT silane to generate the AI composite or the control silane to generate the PI composite were prepared then cured with 400-500 nm visible light at 50 mW/cm$^2$ for 20 min, then post-cured in an oven at 100° C. for 24 h.
Figure 4B:
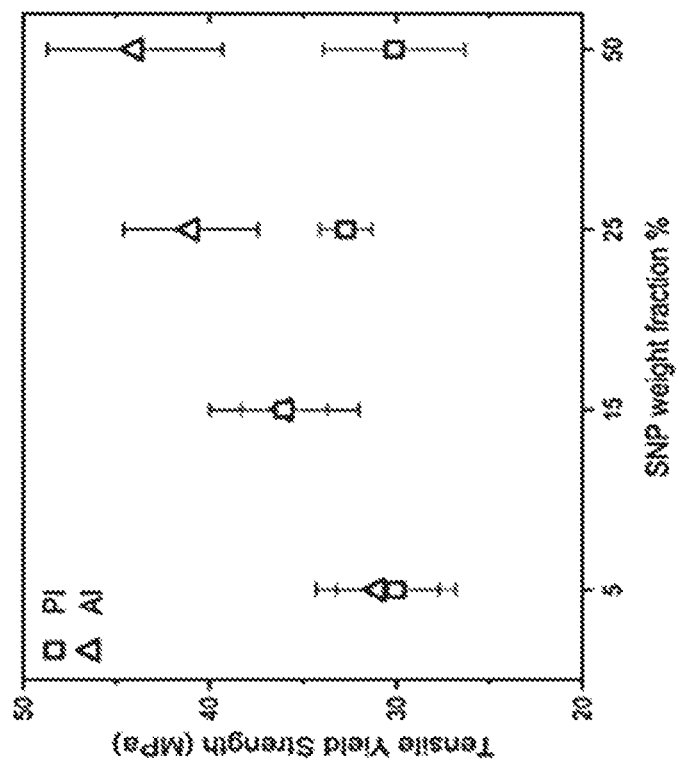
Figure 8:
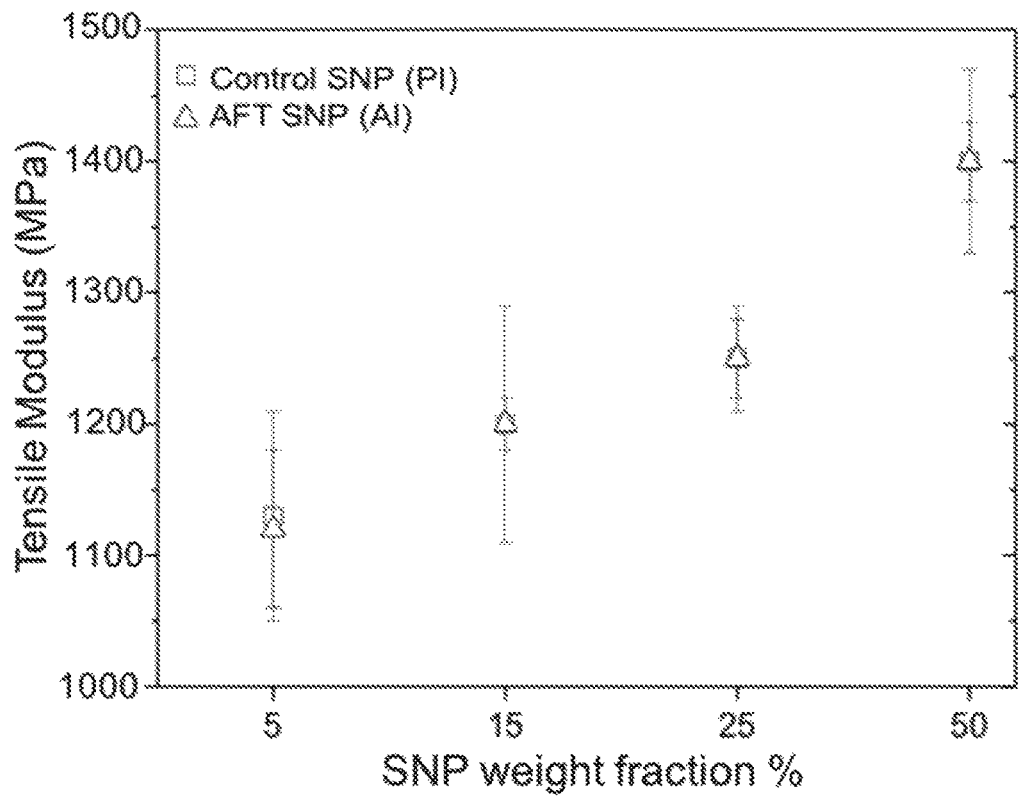
FIG. 8 shows tensile young's modulus for both PI (square) and AI (triangle) composites as a function of SNPs weight fraction. Resins were formulated with a stoichiometric ratio of PETMP and TATTATO (1:1 thiol:ene). Polymerization was conducted with 1 wt % of I819 as visible light photoinitiator, and 2 wt % of I65 as UV photoinitiator. Samples were photocured with 400-500 nm light at 50 mW/cm$^2$ for 20 min and then post-cured in an oven at 100° C. for 24 h.

In addition to static testing at a constant strain, samples with varied SNP loading were subjected to a 3-point bending test with a strain ramp of 1 mm/min until failure. Samples were not illuminated during the strain ramp, so bond exchange in the AI composites was confined to the curing stage. Young's modulus increased linearly with increasing nanoparticle weight fractions for PI and AI system (FIG. 8). The tensile strength (FIG. 4A) and toughness (FIG. 4B) of the PI composite improved with greater SNP loading values up to an optimum value of 15 wt % and then began deteriorating with larger SNP content. This optimal loading value is consistent with the existing literature where the phenomenon has been attributed to the formation of physical defects within nanocomposites during the curing process at higher loadings where particle-particle interaction due to aggregation begins to occur, creating physical defects that act as stress concentrators, weakening the composites. It is therefore interesting to note that the AI-based nanocomposites diverged from this typical behavior. Specifically, tensile strength increased linearly with increasing weight fractions of SNPs, well beyond the optimal 15 wt % seen in the control, FIG. 4A. Toughness measured in the AI composites increased significantly moving from 5 wt % to 15 wt % filler. Increasing the filler amount beyond 15% did not compromise the composite toughness; 25 wt % and 50 wt % composites exhibit a minor increase in toughness relative to the 15 wt % samples, appearing to achieve a plateau as shown in FIG. 4B.

Figure 4C:
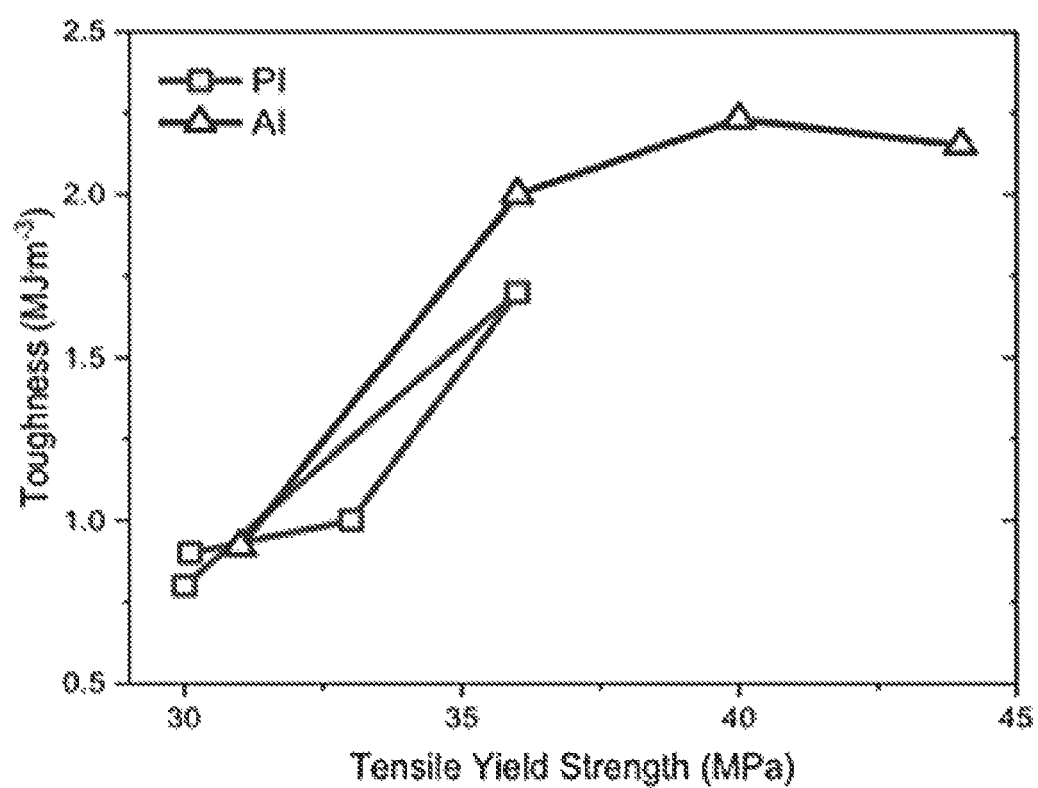

A widespread problem in materials engineering is the general mutual exclusivity of strength and toughness; FIG. 4C highlights the ability of these AI-based composites to defeat this problem and broaden the envelope of attainable properties in this material system. Since a reduction in polymerization shrinkage plays a crucial role in diminishing stress generation and as a result the likelihood of defect formation particularly at interfaces, this behavior is obviously related to the significant reduction in the shrinkage stress with increasing the AI-based SNPs loading (FIG. 2C). At high shrinkage stress, as chains become deformed into less entropically favorable conformations, the energy barrier to chain scission becomes smaller, leading to increased probability of chain scission, which again generates defects. On the other hand, having exchangeable bond at the particle interface in the AI composite works to counter this effect by relaxing chain conformation at the interface, delaying chain scission, and therefore reducing the likelihood of crack nucleation. Additionally, after crack nucleation, the significant reduction in the shrinkage stress caused by the AFT bond exchange causes the SNP interfacial zones ahead of the crack tip to be subjected to lower stresses, when compared to the PI that originally exhibited higher stress during the polymerization process. At high particle loading, this stress is amplified by interactions between the stress fields around the particles, which as a result cause the composite's failure and decreases its ultimate mechanical properties.

Example 4

Effects of In Situ Interfacial Bond Exchange on Composite Failure

Figure 5A:
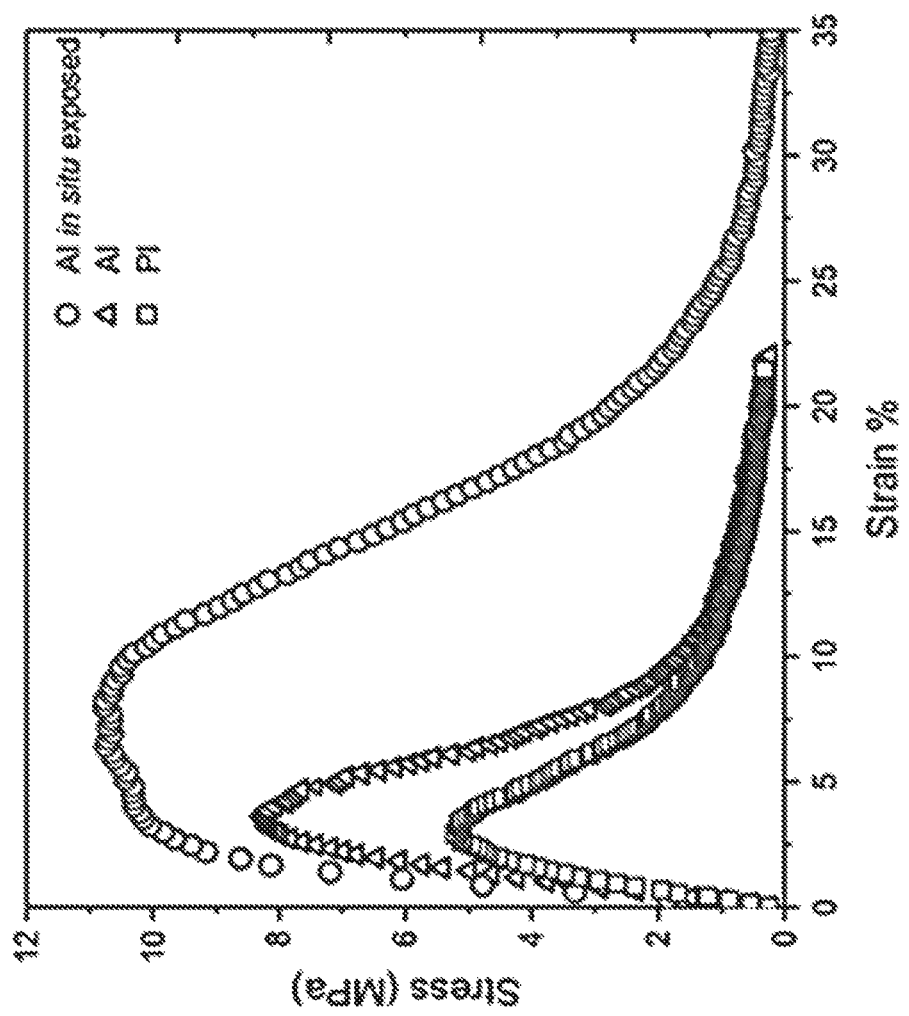
FIGS. 5A-5B illustrate results from the fracture test. Fracture test for fully cured, dogbone-shaped PETMP-TATATO-25 wt % SNPs coated with: □ PI, ▲AI, ○AI radically triggered with 40 mW/cm$^2$ of 365 nm light through the crack tip, during the 3-point bend test at a displacement rate of 1 mm/min (FIG. 5A). High-resolution scanning electron microscopy (FEG-SEM) images (FIG. 5B) were taken for fractured surfaces of three PETMP-TATATO composites containing: AI radically triggered with 20 mW/cm$^2$ of 365 nm light through the crack tip during the fracturing process, AI based SNPs, PI based SNPs.

To investigate the effects of in situ interfacial bond exchange on composite failure, fully cured, pre-cracked samples containing 25 wt % SNPs were subjected to 3-point bend tests. The dimensions of each specimen used in the investigation were 2×4×20 mm with a 3-mm long notch on one edge. The fracture toughness value, $K_{IC}$ (MNm$^{-3/2}$), for each specimen was measured at a crosshead speed of 1 mm/min until fracture. FIG. 5A illustrates the behavior of three different samples subjected to loading: A PI composite, AI composite, and one AI sample exposed to UV-light to enable the AFT in situ at the crack tip during loading. As can be seen from FIG. 5A, the AI composite that was exposed to UV-light to induce in situ interfacial bond exchange exhibited higher yield strength (10.4 MPa) and fracture toughness (2.3 MNm$^{-3/2}$) than both the unexposed AI composite, which exhibited a 8.2 MPa yield strength and 1.3 MNm$^{-3/2}$ fracture toughness, and the PI composite, which gave the lowest values of both yield strength (5 MPa) and toughness (0.8 MNm$^{-3/2}$).

Figure 5B:
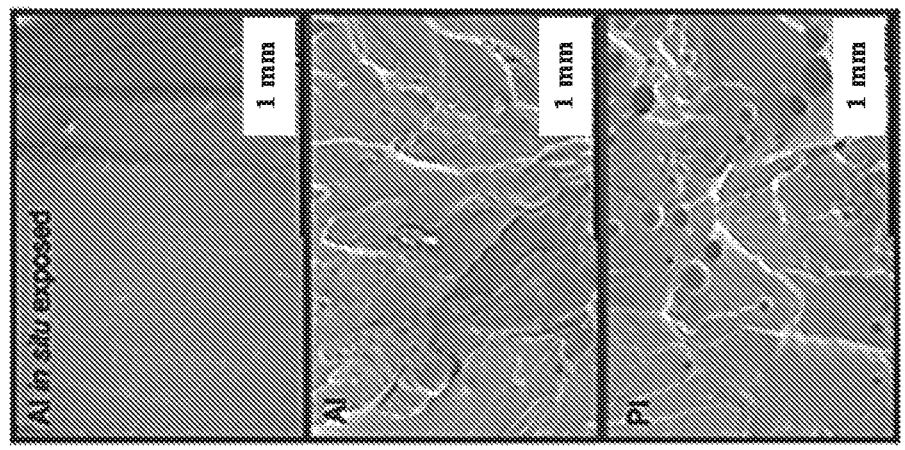
Figure 9A:
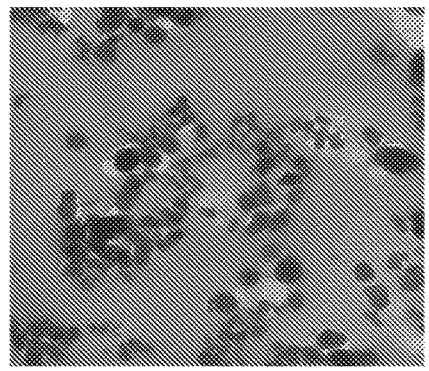
FIGS. 9A-9B show high-resolution scanning electron microscopy (TEM) images taken for surfaces of PETMP-TATATO composites containing: 25 wt % control SNP (PI) (FIG. 9A), 25 wt % AFT SNP (AI) (FIG. 9B). Resins were formulated with a stoichiometric ratio of PETMP and TATTATO (1:1 thiol:ene). Polymerization was conducted with 1 wt % of I819 as visible light photoinitiator, and 2 wt % of I65 as UV photoinitiator. Samples were photocured with 400-500 nm light at 50 mW/cm$^2$ for 20 min and then post-cured in an oven at 100° C. for 24 h.
Figure 9A:
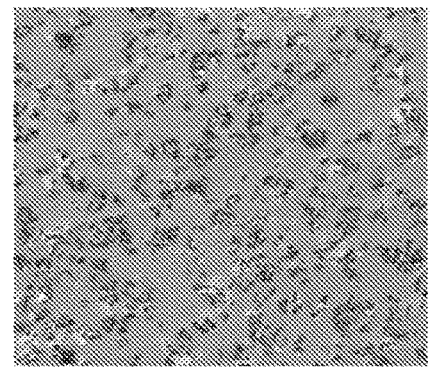
Figure 9B:
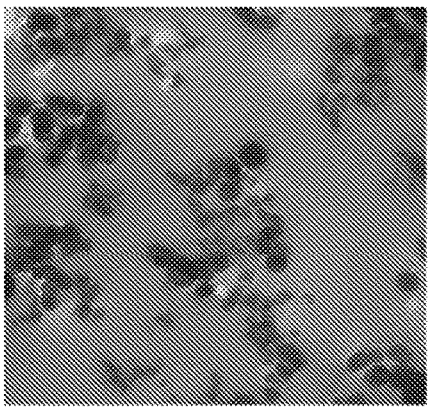
Figure 9B:
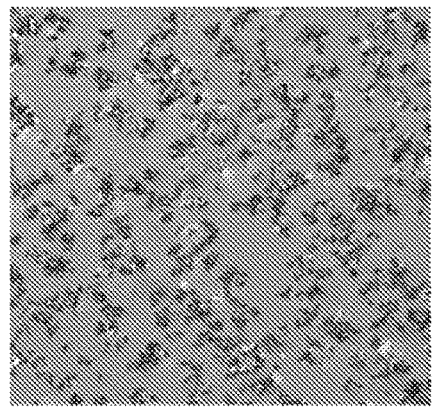

Subsequent scanning electron microscopy (SEM, Zeiss, Supra 60) images were taken of the fractured surfaces (FIG. 5B). Images reveal that both the PI and the unexposed AI composites contain voids dotted throughout the fracture surface. Cavitation of this nature associated with rigid silica particles has been previously reported, where stress concentrations around the SNPs initiate particle debonding, followed by plastic deformation via a void-growth mechanism, which is believed to change the stress state in the surrounding matrix and reduces the constraint at the crack tip. These voids were shown to become less numerous by improving the adhesion between the particles and the resin, where the stress is effectively transferred through the particle-polymer interface and reduces the stress state around the SNPs, which is consistent with the difference in the nature and the number of voids between the PI and the AI composites. These voids are smaller and less numerous on the AI composite, where the particles are subjected to lower stress due to the lower stress that originally built up during the polymerization process when compared to the PI composites. Furthermore, a smoother surface with significantly less exposure of silica nanoparticles along the fracture surface was obtained when in situ AFT bond exchange at the particle-polymer interface was triggered during the fracture process, which relieved the triaxial stress that drives the particles cavitation mechanism, demonstrating a reduction of polymer-particle debonding events during failure. A corresponding increase in the toughness was also obtained when in situ AFT bond exchange at the particle-polymer interface was triggered during the fracture process. Both AI- and PI-based composites showed very similar dispersion of the SNPs using TEM imaging at 25 wt % SNP loading (FIGS. 9A-9B).

Example 5

Influence of Interfacial Bond Exchange in Composites Subjected to Cyclic Loading Typically, cavitation, delamination, and plastic-shear yielding all contribute to dissipation of mechanical energy during loading. It is now demonstrated that while AI suppressed the two former dissipating mechanisms during three-point bending (FIGS. 5A-5B), it accentuated the latter during stress relaxation tests (FIG. 3C). Noting these competing phenomena naturally leads to questions regarding how these composites will behave when subjected to cyclic loading.

Figure 6A:
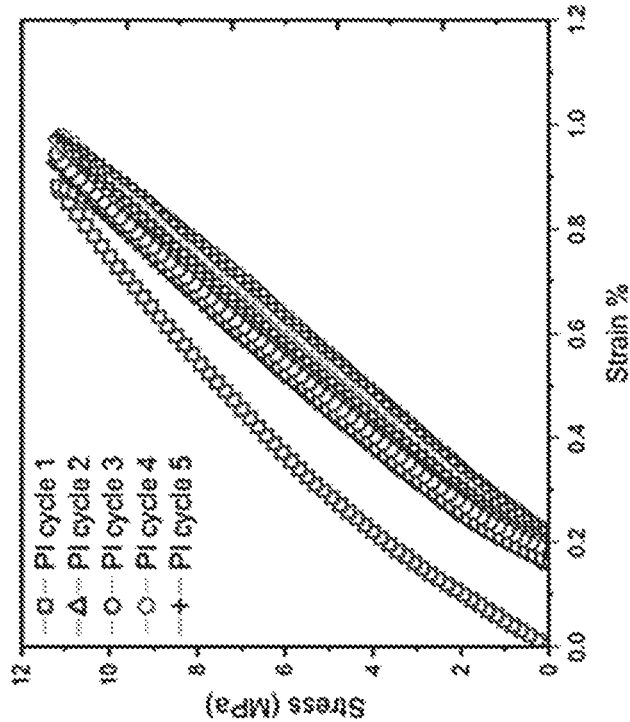
FIGS. 6A-6B are graphs showing five hysteresis loop cycles during loading of 10 N force then unloading to 0 N at 5N/min rate for PETMP-TATTATO-25 wt % of SNPs coated with: AI (FIG. 6A), PI (FIG. 6B). All samples were cured under the same conditions where stoichiometric mixtures of a PETMP, TATATO (1:1 SH:ene), with 1 mole % of I819, 2 mole % of I651, and 25 wt % of SNPs were cured using 400-500 nm visible light at 50 mW/cm$^2$ for 20 minutes, then post-cured in an oven at 100° C. for 24 h.
Figure 6B:
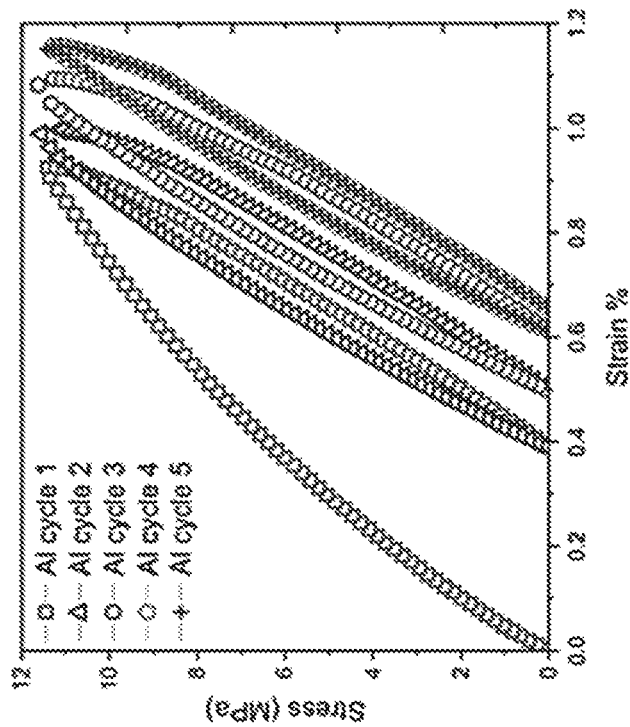

In order to explore the influence of interfacial bond exchange in composites subjected to cyclic loading, a 10 N force was ramped with 5 N/min ramping rate for both PI and AI composites, which were then irradiated with UV-light through the crack tips for 30 s, at which point the force was ramped down over a 2 min period. This procedure was repeated for five loading-unloading cycles, and the hysteresis curves are presented in FIG. 6A for the AI and FIG. 6B for the PI composite. As shown, AI based composites systematically exhibit a greater degree of both energy dissipation and non-recoverable strain throughout all five cycles. Bond exchange in these cycles is limited, however, by the photoinitiator consumption. The rate at which photoinitiator is consumed is altered by adjusting the UV intensity applied to the samples.

Example 6

Figure 10:
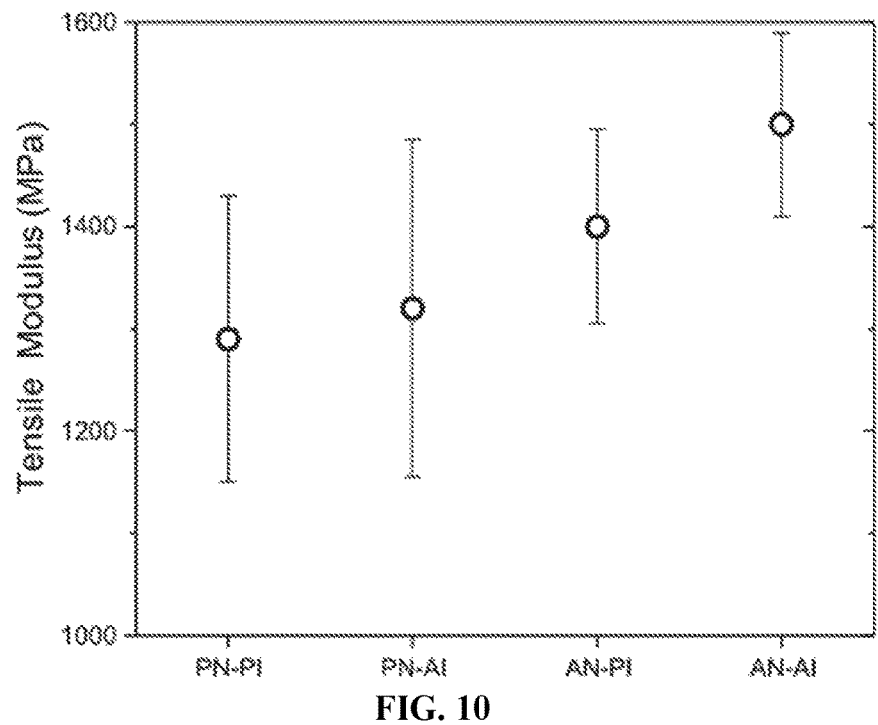
FIG. 10 is a graph illustrating tensile young's modulus of four composite formulations: (i) PN-PI composite with no exchangeable bonds, (ii) PN-AI composite with interfacial bond exchange, (iii) AN-PI composite containing exchangeable bond in the polymer network but not at the interface, and (iv) AN-AI composite containing exchangeable bonds both in the polymer backbone and at the resin-filler interface. The resin contained PETMP as the thiol monomer and a stoichiometrically balanced (relative to functional groups) quantity of an allyl and vinyl ether mixture, itself composed of 75 mol % (relative to ene functional groups) TATATO and 25% of either the AFT or non-AFT DVE, with 1 mole % of I819, 2 mol % of I651, and 25 wt % of SNPs were cured using 400-500 nm visible light at 50 mW/cm$^2$ for 20 min. Tensile test was conducted on dogbone-shaped sample with a strain rate of 1 mm/min.

Comparison of the Effects of Interfacial Dynamic Bond Exchange (Adaptive Interface AI) With Bond Exchange Occurring Throughout the Resin Matrix So far, this work has examined composite behavior when AFT is only present and active at the resin-particle interface. Given that AFT has been widely studied in bulk materials, compared here are the effects of interfacial dynamic bond exchange (adaptive interface AI) with bond exchange occurring throughout the resin matrix (adaptive network AN). To do this a modified material formulation of the formulation shown in FIG. 1 was used. Two different resins were employed, an AN resin comprised of 25 mol % of the alkene forming the composite was supplied by the 2-methylene-propane-1,3-di (thioethyl vinyl ether) AFT-DVE monomer to facilitate bond exchange throughout the polymer network, and the non-AN resin using the control, nonfunctional analog alkene. The AFT monomer and the negative control analog monomer structures used to produce the materials for this study are shown in Scheme 1. Also, employed are two different silanes for functionalizing particles, either an AFT-silane to generate the AI or non-AFT silane to generate the PI. Four different permutations were then examined: 1. A control composite which does not contain any AFT-exchangeable bonds in the polymer backbone nor at the SNPs surface (PN-PI), 2. AI-based composite containing AFT-moieties only at the SNPs surface coming from AFT-based silane (PN-AI), 3. AN-based composite containing AFT moieties only in the polymer backbone coming from AFT-DVE monomer (AN-PI), 4. Composite based on both AI and AN by introducing AFT moieties in both the polymer backbone and at the surface of SNPs (AN-AI). The four formulations produce equivalently crosslinked networks with similar $T_g$'s of 30° C., and tensile moduli of 1300-1500 MPa at room temperature (FIG. 10 & Table 1).

Scheme 1.

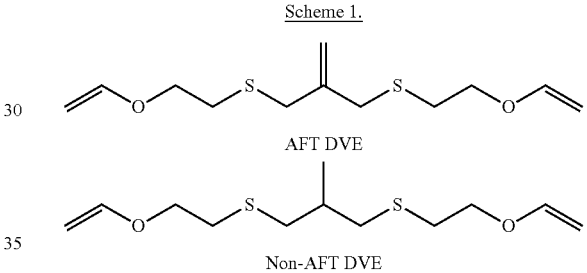

2-Methylene-propane-1,3-di (thioethyl vinyl ether) (AFT-DVE) monomer and the negative control analogue 2-methylpropane-1,3-di (thioethyl binyl ether) (non-AFT).

TABLE 1

Viscosity measurement at a shear rate of 250 s⁻¹, glass transition temperature (° C.) and storage modulus (MPa) at $T_g$ + 30° C. of four different composite formulations.

| Sample | Viscosity (Pa · s) | $T_g$ (° C.) | Storage modulus (MPa) |
|---|---|---|---|
| PN-PI | 1 | 28 ± 2 | 17 ± 3 |
| PN-AI | 1 | 27 ± 2 | 20 ± 2 |
| AN-PI | 1 | 25 ± 2 | 20 ± 5 |
| AN-AI | 1 | 27 ± 2 | 21 ± 3 |

Figure 7A:
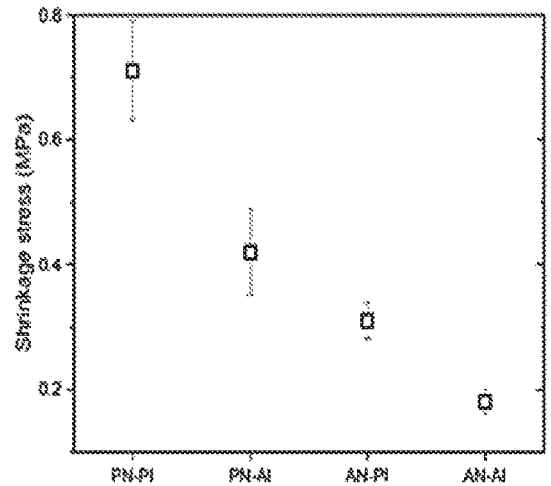
FIGS. 7A-7B are graphs showing final polymerization shrinkage stress and material properties of the composites. Final polymerization shrinkage stress taken after 10 min reaction time as a function of the double bond conversion via tensometer (FIG. 7A). Material properties (FIG. 7B): Toughness (MJ·m$^{-3}$) (circles) and Tensile yield strength (MPa) (squares) of four composites: (i) PN-PI composite with no exchangeable bonds, (ii) PN-AI composite with interfacial bond exchange, (iii) AN-PI composite containing exchangeable bond in the polymer network but not at the interface, and (iv) AN-AI composite containing exchangeable bonds both in the polymer backbone and at the resin-filler interface. The resin contained PETMP as the thiol monomer and a stoichiometrically balanced (relative to functional groups) quantity of an allyl and vinyl ether mixture, itself composed of 75 mol % (relative to ene functional groups) TATATO and 25% of either the AFT or non-AFT DVE, with 1 mole % of I819, 2 mol % of I651, and 25 wt % of SNPs were cured using 400-500 nm visible light at 50 mW/cm$^2$ for 20 min. Tensile test was conducted on dogbone-shaped sample with strain rate 1 mm/min.
Figure 7B:
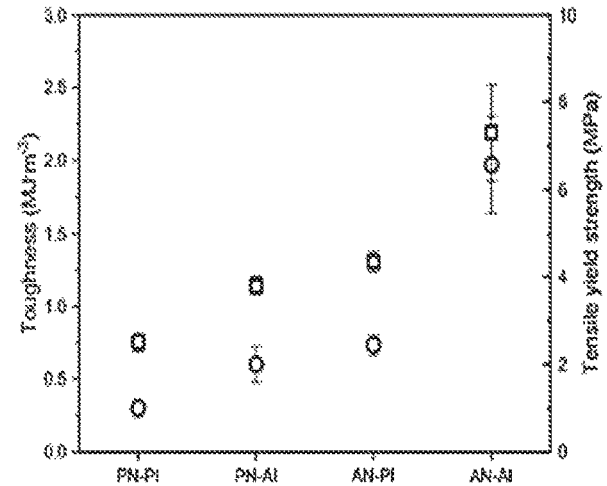

For each of the four formulated composites, real-time polymerization kinetics of the functional group conversion and the corresponding stress generated due to polymerization shrinkage were monitored (FIG. 7A). After curing, tensile tests were performed to compare the effects of interfacial dynamic bond exchange with bond exchange occurring throughout the resin on the mechanical properties of the composites (FIG. 7B). As FIG. 7A shows, the composite that does not contain any exchangeable bonds exhibits the highest degree of shrinkage stress, 0.7 MPa, while the formulation containing exchangeable bonds both throughout the network and at the particle interface (AN-AI) exhibits the lowest degree of shrinkage stress, only 0.2 MPa.

A truly surprising result is observed when comparing samples that limit AFT capabilities to either the resin (AN)

or the interface (AI). FIG. 7B shows that the PN-AI composite where AFT is limited to the interface exhibit similar values of toughness and tensile strength to AN-PI composite where AFT occurs only in the resin despite having an order of magnitude fewer dynamic bonds. This result highlights the importance of interfacial stress relaxation in polymeric composites: Thermosetting resins with standard silica fillers exhibit an enhancement of mechanical properties comparable to those obtained in composites with dynamic, chemically complex resins by functionalizing the filler with CANs-capable silane. Such an approach can be applied to a wide spectrum of resin/filler combinations far beyond the proof of concept examples examined here.

Example 7

The present results demonstrate that interfacial stress relaxation is achieved with significant benefits in performance through selective incorporation of DCC at the resin-filler interface in composites, specifically AFT-based moieties present at the particle surface. During the radical photopolymerization of composites, the process of AFT occurred simultaneously with polymerization leading to a relaxation of the stress at the interface via localized bond reconfiguration. As a result, significant reductions in shrinkage stress were achieved. The influence of interfacial post-polymerization stress relaxation in composites subjected to mechanical loading was also demonstrated. Additionally, a reduction of particle debonding events during the composites failure and a corresponding increase in the toughness were obtained when in situ AFT interfacial bond exchange was triggered during the fracture process. Besides the fact that AFT-exchange is limited by the consumption of photoinitiator, nanocomposites also have limited UV light penetration especially for optically thick specimens or while mechanical loads are being applied. This investigation provides a new platform technology to improve the mechanical performance of thermosetting composites simply by introducing an adaptive yet secure interface to their formulation.

This work can be readily extended to other DCCs and CANs and applied to a wide spectrum of resin/filler combinations beyond what has been exemplified here.

Example 8

Stress Relaxation at the Resin-Particle Interface Via Thiol-Thioester Exchange (TTE)

Figure 13:
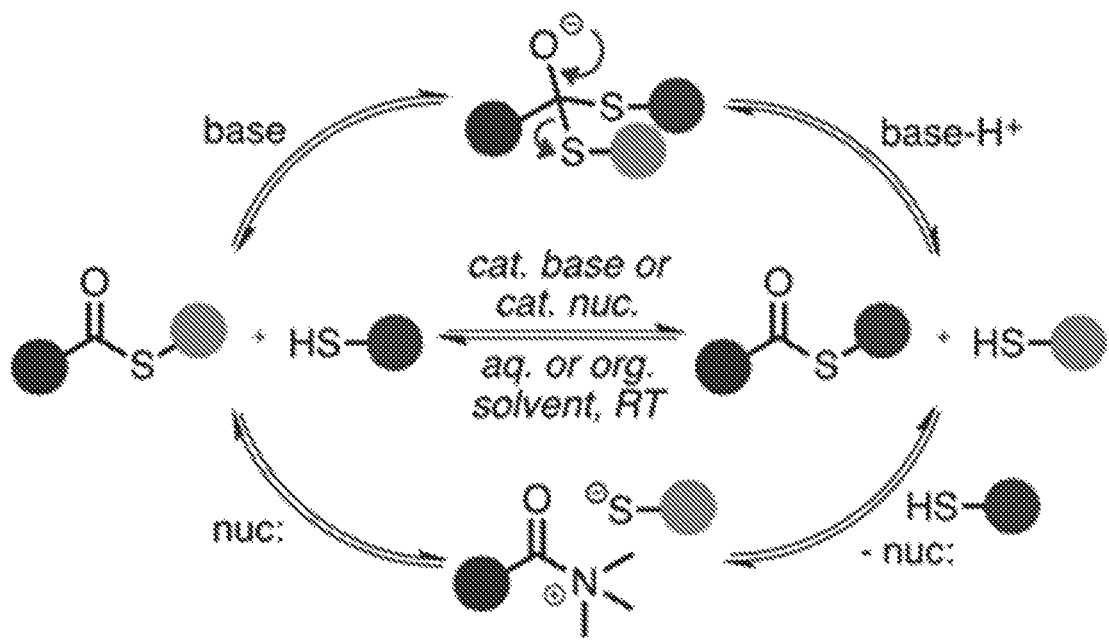
FIG. 13 is a schematic showing mechanism for TTE catalyzed by bases (top) and nucleophiles (bottom).

To highlight the conceptual generality of the adaptive interface, a second DCC interfacial mechanism is also examined here: in the anion-mediated Thiol-Thioester Exchange (TTE) the thioester exchange reaction has been implemented in polymer networks and demonstrated complete, rapid stress relaxation that persists due to the catalytic mechanism. In particular, the TTE exchange reaction, as illustrated in FIG. 13, occurs rapidly in the presence of appropriate bases or nucleophiles leading to a reduction in polymerization stress and rapid, ambient temperature stress relaxation. Once again, while this exchange reaction has been demonstrated in bulk materials, isolation of the phenomenon to relax interfacial stresses has never before been achieved.

Qualitatively, while both AFT and TTE enable stress relaxation when activated, the primary difference is the radical and base/nucleophile catalysts, respectively. The requirement for radicals, with short lifetimes, to mediate AFT necessitates that the process will only primarily occur during light exposure. On the other hand, continuous re-shuffling of covalent bonds in the presence of a base catalyst and excess thiol can be achieved in case of TTE. As such, TTE that remains active throughout the composite lifetime is desired to induce interfacial relaxation in opaque materials without concern for depleting a source of radicals. The result are composites that experience improved fatigue performance and fracture toughness throughout the material's lifetime. Therefore, SNPs were functionalized using a silane that had a TTE moiety capable of bond exchange and dispersed into a thiol-ene resin. Control samples where SNPs were functionalized with a similar silane molecule that is unable to undergo TTE due to elimination of the catalyst was also formulated.

Example 9

Figure 14A:
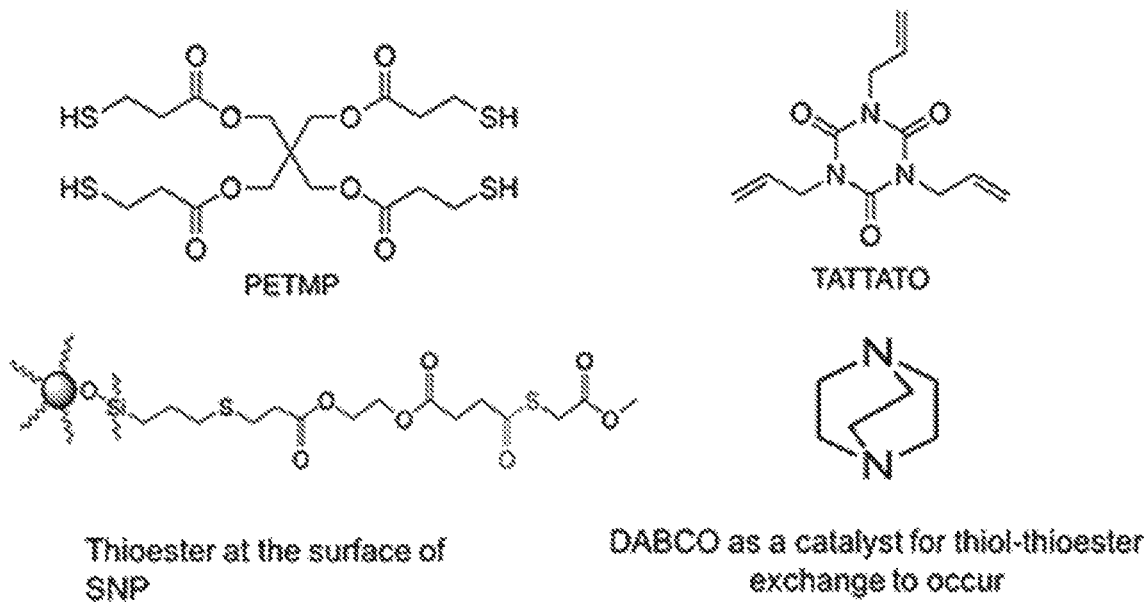
FIGS. 14A-14C show monomers and fillers, polymerization stress, post polymerization stress relaxation. Monomers and fillers used in the formulation of the composites to examine the influence of TTE at the SNP-polymer interface (FIG. 14A). In situ polymerization stress of control composites without catalyst (dotted line), TTE composite with 1 wt. % catalyst loading (dashed line), and TTE composite with 2 wt. % catalyst loading (solid line) (FIG. 14B). Post polymerization stress relaxation achieved on fully cured 0.25 mm thick sample, of a 1.1:1 PETMP/TATATO with 10 wt % TTE-SNP of both control composite without catalyst (dotted line) and TTE composite with 1 wt. % catalyst loading (dashed line), at constant 1% strain (FIG. 14C).
Figure 14B:
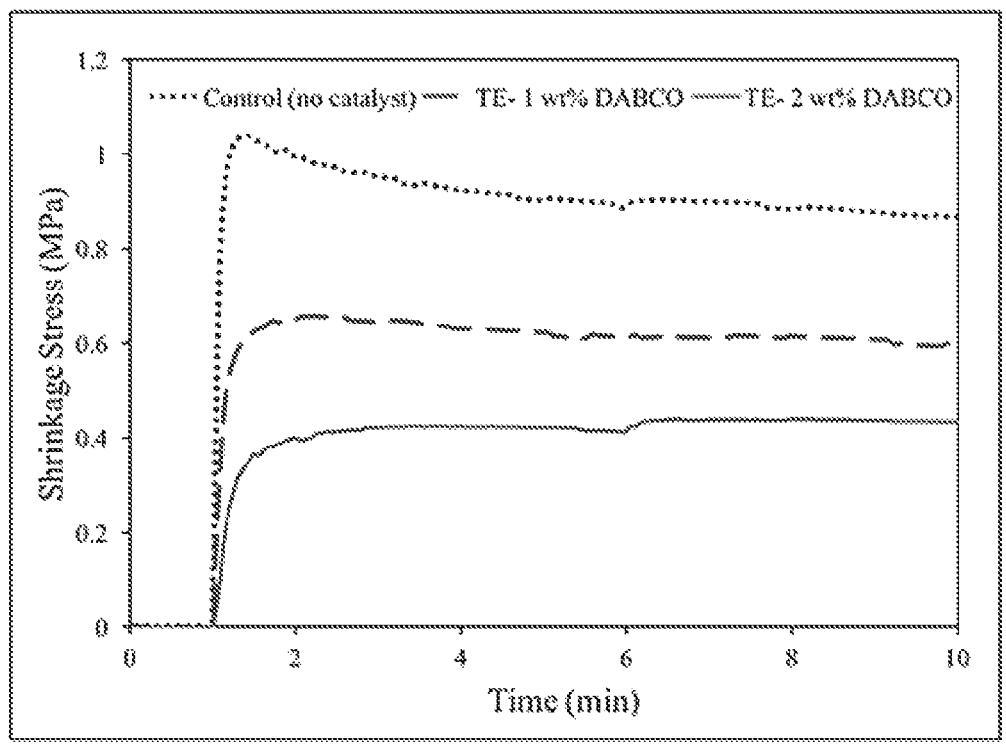
Figure 14C:
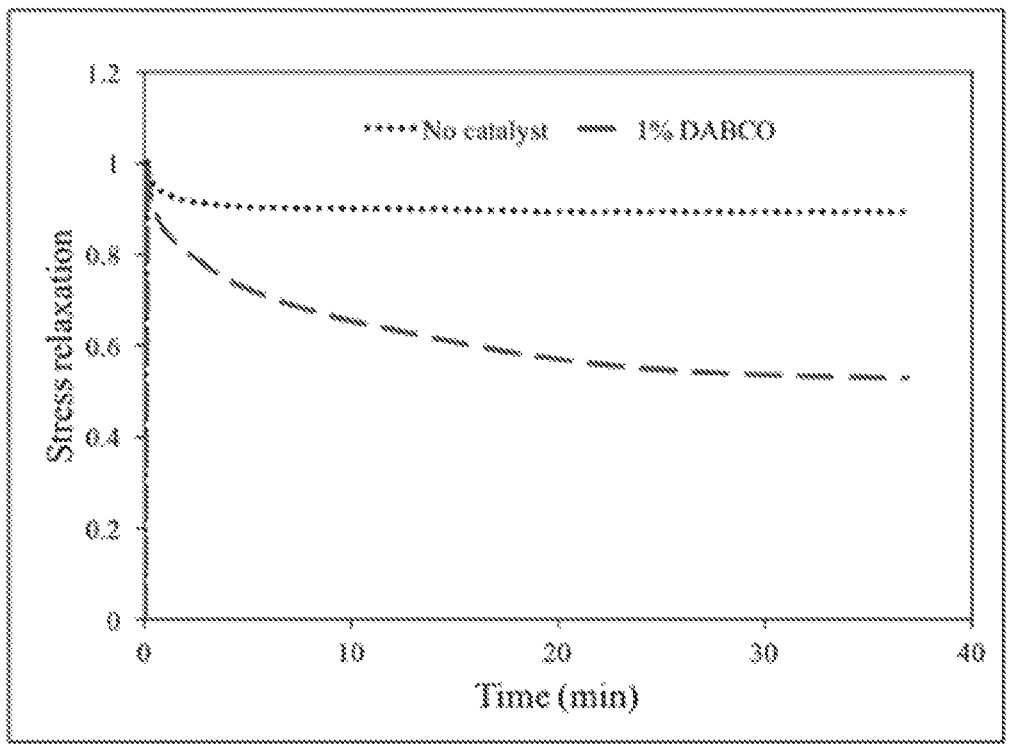

Effect of TTE Interfacial Bond Exchange at the Particle Interface on Shrinkage Stress To investigate the effect of dynamic bond exchange at the particle interface on shrinkage stress reduction within a composite system, an FTIR spectrometer connected to a tensometer via fiber optic cables was used to monitor the real-time polymerization kinetics, and the corresponding stress generated due to the shrinkage. Composites with activated TTE at the particles interface via 1 wt. % of DABCO nucleophile resulted more than 30% lower shrinkage stress as compared with the TTE-free composites used in the control experiment (FIG. 14B). Further reduction in the shrinkage stress (45%) was achieved by doubling the catalyst loading (FIG. 14B). Experiments to measure stress relaxation in fully cured glassy material (Tg as measured in DMA 60-65° C.), show that 50% stress relaxation was achieved after polymerization by activating TTE at filler interface even if the bulk resin is not capable of any DCC (FIGS. 14A-14B).

In certain embodiments, successful interfacial stress relaxation and damage healing via TTE also contribute to improve composite mechanics.

Example 10

Effect of TTE Interfacial Bond Exchange on Composite Failure

To investigate the effects of TTE interfacial bond exchange on composite failure, fully cured, pre-cracked samples containing 10 wt. % SNPs were subjected to 3-point bend tests. The dimensions of each specimen used in the investigation were 2×4×20 mm with a 3-mm long notch on one edge. The fracture toughness value, $K_{IC}$ ($MNm^{-3/2}$), for each specimen was measured at a crosshead speed of 1 mm/min until fracture. Results for the fracture test are compared to a control that is lacking DABCO, the catalyst inducing the TTE exchange.

Figure 15B:
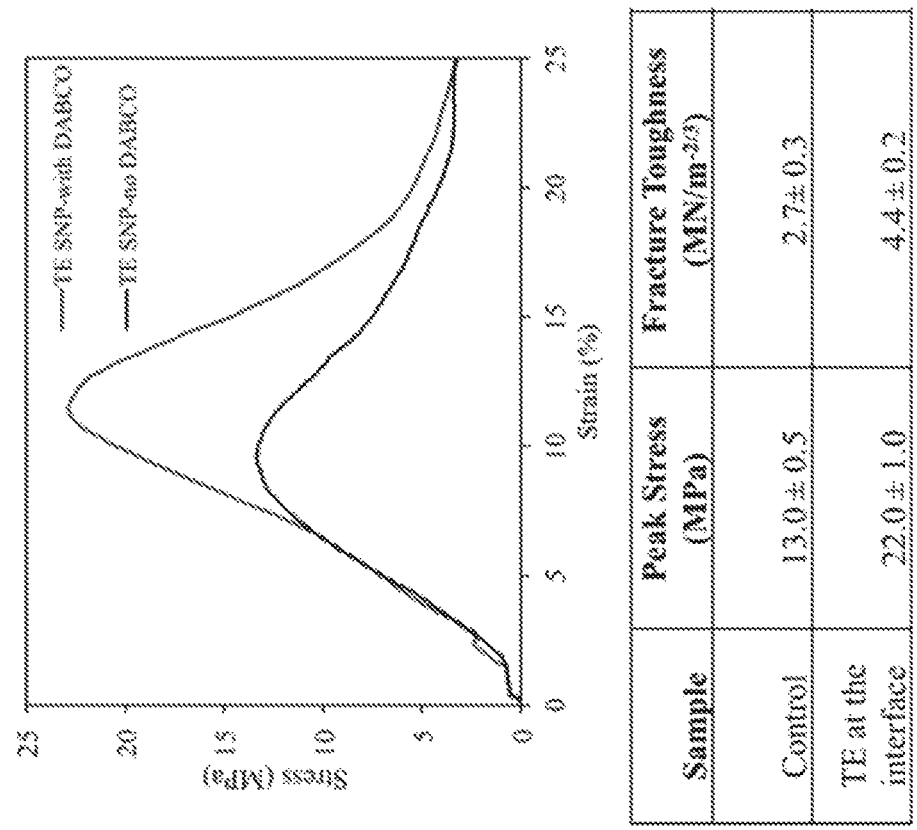
FIG. 15B shows high-resolution scanning electron microscopy (FEG-SEM) images taken for fractured surfaces of TTE based composite and control analogue without the catalyst.
Figure 15A:
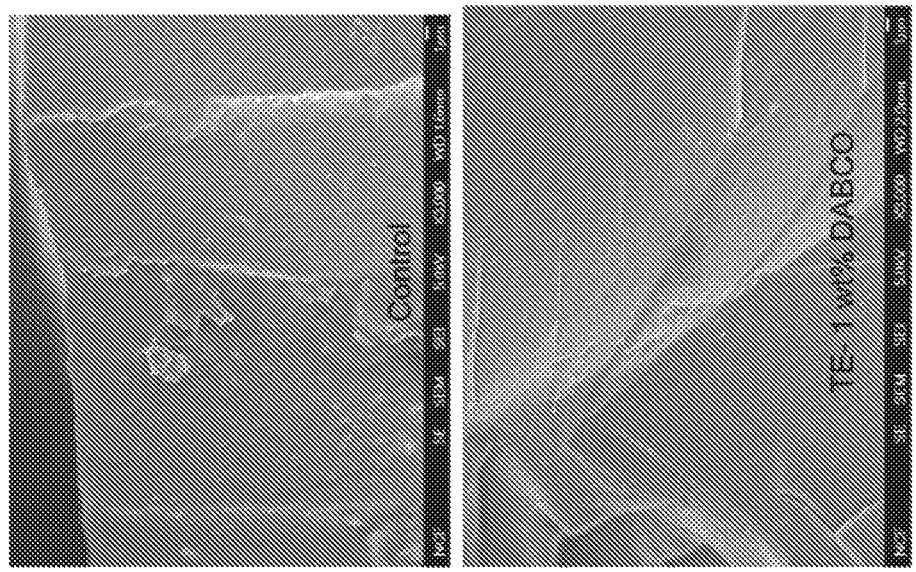
FIG. 15A shows fracture test results for fully cured TTE composite and the control composite.

As seen in FIG. 15B, composite containing DABCO exhibited significantly higher yield strength (22 MPa) and fracture toughness (4.4 $MNm^{-3/2}$) than the control composite, which exhibited a 13 MPa yield strength and 2.7 $MNm^{-3/2}$ fracture toughness, without effecting the modulus of the material. Active-TTE at the interface serves to heal crack tips and enable stress relaxation at the interface, which dramatically affects the fracture toughness of these materials and results in a significant change in stress strain profile.

Subsequent scanning electron microscopy (SEM, Zeiss, Supra 60) images were taken of the fractured surfaces (FIG.

15B). Images reveal that a reduction of particle debonding events during the composites failure, similar to what we have seen in the AFT adaptive interface based composite, was obtained when TTE bond exchange was activated at the particle-resin interface (FIG. 15B).

Example 11

Fracture Testing with 2 Notches

The fracture measurements were performed on a two notch sample with the two notches being of different sizes. The control composite which is identical in chemical structure of the resin and filler fails in a conventional manner through the initially larger crack. In contrast, with the only difference being the addition of the TTE to the interface, the fracture failure behavior is fundamentally different. Here, the large crack initially grows; however, after initial growth of that crack, the interfacial TTE modification leads to crack blunting behavior of the initially larger crack. This effect of the TTE transfers the crack growth and failure to the small notch, requiring more than twice the total energy to fail the material—which now fails at the initially shorter crack—unlike any other conventional material.

Example 12

Figure 21:
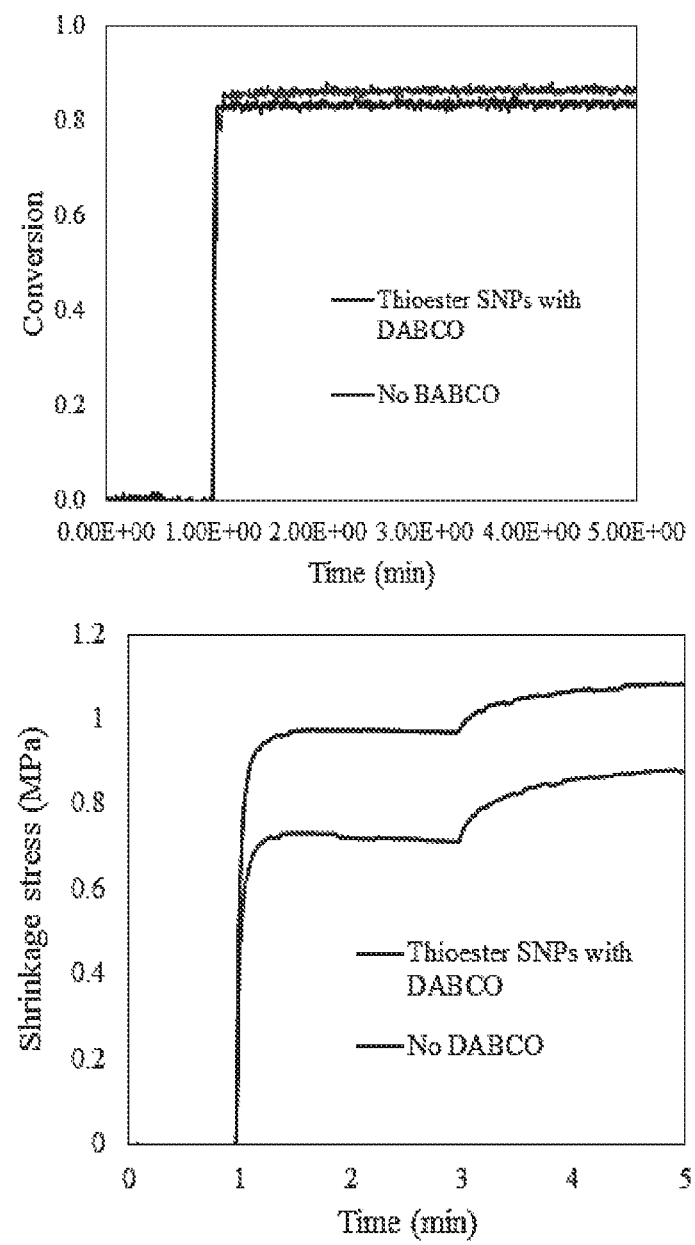
FIG. 21 illustrates shrinkage stress reduction via thioester-based CANs at the particles interface of dental composites. Composition and conditions: BisGMA/TEGDMA (70:30), 1 wt % I819, 1 wt % DABCO(400-500) nm with 400 mW/cm$^2$ intensity.
Figure 21:
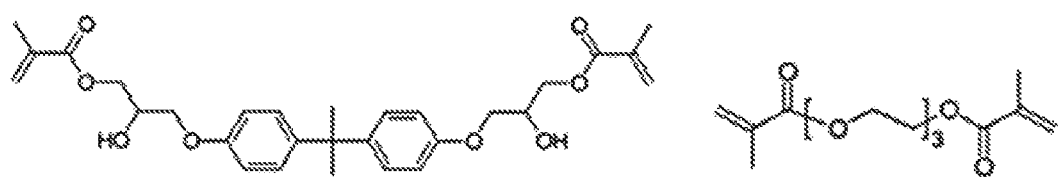

Shrinkage Stress Reduction Via Thioester-Based CANs at the Particles Interface of Dental Composites As shown in FIG. 21 shrinkage stress is reduced in a thioester-based CANs at the particles interface of dental composites.

Example 13

Dental Resin 3-Point Bend Test

Figure 22A:
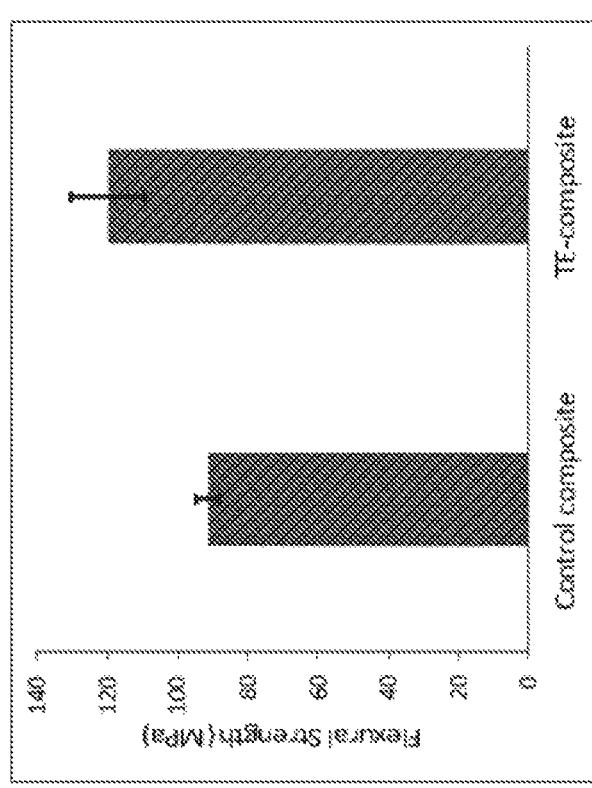
FIGS. 22A-22B illustrates results for BisGMA/TEGDMA (dental resin) 3-point bend test showing elastic modulus (FIG. 22A) and Flexural strength (FIG. 22B) for composites with control filler and composites with thioester filler. Composition: 70/30 BisGMA/TEGDMA, 15 wt % PETMP, 7.5 wt % DABCO, 1 wt % I819, 15 wt % filler (either control or the thioester SNP). Curing conditions: 400-500 nm for 4 min each side; post-cure for 4 hours at 70° C. Tested 16-24 hrs after initial cure. 3-point bend test conditions: strain rate: 0.1 mm/min, sample dimensions: 2 mm thick bars, 20 mm span.
Figure 22B:
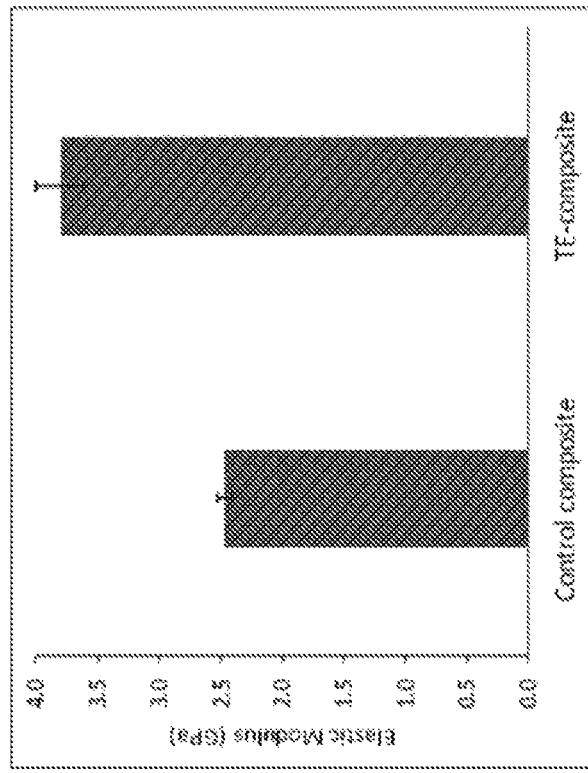

As shown in FIGS. 22A-22B, the TE-composite exhibits higher eleastic modulus and higher flexural strength compared to the control deprived of interfacial TTE. 70/30. The composition is formed from BisGMA/TEGDMA, 15 wt % PETMP, 7.5 wt % DABCO, 1 wt % I819, 15 wt % filler (either control or the thioester SNP). The curing conditions are 400-500 nm for 4 min each side; post-cure for 4 hours at 70° C. Tested 16-24 hrs after initial cure. 3-point bend test conditions was performed at the strain rate of 0.1 mm/min, samples were 2 mm thick bars with 20 mm span.

Example 14

Figure 16:
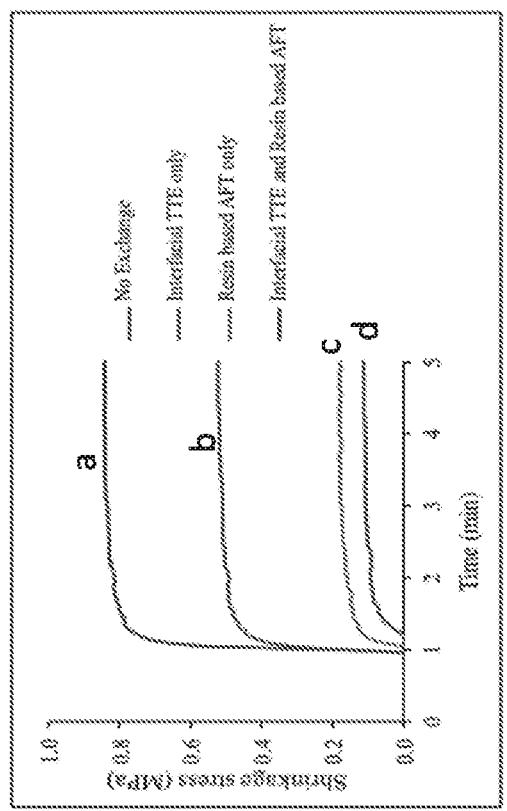
FIG. 16 shows a graph of evolution of shrinkage stress vs. time in thiol-ene composites: No Exchange: non-AFT resin/thioester SNPs, no catalyst (a); Interfacial TTE only: non-AFT resin/thioester SNPs, DABCO added (b); Resin based AFT only: AFT resin/thioester SNPs, no catalyst (c); Interfacial TTE and Resin based AFT: AFT resin/thioester SNP, DABCO added (d). Each composition contained 10 wt. % SNPs, 1 wt. % IR819, and was irradiated with 50 mW/cm$^2$ light intensity of 400-500 nm. Two mixtures contained DABCO (6 mol %).
Figure 16:
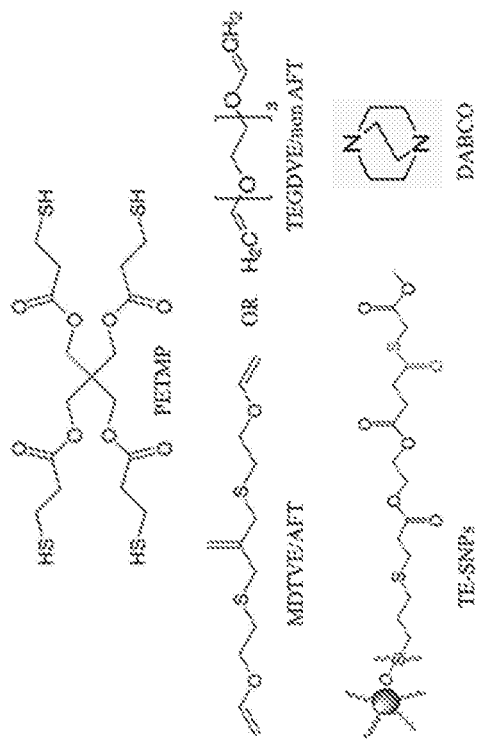
Figure 17:
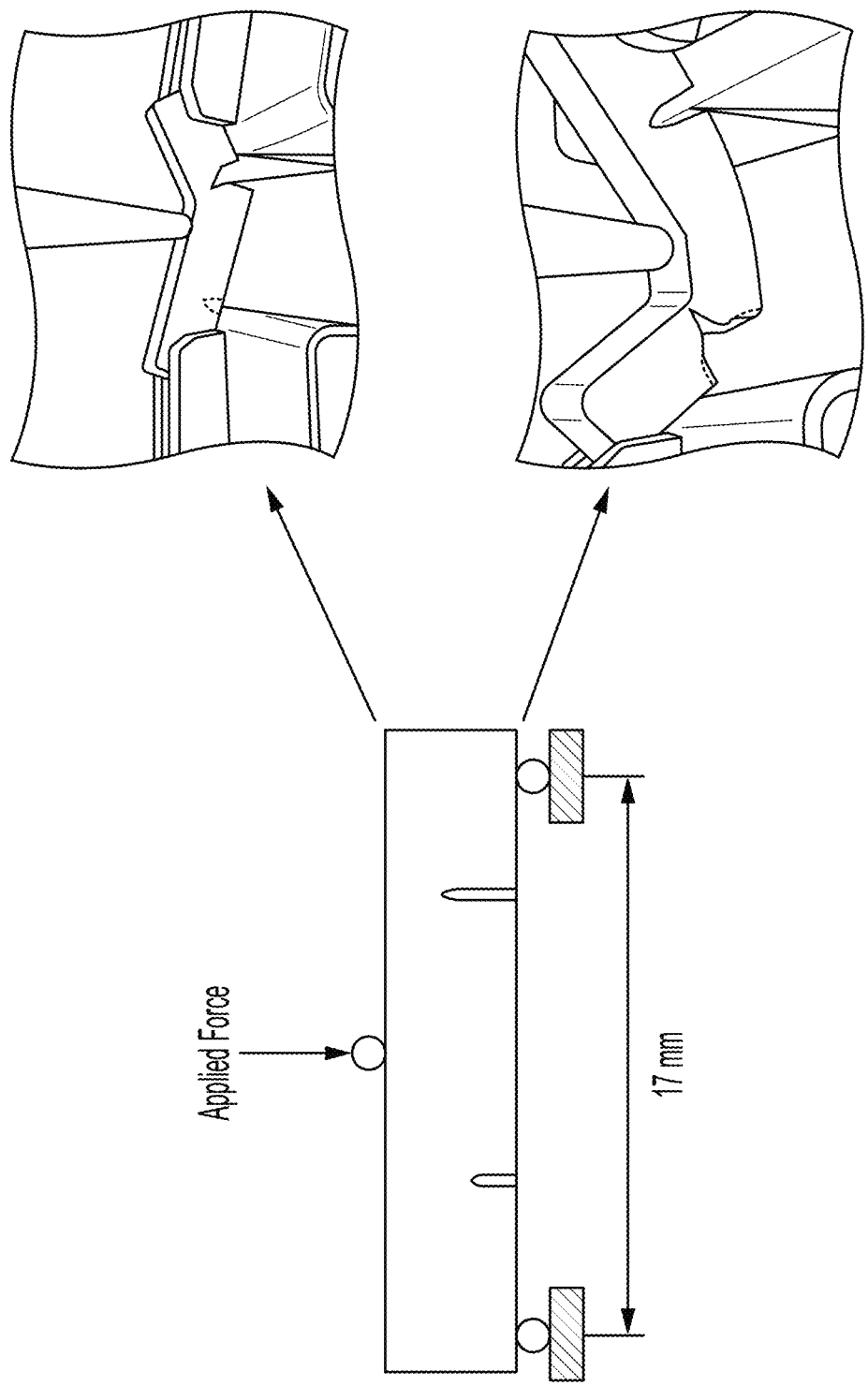
FIG. 17 shows fracture testing with 2-notches for TTE composite, large notch closes, small notch fails.
Figure 18:
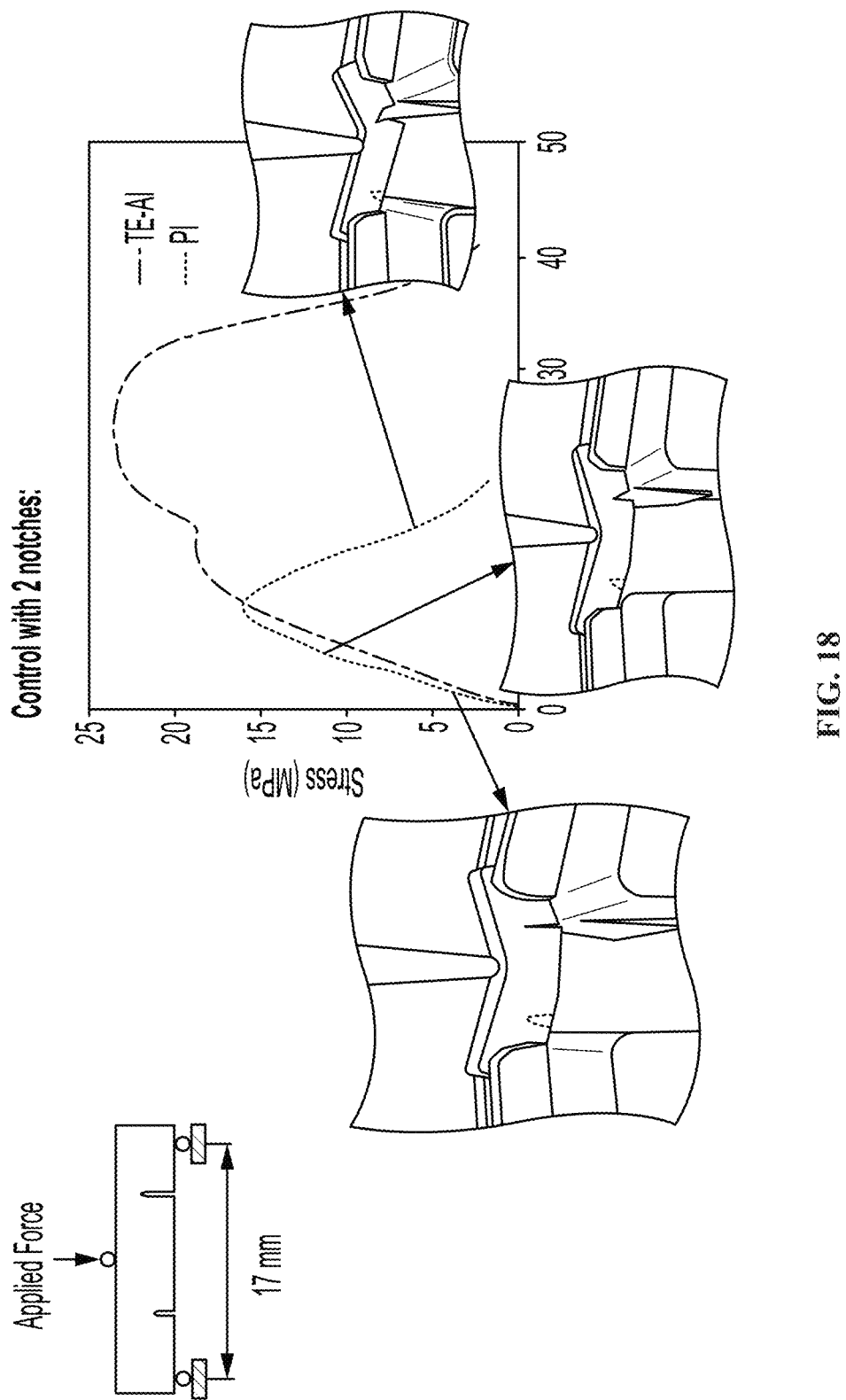
FIG. 18 shows fracture testing with 2-notches for control. The control composite fails in a conventional manner through the initially larger crack. Control had (1.1:1) Thiol:ene, 10 wt % SNPs, 6 mol % DABCO, 1 wt % I819, 1 wt % I651; Curing conditions: (400-500) nm, with 50 mW/cm$^2$ intensity.
Figure 19:
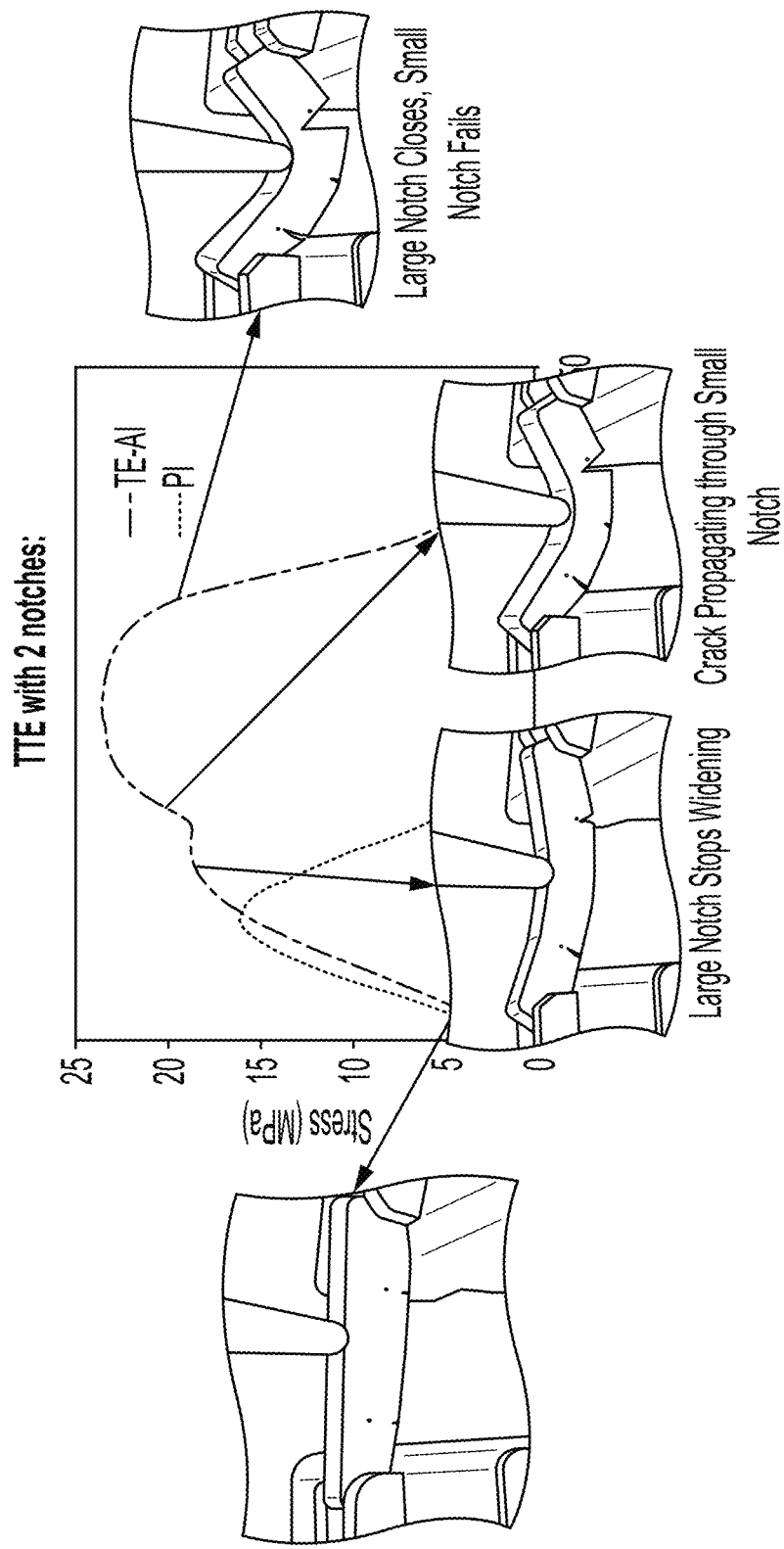
FIG. 19 shows fracture testing with 2-notches for TTE composite. Large notch stops widening, large notch closes and small notch fails. Composite had (1.1:1) Thiol:ene, 10 wt % SNPs, 6 mol % DABCO, 1 wt % I819, 1 wt % I651; Curing conditions: (400-500) nm, with 50 mW/cm$^2$ intensity.
Figure 20:
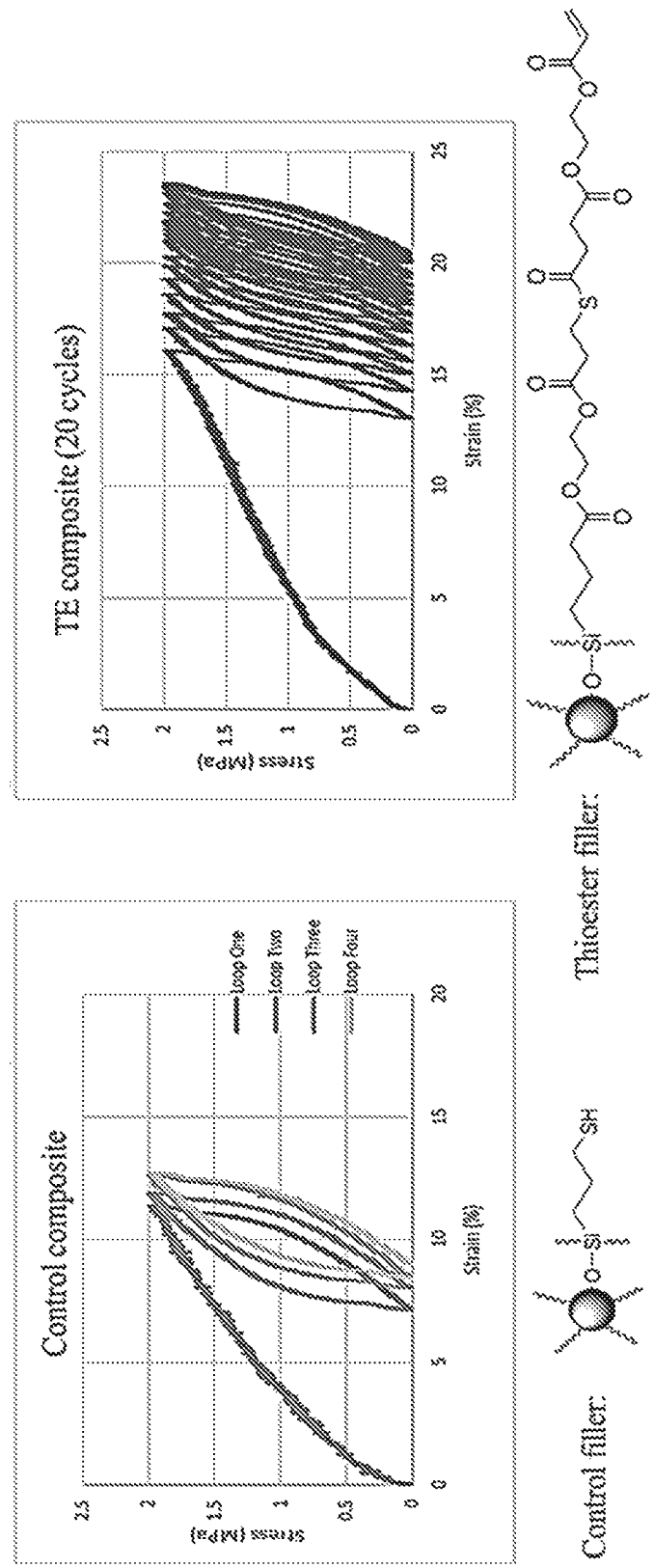
FIG. 20 illustrates certain benefits of the interfacial TTE approach, a cyclic loading (to 2 MPa stress, followed by release and reapplication of the stress) test was performed on a PETMP/TATATO composite, with either thioester-modified fillers or simply thiol-modified fillers. The thioester-modified composite was found to survive more than 20 such cycles while the non-TTE enabled composites were only able to survive 3-4 such cycles. Composition: PETMP:TATATO with 10% excess thiol, 10 wt % particle loading, 1 wt % I819 and 1 wt % DABCO to initiate the bond exchange. Curing conditions: 400-500 nm with 40 mW/cm$^2$ for 4 min each side; post-cure for 4 hours at 70° C.

Combining the Two Types of DCC Approaches—AFT to be Radically Triggered Within the Resin Matrix With TTE to be Triggered Exclusively at the Interface Between the Silica Particle and the Matrix Following successful experiments indicating the potency of the TTE reactions and the exceptional efficiency of interface-limited DCC processes in composites the two types of DCC approaches; AFT to be radically triggered within the resin matrix with TTE to be triggered exclusively at the interface between the silica particle and the matrix were combined. This approach enables the stress relaxation in both locations; within the composite resin matrix and at the resin-filler interface and provide long term stress relaxation throughout the entire life of the composite while only activating the AFT-based exchange when polymerization stresses are generated, or during the light exposure. To determine the AFT effect on shrinkage stress in detail, chemical structures and approaches that provide for an accurate "control" experiment in which no stress relaxation is enabled through elimination of the AFT functional groups or the TTE catalyst were developed. The data is based in part on thiol-ene networks comprised of a divinyl AFT (MDTVE) or non-AFT (TEGDVE) and PETMP (added in 0.1 mol excess), with TE based filler that also are capable of relaxing stress in presence of the catalyst. As can be seen from FIG. 16 over 80% shrinkage stress reduction is observed in a thiol-ene system "equipped" with both types of DCC mechanisms are activated, demonstrating the capability of the AFT/thioester combination to significantly reduce polymerization stress. This combination can lead to dramatically reduce both shrinkage-induced and mechanically applied stress, with noticeable improvement in the mechanical properties and fracture resistant.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising:
a polymer comprising at least one selected from at least one multifunctional thiol monomer, a thiol-ene polymer, and a combination thereof; and
a filler, wherein the filler comprises at least one nanoparticle (NP) functionalized with a chemical moiety capable of engaging in dynamic covalent chemistry (DCC) with the polymer at the polymer-filler interface;
wherein the composition displays stress relaxation at the interface between the polymer and the filler; and
wherein the at least one nanoparticle (NP) is functionalized with a linker comprising at least one of the following groups:
(a) at least one allylic terminal thiol (—SH) group; or
(b) at least one multifunctional thioester of formula (I),

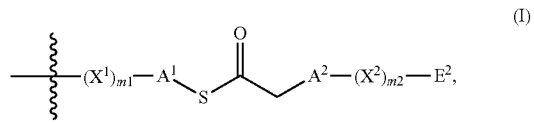

wherein:
$A^1$ and $A^2$ are each independently selected from the group consisting of optionally substituted $C_1$-$C_{15}$ alkylene, optionally substituted $C_2$-$C_{15}$ alkenylene, optionally substituted $C_2$-$C_{15}$ alkynylene, optionally substituted $C_2$-$C_{15}$ heteroalkylene, optionally substituted $C_2$-$C_{15}$ heteroalkenylene and optionally substituted $C_2$-$C_{15}$ heteroalkynylene;

$E^2$ is selected from the group consisting of:

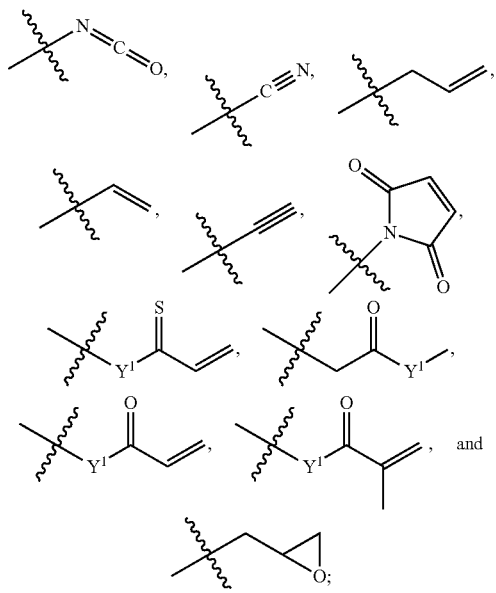

each instance of $Y^1$ is independently selected from the group consisting of O and $N(R^1)$;
each instance of $R^1$ being independently selected from the group consisting of H and $C_1$-$C_6$ alkyl;
m1 is 0 or 1;
m2 is 0 or 1;
$X^1$ is

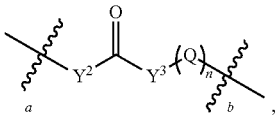

wherein:
bond a is to $A^1$,
Q is $CH_2$ or

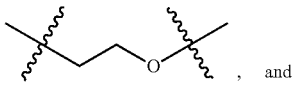 [SMILES: *CCO*]

, and n is 0, 1, 2, 3, 4, 5 or 6;
$X^2$ is

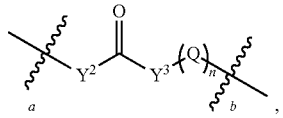

wherein:
bond a is to $A^2$,
bond b is to $E^2$,
Q is $CH_2$ or

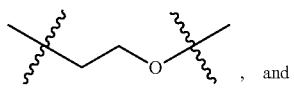 [SMILES: *CCO*]

, and n is 0, 1, 2, 3, 4, 5 or 6;
each instance of $Y^2$ is independently selected from the group consisting of $C(R^1)_2$, O, and $N(R^1)$;
each instance of $Y^3$ is independently selected from the group consisting of $C(R^1)_2$, O, and $N(R^1)$; and
each instance of $R^1$ is independently selected from the group consisting of H and $C_1$-$C_6$ alkyl.

2. The composition of claim 1, wherein the at least one multifunctional thiol monomer is selected from the group consisting of:

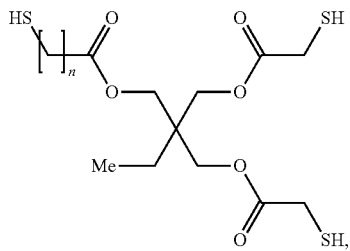

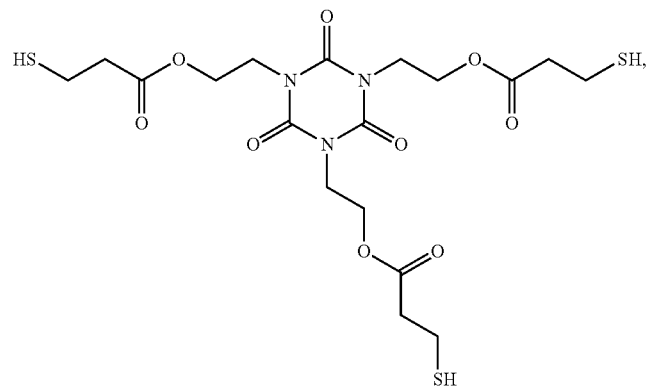

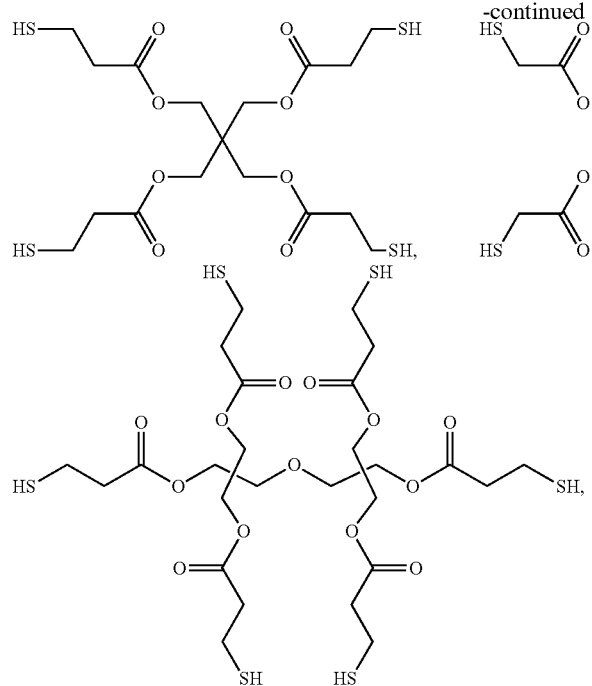
-continued
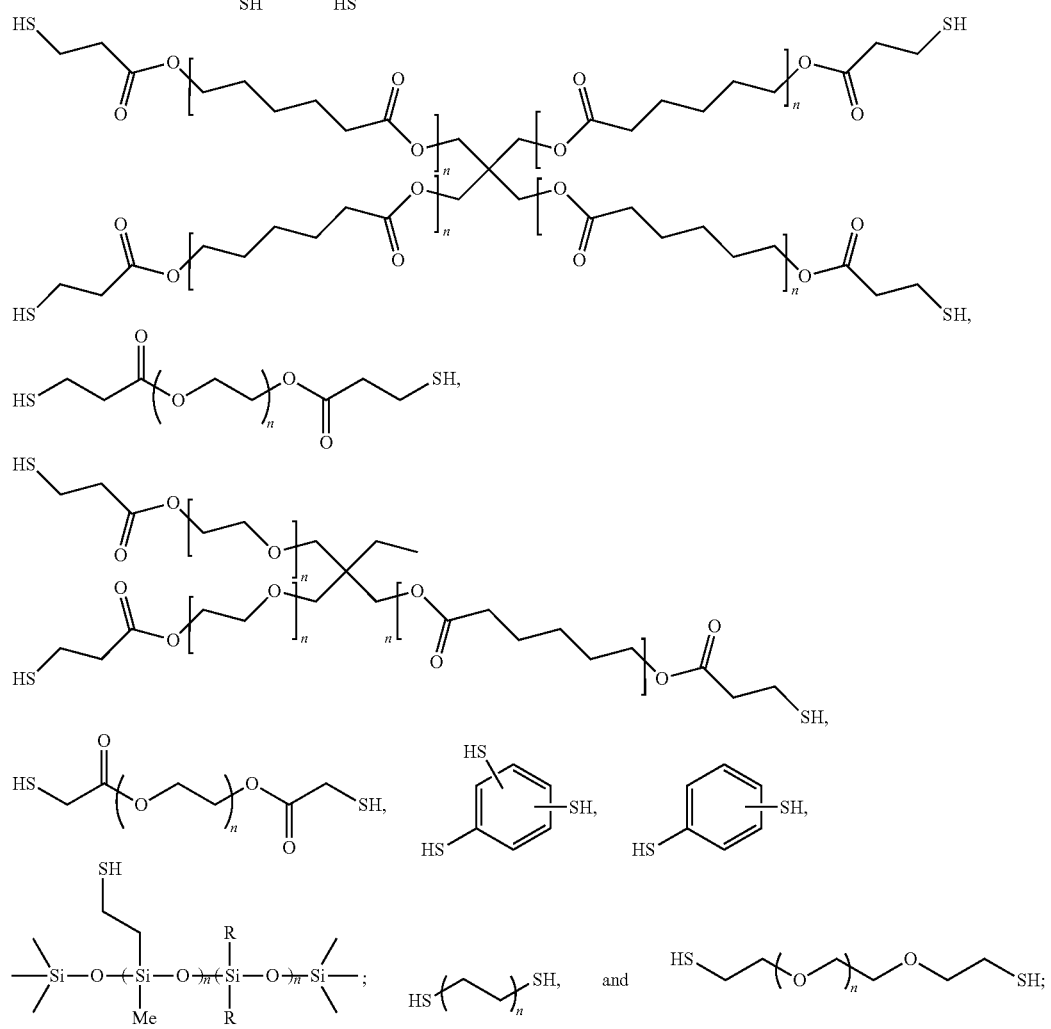

wherein each instance of n is independently an integer from 0 to 500; or wherein the at least one multifunctional thiol monomer is selected from the group consisting of: pentaerythritol tetramercaptopropionate (PETMP), ethylene glycol bis(3-mercaptopropionate) (EGBMP); trimethylolpropane tris(3-mercaptopropionate) (TMPMP), 2,4,6-trioxo-1,3,5-triazina-triy (triethyltris (3-mercapto propionate); 1,2-ethanedithiol, 1,3-propanedithiol, 1,4-butanedithiol; 1,5-pentanedithiol; 1,6-hexanedithiol, 1,8-octanedithiol, 1,9-nonanedithiol, 1,11-undecanedithiol; 1,16-hexadecanedithiol, 2,5-dimercaptomethyl-1,4-dithiane, pentaerythritol tetramercaptoacetate; trimethylolpropane trimercaptoacetate; glycol dimercaptoacetate, 2,3-dimercapto-1-propanol; DL-dithiothreitol; 2-mercaptoethylsulfide, 2,3-(dimercaptoethylthio)-1-mercaptopropane, 1,2,3-trimercaptopropane, toluenedithiol; benzenedithiol, biphenyldithiol, benzenedimethanethiol; xylylenedithiol, 4,4'-dimercaptostilbene, glycol dimercaptopropionate, and combinations thereof; or wherein the thiol-ene polymer comprises an ene monomer selected from a group consisting of ethylene glycoldi(meth)acrylate, ethoxylated bisphenol-A dimethacrylate (EBPADMA), tetraethyleneglycoldi(meth)acrylate (TEGDMA), poly(ethylene glycol) dimethacrylates, the condensation product of bisphenol A and glycidyl methacrylate, 2,2'-bis-[4-(3-methacryloxy-2-hydroxy propoxy)-phenyl]propane (BisGMA), hexanediol di(meth)acrylate, tripropylene glycol di(meth)acrylate, butanediol di(meth) acrylate, neopentyl glycol di(meth) acrylate, diethylene glycol di(meth)acrylate, triethylene glycol di(meth) acrylate, dipropylene glycol di(meth)acrylate, trimethylolpropane triacrylate (TMPTA), di(trimethylolpropane) tetraacrylate (DTPTA), divinyl sulfone (DVS), propargyl acrylate, 6-azidohexyl acrylate, [2-(acryloyloxy)ethyl]trimethylammonium chloride, acrylic acid, 2-(4-benzoyl-3-hydroxyphenoxy)ethyl acrylate, 3-sulfopropyl acrylate potassium salt, 2-hydroxyethyl acrylate and 2-(dimethylamino)ethyl acrylate, 1,1'-(methylenedi-4,1-phenylene)bismaleimide, 1,4-di(maleimido)butane, N,N'-phenylenedimaleimide, N,N'-methylenebisacrylamide, triallyl-1,3,5-triazine-2,4,6-trione (TATATO), triethyleneglycol divinyl ether (TEGDVE), trimethylolpropane diallyl ether, dodecyl vinyl ether (DDVE), 1,6-heptadiyne, 1,7-octadiyne, bis-2,2-[4-(2-[norborn-2-ene-5-carboxylate]ethoxy) phenyl] propane (BPAEDN), 1,6-hexanediol di-(endo,exo-norborn-2-ene-5-carboxylate) (HDDN), trimethylolpropane tri-(norborn-2-ene-5-carboxylate) (TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), di(trimethylolpropane) tetra-(norborn-2-ene-5-carboxylate) (DTMPTN), and combinations thereof.

3. The composition of claim 1,
wherein group (a) comprises —SCH$_2$C(=CH$_2$)CH$_2$SH;
or
wherein the linker comprises group (b) and the polymer comprises at least one free thiol from the at least one multifunctional thiol monomer;
or
wherein group (b) comprises a linker of formula (Ia):

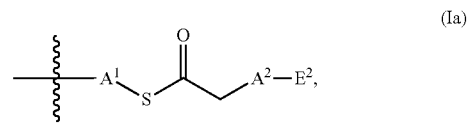

or
wherein group (b) comprises a linker selected from the group consisting of:

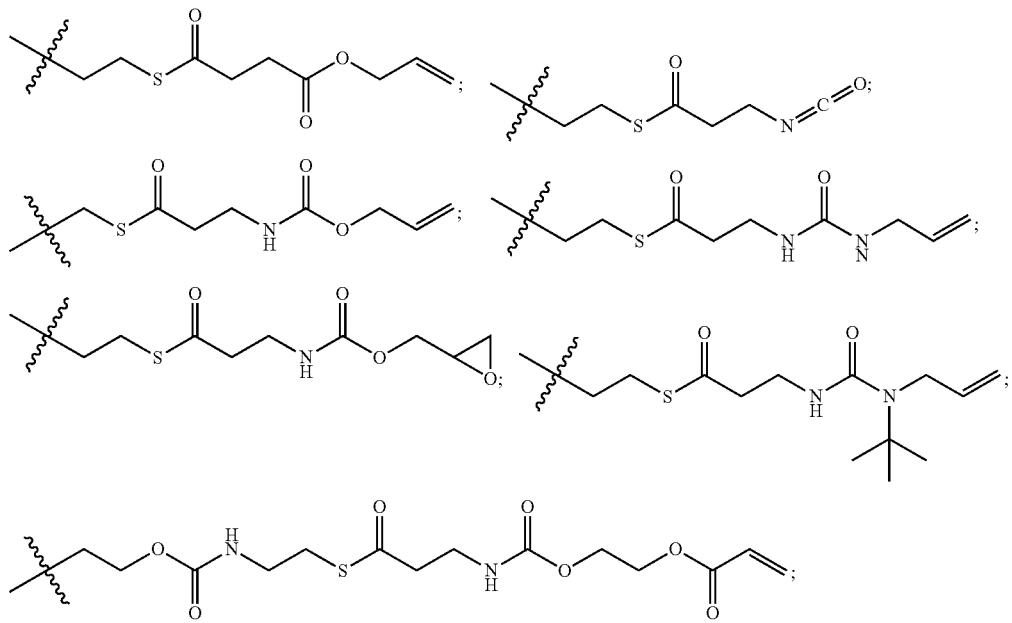

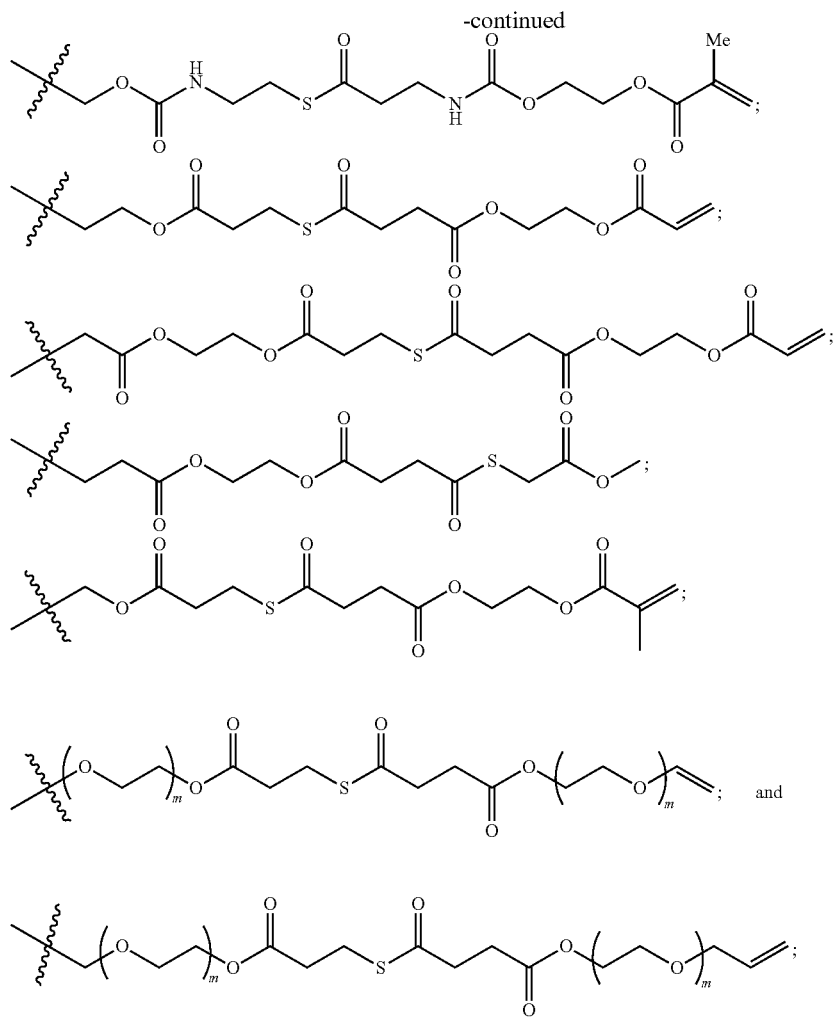

wherein each occurrence of m is independently selected from the group consisting of 0, 1, 2, 3, 4, 5, and 6.

4. The composition of claim 1, wherein the linker comprises group (b) and the polymer comprises at least one free thiol from the at least one multifunctional thiol monomer.

5. The composition of claim 1, further comprising at least one polymerization initiator selected from the group consisting of a photoinitiator, a thermal initiator, and a redox initiator.

6. The composition of claim 5, wherein the at least one photoinitiator is selected from the group consisting of: acetophenone, benzophenone, 2-phenylacetophenone, 2,2-dimethoxy-2-phenylacetophenone, bis(2,4,6-trimethylbenzoyl)-phenylphosphineoxide, 2-hydroxy-4'-(2-hydroxyethoxy)-2-methylpropiophenone, 2-methyl-(4-methylthienyl)-2-morpholinyl-1-propan-1-one, Diphenyl diphenyl(2,4,6-trimethylbenzoyl)phosphine oxide, ethyl (2,4,6-trimethylbenzoyl) phenyl phosphinate, lithium phenyl-2,4,6-trimethylbenzoylphosphinate,

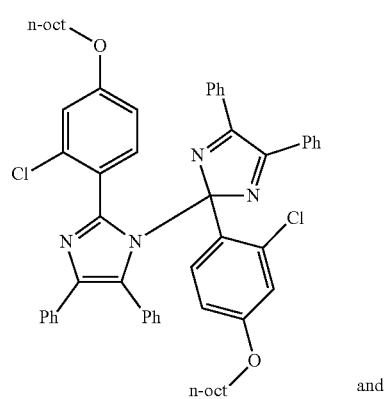

and

-continued

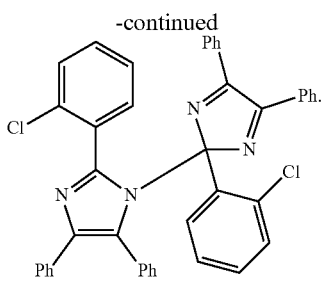

7. The composition of claim 5, wherein the at least one thermal initiator is a compound selected from the group consisting of tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, and potassium persulfate.

8. The composition of claim 5, wherein the at least one redox initiator is selected from the group consisting of: sodium iodide/hydrogen peroxide, potassium iodide/hydrogen peroxide, benzoyl peroxide/dimethyaniline, benzoyl peroxide/N,N-dimethyl p-toluidine, benzoyl peroxide/4-N,N-dimethylaminophenethyl alcohol, benzoyl peroxide/ethyl 4-dimethylamino benzoate, glucose oxidase/oxygen/iron(II) sulfate; and copper(II) sulfate/sodium ascorbate.

9. The composition of claim 1, further comprising a catalyst selected from the group consisting of a nucleophile and a base.

10. The composition of claim 9, wherein the nucleophile is selected from the group consisting of quinuclidine, 1,4-diazabicyclo[2.2.2]octane (DABCO), 4-dimethylaminopyridine (DMAP), IMes (1,3-bis(2,4,6-trimethylphenyl)-1,3-dihydro-2H-imidazol-2-ylidene), IPr (1,3-bis(2,6-diisopropylphenyl)-1,3-dihydro-2H-imidazol-2-ylidene), Ender's carbene, $PPh_3$, $P(nBu)_3$, $P(tBu)_3$, $PCy_3$, and $PMe_3$.

11. The composition of claim 9, wherein the base deprotonates at least about 10% of the thiol groups in the composition.

12. The composition of claim 9, wherein the base is selected from the group consisting of an alkylthiolate salt, tetramethylguanidine (TMG), 1,8-diazabicyclo[5,4,0]undec-7-ene (DBU), N,N-diisopropylethylamine (DIPEA or Hunig's base), 4-tert-butyl pyridine, triethylamine (TEA), and N,N,N',N'',N''-pentamethyldiethylenetriamine (PMDETA).

13. A method of forming a polymer-filler composite, the method comprising:
combining at least one nanoparticle (NP), at least one multifunctional thiol monomer, at least one ene monomer, and at least one polymerization initiator to form an uncured polymer-filler composite; and
activating the at least one polymerization initiator to form the polymer-filler composite,
wherein the at least one nanoparticle is functionalized with a linker comprising at least one of the following groups:

(a) at least one allylic terminal thiol (—SH) group;
or
(b) at least one multifunctional thioester of formula (I),

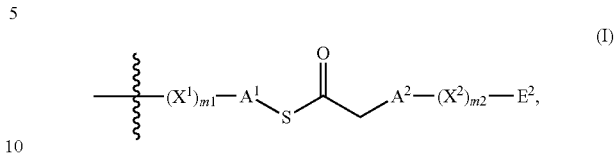

wherein:
$A^1$ and $A^2$ are each independently selected from the group consisting of optionally substituted $C_1$-$C_{15}$ alkylene, optionally substituted $C_2$-$C_{15}$ alkenylene, optionally substituted $C_2$-$C_{15}$ alkynylene, optionally substituted $C_2$-$C_{15}$ heteroalkylene, optionally substituted $C_2$-$C_{15}$ heteroalkenylene and optionally substituted $C_2$-$C_{15}$ heteroalkynylene;
$E^2$ is selected from the group consisting of:

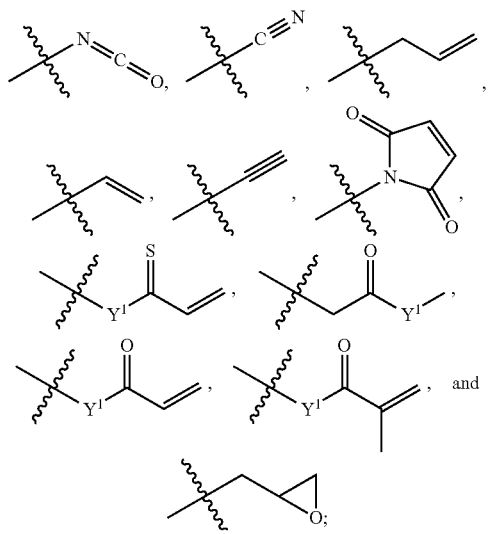

each instance of $Y^1$ is independently selected from the group consisting of O and $N(R^1)$; and
each instance of $R^1$ being independently selected from the group consisting of H and $C_1$-$C_6$ alkyl;
m1 is 0 or 1;
m2 is 0 or 1;
$X^1$ is

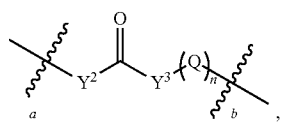

wherein:
bond a is to $A^1$,
Q is $CH_2$ or

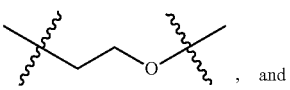 [SMILES: *CCO*]

, and n is 0, 1, 2, 3, 4, 5 or 6;

$X^2$ is

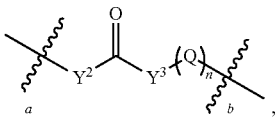

wherein:
bond a is to $A^2$,
bond b is to $E^2$,
Q is $CH_2$ or

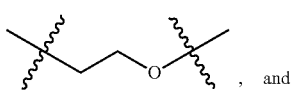 [SMILES: *CCO*], and n is 0, 1, 2, 3, 4, 5 or 6;

each instance of $Y^2$ is independently selected from the group consisting of $C(R^1)_2$, O, and $NR^1$; and each instance of $Y^3$ is independently selected from the group consisting of $C(R^1)_2$, O, and $NR^1$; and each instance of $R^1$ is independently selected from the group consisting of H and $C_1$-$C_6$ alkyl.

14. The method of claim 13, wherein the at least one polymerization initiator is selected from the group consisting of a photoinitiator, a thermal initiator, and a redox initiator.

15. The method of claim 14, wherein the at least one photoinitiator is selected from the group consisting of: acetophenone, benzophenone, 2-phenylacetophenone, 2,2-dimethoxy-2-phenylacetophenone, bis(2,4,6-trimethylbenzoyl)-phenylphosphineoxide, 2-hydroxy-4'-(2-hydroxyethoxy)-2-methylpropiophenone, 2-methyl-(4-methylthienyl)-2-morpholinyl-1-propan-1-one, diphenyl(2,4,6-trimethylbenzoyl)phosphine oxide, ethyl (2,4,6-trimethylbenzoyl) phenyl phosphinate, lithium phenyl-2,4,6-trimethylbenzoylphosphinate,

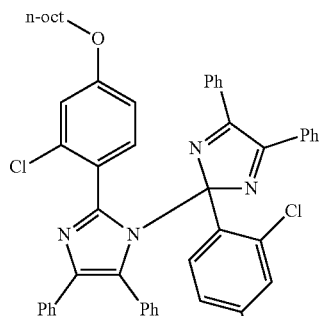

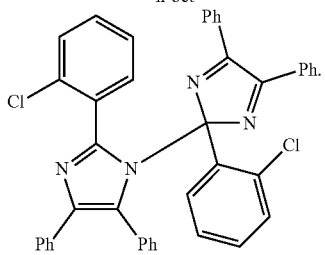 and

16. The method of claim 14, wherein the at least one thermal initiator is a compound selected from the group consisting of tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, and potassium persulfate.

17. The method of claim 13, wherein the at least one multifunctional thiol monomer is selected from the group consisting of:

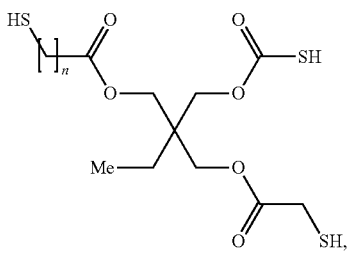
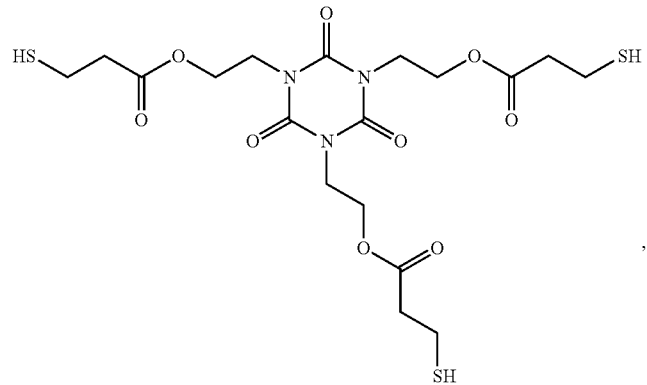

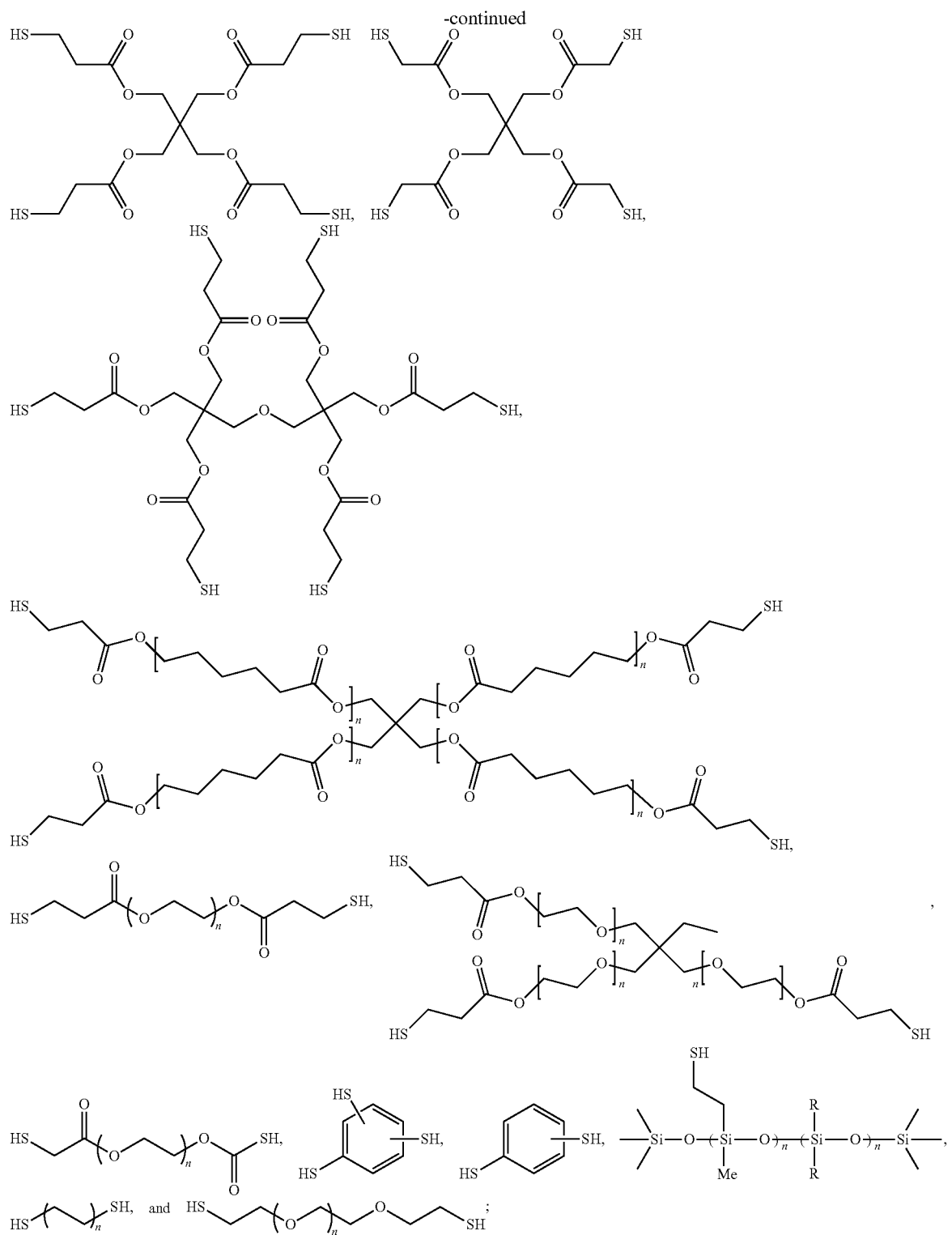

wherein each instance of n is independently an integer from 0 to 500; or wherein the at least one multifunctional thiol monomer is selected from the group consisting of: pentaerythritol tetramercaptopropionate (PETMP), ethylene glycol bis(3-mercaptopropionate) (EGBMP); trimethylolpropane tris(3-mercaptopropionate) (TMPMP), 2,4,6-trioxo-1,3,5-triazina-triy (triethyl-tris (3-mercapto propionate); 1,2-ethanedithiol, 1,3-propanedithiol, 1,4-butanedithiol; 1,5-pentanedithiol; 1,6-hexanedithiol, 1,8-octanedithiol, 1,9-nonanedithiol, 1,11-undecanedithiol; 1,16-hexadecanedithiol, 2,5-dimercaptomethyl-1,4-dithiane, pentaerythritol tetramercaptoacetate; trimethylolpropane trimercaptoacetate; glycol dimercaptoacetate, 2,3-dimercapto-1-propanol; DL-dithiothreitol; 2-mercaptoethylsulfide, 2,3-(dimercaptoethylthio)-1-mercaptopropane, 1,2,3-trimercaptopropane, toluenedithiol; benzenedithiol, biphenyldithiol, benzenedimethanethiol; xylylenedithiol, 4,4'-dimercaptostilbene, glycol dimercaptopropionate, and combinations thereof, or wherein the thiol-ene polymer comprises an ene monomer selected from a group consisting of ethylene glycoldi(meth)acrylate, ethoxylated bisphenol-A dimethacrylate (EBPADMA), tetraethyleneglycoldi(meth)acrylate (TEGDMA), poly(ethylene glycol) dimethacrylates, the condensation product of bisphenol A and glycidyl methacrylate, 2,2'-bis-[4-(3-methacryloxy-2-hydroxy propoxy)-phenyl]propane (Bis-GMA), hexanediol di(meth)acrylate, tripropylene glycol di(meth)acrylate, butanediol di(meth) acrylate, neopentyl glycol di(meth) acrylate, diethylene glycol di(meth)acrylate, triethylene glycol di(meth) acrylate, dipropylene glycol di(meth)acrylate, trimethylolpropane triacrylate (TMPTA), di(trimethylolpropane) tetraacrylate (DTPTA), divinyl sulfone (DVS), propargyl acrylate, 6-azidohexyl acrylate, [2-(acryloyloxy)ethyl]trimethylammonium chloride, acrylic acid, 2-(4-benzoyl-3-hydroxyphenoxy)ethyl acrylate, 3-sulfopropyl acrylate potassium salt, 2-hydroxyethyl acrylate and 2-(dimethylamino)ethyl acrylate, 1,1'-(methylenedi-4,1-phenylene)bismaleimide, 1,4-di(maleimido)butane, N,N'-phenylenedimaleimide, N,N'-methylenebisacrylamide, triallyl-1,3,5-triazine-2,4,6-trione (TATATO), triethyleneglycol divinyl ether (TEGDVE), trimethylolpropane diallyl ether, dodecyl vinyl ether (DDVE), 1,6-heptadiyne, 1,7-octadiyne, bis-2,2-[4-(2-[norborn-2-ene-5-carboxylate]ethoxy) phenyl] propane (BPAEDN), 1,6-hexanediol di-(endo,exo-norborn-2-ene-5-carboxylate) (HDDN), trimethylolpropane tri-(norborn-2-ene-5-carboxylate) (TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), di(trimethylolpropane) tetra-(norborn-2-ene-5-carboxylate) (DTMPTN), and combinations thereof.

18. The method of claim 13,
wherein group (a) comprises —$SCH_2C(=CH_2)CH_2SH$;
or
wherein the linker comprise group (b) and the polymer comprises at least one free thiol from the at least one multifunctional thiol monomer;
or
wherein group (b) comprises a linker of formula (Ia):

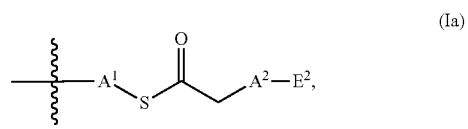

or
wherein group (b) comprises a linker selected from the group consisting of:

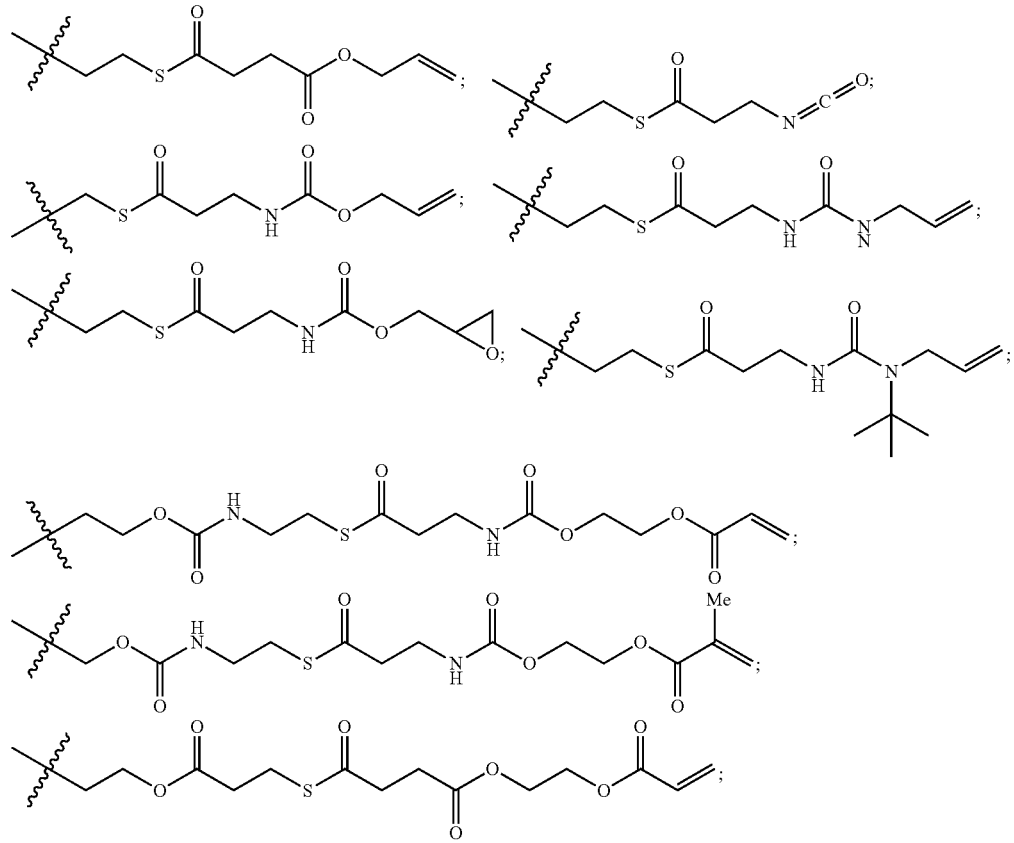

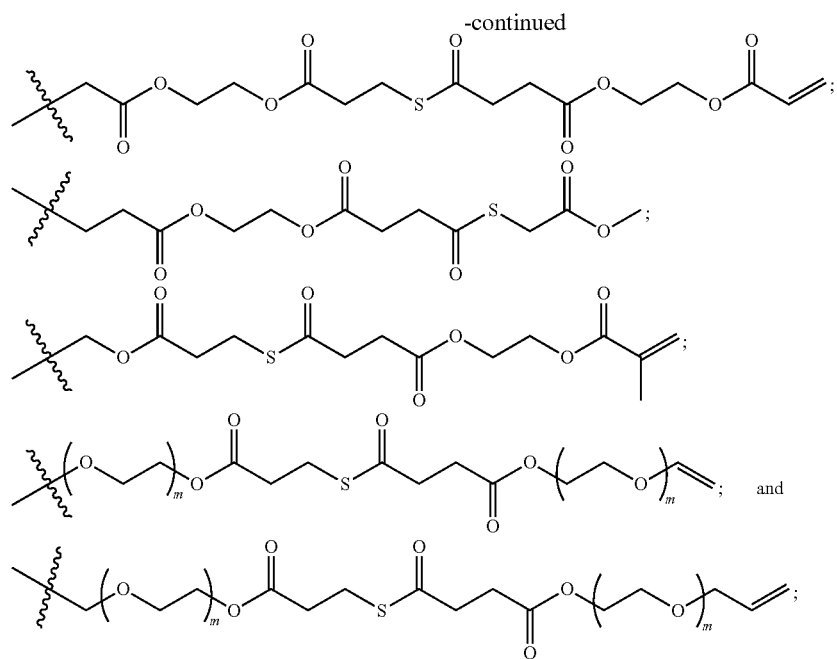
wherein each occurrence of m is independently selected from the group consisting of 0, 1, 2, 3, 4, 5, and 6.
* * * * *